(12) United States Patent
Coleman et al.

(10) Patent No.: US 9,643,982 B2
(45) Date of Patent: May 9, 2017

(54) FUSED TRICYCLIC HETEROCYCLIC COMPOUNDS AS HIV INTEGRASE INHIBITORS

(71) Applicant: Merck Sharp & Dohme Corp., Rahway, NJ (US)

(72) Inventors: Paul J. Coleman, Harleysville, PA (US); Timothy J. Hartingh, Blue Bell, PA (US); Izzat T. Raheem, Doylestown, PA (US); John Schreier, Harleysville, PA (US); John Sisko, Lansdale, PA (US); John Wai, Harleysville, PA (US); Thomas H. Graham, Scotch Plains, NJ (US); Lihong Hu, Shanghai (CN); Xuanjia Peng, Shanghai (CN)

(73) Assignee: MERCK SHARP & DOHME CORP., Rahway, NJ (US)

( * ) Notice: Subject to any disclaimer, the term of this patent is extended or adjusted under 35 U.S.C. 154(b) by 0 days.

(21) Appl. No.: 14/892,754

(22) PCT Filed: Apr. 18, 2014

(86) PCT No.: PCT/CN2014/075685
§ 371 (c)(1),
(2) Date: Nov. 20, 2015

(87) PCT Pub. No.: WO2014/183532
PCT Pub. Date: Nov. 20, 2014

(65) Prior Publication Data
US 2016/0108059 A1    Apr. 21, 2016

Related U.S. Application Data

(60) Provisional application No. 61/824,739, filed on May 17, 2013.

(51) Int. Cl.
| C07D 498/16 | (2006.01) |
| C07D 471/16 | (2006.01) |
| A61K 31/5383 | (2006.01) |
| A61K 31/4985 | (2006.01) |
| A61K 45/06 | (2006.01) |
| C07D 487/16 | (2006.01) |
| C07D 491/16 | (2006.01) |

(52) U.S. Cl.
CPC ........ C07D 498/16 (2013.01); A61K 31/4985 (2013.01); A61K 31/5383 (2013.01); A61K 45/06 (2013.01); C07D 471/16 (2013.01); C07D 487/16 (2013.01); C07D 491/16 (2013.01)

(58) Field of Classification Search
CPC C07D 498/16; C07D 471/16; A61K 31/5383; A61K 31/4985; A61K 45/06
USPC .............. 544/101; 514/229.8, 250
See application file for complete search history.

(56) References Cited

U.S. PATENT DOCUMENTS

| 7,037,908 B2 | 5/2006 | Naidu et al. |
| 7,115,601 B2 | 10/2006 | Naidu et al. |
| 7,135,467 B2 | 11/2006 | Walker et al. |
| 7,157,447 B2 | 1/2007 | Naidu et al. |
| 7,169,780 B2 | 1/2007 | Crescenzi et al. |
| 7,173,022 B2 | 2/2007 | Naidu et al. |
| 7,176,196 B2 | 2/2007 | Naidu et al. |
| 7,192,948 B2 | 3/2007 | Banville et al. |
| 7,211,572 B2 | 5/2007 | Miyazaki |
| 7,217,713 B2 | 5/2007 | Crescenzi et al. |
| 7,232,819 B2 | 6/2007 | Di Francesco et al. |
| 7,273,859 B2 | 9/2007 | Naidu |
| 7,279,487 B2 | 10/2007 | Egbertson et al. |
| 7,414,045 B2 | 8/2008 | Crescenzi et al. |
| 7,419,969 B2 | 9/2008 | Naidu et al. |
| 2004/0229909 A1 | 11/2004 | Kiyama et al. |
| 2006/0276466 A1 | 12/2006 | Naidu et al. |

(Continued)

FOREIGN PATENT DOCUMENTS

| EP | 1544199 B1 | 10/2008 |
| EP | 2540720 B1 | 4/2015 |

(Continued)

OTHER PUBLICATIONS

Berge et al., Pharmaceutical Salts, J. Pharm Sci., 1977, pp. 1-19, 66(1).

(Continued)

*Primary Examiner* — Kahsay Habte
(74) *Attorney, Agent, or Firm* — Nicole M. Beeler; Catherine D. Fitch

(57) ABSTRACT

The present invention relates to Fused Tricyclic Heterocycle Derivatives of Formula (I), and pharmaceutically acceptable salts thereof, wherein $R^1$-$R^8$, A, X and n are as defined herein. The present invention also relates to compositions comprising at least one Fused Tricyclic Heterocycle Derivative, and methods of using the Fused Tricyclic Heterocycle Derivatives for treating or preventing HIV infection in a subject.

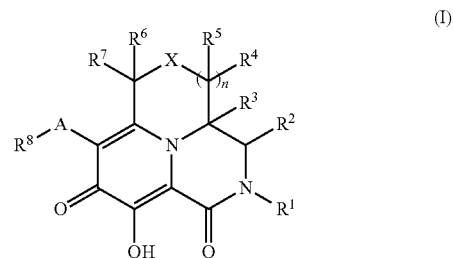

14 Claims, No Drawings

(56) References Cited

U.S. PATENT DOCUMENTS

| | | | |
|---|---|---|---|
| 2007/0049606 | A1 | 3/2007 | Banville et al. |
| 2007/0083045 | A1 | 4/2007 | Di Francesco et al. |
| 2007/0111984 | A1 | 5/2007 | Naidu et al. |
| 2007/0111985 | A1 | 5/2007 | Naidu et al. |
| 2007/0112190 | A1 | 5/2007 | Naidu |
| 2007/0123524 | A1 | 5/2007 | Crescenzi et al. |
| 2007/0142635 | A1 | 6/2007 | Askin et al. |
| 2007/0149556 | A1 | 6/2007 | Mikamiyama et al. |
| 2007/0281917 | A1 | 12/2007 | Naidu et al. |
| 2008/0004265 | A1 | 1/2008 | Walker et al. |

FOREIGN PATENT DOCUMENTS

| | | |
|---|---|---|
| WO | 2005086700 A2 | 9/2005 |
| WO | 2005087766 A1 | 9/2005 |
| WO | 2005087768 A1 | 9/2005 |
| WO | 2005092099 A1 | 10/2005 |
| WO | 2006103399 A1 | 10/2006 |
| WO | 2011045330 A1 | 4/2011 |
| WO | 2011121105 A1 | 10/2011 |

OTHER PUBLICATIONS

Bingham et al., Over one hundred solvates of sulfathiazole, Chem. Commun., 2001, 603-604.

Caira et al., Preparation and Crystal Characterization of a Polymorph, a Monohydrate, and an Ethyl Acetate Solvate of the Antifungal Fluconazole, J. Pharmaceutical Sci, 2004, 601-611, 93(3).

Muraglia, E., et al, Design and Synthesis of Bicyclic Pyrimidinones as Potent and Orally Bioavailable HIV-1 Integrase Inhibits, J. Med. Chem., 2008, pp. 861-874, vol. 51, US.

Gould, Salt selection for basic drugs, International J. of Pharmaceutics, 1986, 201-217, 33.

Green & Wuts, Protective Groups in Organic Synthesis, 2nd Edition, 1991.

Greene, et al., Protection for the Carbonyl Group, Organic Synthesis, 1999, pp. 312-344.

Toh, H. et al., Close Structural Resemblance Between Putative Polymerase Of A *Drosophila* Transposable Genetic Element 17.5 and Pol Gene Product of Moloney Murine Leukaemia Virus, the EMBO Journal, 1985, pp. 1267-1272, vol. 4, No. 5, US.

International Search Report and Written Opinion for PCT/CN2014/075685 mailed Jul. 9, 2014, 17 pages.

Pearl, L. P., et al., A Structural Model For The Retroviral Proteases, Nature, 1987, pp. 351-354, vol. 329, US.

Ratner, LO., et al., Complete Nucleotide Sequence Of AIDS Virus, HTLV-III, Nature, 1985, pp. 277-284, vol. 313, US.

Ferrara, M., et al., Synthesis of a Hexahydropyrimido[1,2-a]Azepine-2-Carboxamide Derivative Useful As An HIV Integrase Inhibitor, Tetrahedron Letters, Jul. 2007, pp. 8379-8382, vol. 48, No. 37, US.

Power, M. D., et al.,T AL, Nucleotide Sequence of SRV-1, a Type D Simian, Science, 1986, pp. 1572, vol. 231, US.

Kinzel, O. D., et al., The Syntheis Of Tetrahydropyridopyrimidones As A New Scaffold For HIV-1 Integrase Inhibitors, Tetrahedron Letters, 2007, pp. 6552-6555, vol. 48, No. 37, US.

Toh, H. et al., Pro-drugs as NovelDelivery Systems (1987) 14 of the A.C.S. Symposium Series.

Van Tonder, et al., Preparation and Physicochemical Characterization of 5 Niclosamide Solvates and 1 Hemisolvate, AAPS Pharmscitech, 2004, pp. 1-10, 5(1), US.

Extended European Search Report for 14798188.0, mailed Sep. 23, 2016, 7 pages.

9,643,982 B2

FUSED TRICYCLIC HETEROCYCLIC COMPOUNDS AS HIV INTEGRASE INHIBITORS

CROSS-REFERENCE TO RELATED APPLICATIONS

This application is the national stage application under 35 U.S.C. 371 of International Patent Application No. PCT/CN2014/075685, filed Apr. 18, 2014, which claims priority to U.S. Provisional Application No. 61/824,739, filed May 17, 2013. Each of the aforementioned PCT and priority applications is incorporated by reference in its entirety.

FIELD OF THE INVENTION

The present invention relates to Fused Tricyclic Heterocycle Derivatives, compositions comprising at least one Fused Tricyclic Heterocycle Derivative, and methods of using the Fused Tricyclic Heterocycle Derivatives for treating or preventing HIV infection in a subject.

BACKGROUND OF THE INVENTION

A retrovirus designated human immunodeficiency virus (HIV), particularly the strains known as HIV type-1 (HIV-1) virus and type-2 (HIV-2) virus, is the etiological agent of the complex disease that includes progressive destruction of the immune system (acquired immune deficiency syndrome; AIDS) and degeneration of the central and peripheral nervous system. A common feature of retrovirus replication is the insertion by virally-encoded integrase of +proviral DNA into the host cell genome, a required step in HIV replication in human T-lymphoid and monocytoid cells. Integration is believed to be mediated by integrase in three steps: assembly of a stable nucleoprotein complex with viral DNA sequences; cleavage of two nucleotides from the 3' termini of the linear proviral DNA; covalent joining of the recessed 3' OH termini of the proviral DNA at a staggered cut made at the host target site. The fourth step in the process, repair synthesis of the resultant gap, may be accomplished by cellular enzymes.

Nucleotide sequencing of HIV shows the presence of a pol gene in one open reading frame [Ratner, L. et al., Nature, 313, 277(1985)]. Amino acid sequence homology provides evidence that the pol sequence encodes reverse transcriptase, integrase and an HIV protease [Toh, H. et al., EMBO J. 4, 1267 (1985); Power, M. D. et al., Science, 231, 1567 (1986); Pearl, L. H. et al., Nature, 329, 351 (1987)]. All three enzymes have been shown to be essential for the replication of HIV.

It is known that some antiviral compounds which act as inhibitors of HIV replication are effective agents in the treatment of AIDS and similar diseases, including reverse transcriptase inhibitors such as azidothymidine (AZT) and efavirenz and protease inhibitors such as indinavir and nelfinavir. The compounds of this invention are inhibitors of HIV integrase and inhibitors of HIV replication.

The following references are of interest as background:

International Publication Nos. WO 11/045330 and WO 11/121105 disclose macrocyclic compounds having HIV integrase inhibitory activity.

Kinzel et al., Tet. Letters 2007, 48(37): pp. 6552-6555 discloses the synthesis of tetrahydropyridopyrimidones as a scaffold for HIV-1 integrase inhibitors.

Ferrara et al., Tet. Letters 2007, 48(37), pp. 8379-8382 discloses the synthesis of a hexahydropyrimido[1,2-a]azepine-2-carboxamide derivative useful as an HIV integrase inhibitor.

Muraglia et al., J. Med. Chem. 2008, 51: 861-874 discloses the design and synthesis of bicyclic pyrimidinones as potent and orally bioavailable HIV-1 integrase inhibitors.

US2004/229909 discloses certain compounds having integrase inhibitory activity.

U.S. Pat. No. 7,232,819 and US 2007/0083045 disclose certain 5,6-dihydroxypyrimidine-4-carboxamides as HIV integrase inhibitors.

U.S. Pat. No. 7,169,780, U.S. Pat. No. 7,217,713, and US 2007/0123524 disclose certain N-substituted 5-hydroxy-6-oxo-1,6-dihydropyrimidine-4-carboxamides as HIV integrase inhibitors.

U.S. Pat. No. 7,279,487 discloses certain hydroxynaphthyridinone carboxamides that are useful as HIV integrase inhibitors.

U.S. Pat. No. 7,135,467 and U.S. Pat. No. 7,037,908 disclose certain pyrimidine carboxamides that are useful as HIV integrase inhibitors.

U.S. Pat. No. 7,211,572 discloses certain nitrogenous condensed ring compounds that are HIV integrase inhibitors.

U.S. Pat. No. 7,414,045 discloses certain tetrahydro-4H-pyrido[1,2-a]pyrimidine carboxamides, hexahydropyrimido [1,2-a]azepine carboxamides, and related compounds that are useful as HIV integrase inhibitors.

WO 2006/103399 discloses certain tetrahydro-4H-pyrimidooxazepine carboxamides, tetrahydropyrazinopyrimidine carboxamides, hexahydropyrimidodiazepine carboxamides, and related compounds that are useful as HIV integrase inhibitors.

US 2007/0142635 discloses processes for preparing hexahydropyrimido[1,2-a]azepine-2-carboxylates and related compounds.

US 2007/0149556 discloses certain hydroxypyrimidinone derivatives having HIV integrase inhibitory activity.

Various pyrimidinone compounds useful as HIV integrase inhibitors are also disclosed in U.S. Pat. No. 7,115,601, U.S. Pat. No. 7,157,447, U.S. Pat. No. 7,173,022, U.S. Pat. No. 7,176,196, U.S. Pat. No. 7,192,948, U.S. Pat. No. 7,273,859, and U.S. Pat. No. 7,419,969.

US 2007/0111984 discloses a series of bicyclic pyrimidinone compounds useful as HIV integrase inhibitors.

US 2006/0276466, US 2007/0049606, US 2007/0111985, US 2007/0112190, US 2007/0281917, US 2008/0004265 each disclose a series of bicyclic pyrimidinone compounds useful as HIV integrase inhibitors.

SUMMARY OF THE INVENTION

In one aspect, the present invention provides Compounds of Formula (I):

and pharmaceutically acceptable salts and prodrugs thereof, wherein:

A is $C_1$-$C_4$ alkylene, $C_2$-$C_4$ alkenylene, arylene, $C_3$-$C_7$ cycloalkyl, 5 or 6-membered monocyclic heteroaryl, 4 to 7-membered heterocycloalkyl, —O—, —NH—C(O)—, —C(O)NH— or —C(O)—;

X is O, —N($C_1$-$C_6$ alkyl)- or —C($R^{10}$)($R^{11}$), such that when X=O or —N($C_1$-$C_6$ alkyl)-, then $R^4$, $R^5$, $R^6$ and $R^7$ are each other than —$OR^9$, —N($R^9$)$_2$ or halo;

each occurrence of m is independently 0 or 1;

n is 0 or 1, such that when n is 0, then $R^4$ and $R^5$ are not present;

$R^1$ is $C_1$-$C_6$ alkyl, which is optionally substituted with up to 3 groups, each independently selected from $C_3$-$C_7$ cycloalkyl, 5 or 6-membered monocyclic heteroaryl, 4 to 6-membered monocyclic heterocycloalkyl, $C_6$-$C_{10}$ aryl, halo, $C_1$-$C_6$ haloalkyl, —$OR^9$, —N($R^9$)$_2$, —C(O)$R^9$, —C(O)N($R^9$)$_2$, —NHC(O)$R^9$ and —$SR^9$, wherein said $C_3$-$C_7$ cycloalkyl group, said 5 or 6-membered monocyclic heteroaryl group, said 4 to 6-membered monocyclic heterocycloalkyl group and said $C_6$-$C_{10}$ aryl group can each be optionally and independently substituted with one or more groups, each independently selected from $C_1$-$C_6$ alkyl, $C_3$-$C_7$ cycloalkyl, 5 or 6-membered monocyclic heteroaryl, 4 to 6-membered monocyclic heterocycloalkyl, $C_6$-$C_{10}$ aryl, halo, $C_1$-$C_6$ haloalkyl, —$OR^9$, —N($R^9$)$_2$, —C(O)$R^9$, —C(O)N($R^9$)$_2$, —NHC(O)$R^9$ and —$SR^9$;

$R^2$, $R^5$, $R^6$, $R^7$, $R^{10}$ and $R^{11}$ are each independently selected from H, $C_1$-$C_6$ alkyl, $C_3$-$C_7$ cycloalkyl, halo, $C_1$-$C_6$ haloalkyl, —$OR^9$, —N($R^9$)$_2$, —C(O)$R^9$, —C(O)N($R^9$)$_2$ and —NHC(O)$R^9$, wherein said $C_1$-$C_6$ alkyl group can be optionally substituted with one or more groups, each independently selected from halo, —OH, —O($C_1$-$C_6$ alkyl), —$NH_2$, —NH($C_1$-$C_6$ alkyl), —N($C_1$-$C_6$ alkyl)$_2$, —SH or —S($C_1$-$C_6$ alkyl);

$R^3$ is H, $C_1$-$C_6$ alkyl, $C_3$-$C_7$ cycloalkyl, $C_1$-$C_6$ haloalkyl, —C(O)$R^9$, —C(O)N($R^9$)$_2$ and —NHC(O)$R^9$, wherein said $C_1$-$C_6$ alkyl group can be optionally substituted with one or more groups, each independently selected from halo, —OH, —O($C_1$-$C_6$ alkyl), —$NH_2$, —NH($C_1$-$C_6$ alkyl), —N($C_1$-$C_6$ alkyl)$_2$, —SH or —S($C_1$-$C_6$ alkyl);

$R^4$ is H, or $R^4$ and $R^5$ and the common carbon atom to which they are attached, join to form an endocyclic —C(O)— group;

$R^8$ is selected from $C_1$-$C_6$ alkyl, —($C_1$-$C_3$ alkylene)$_m$-($C_3$-$C_7$ cycloalkyl), —($C_1$-$C_3$ alkylene)$_m$-(5 or 6-membered monocyclic heteroaryl), —($C_1$-$C_3$ alkylene)$_m$-(4 to 6-membered monocyclic heterocycloalkyl) and —($C_1$-$C_3$ alkylene)$_m$-($C_6$-$C_{10}$ aryl), wherein said $C_3$-$C_7$ cycloalkyl group, said 5 or 6-membered monocyclic heteroaryl group, said 4 to 6-membered monocyclic heterocycloalkyl group and said $C_6$-$C_{10}$ aryl group can each be optionally and independently substituted with up to 5 groups, each independently selected from $C_1$-$C_6$ alkyl, $C_3$-$C_7$ cycloalkyl, 5 or 6-membered monocyclic heteroaryl, 4 to 6-membered monocyclic heterocycloalkyl, $C_6$-$C_{10}$ aryl, halo, $C_1$-$C_6$ haloalkyl, —$OR^9$, —N($R^9$)$_2$, —C(O)$R^9$, —C(O)N($R^9$)$_2$, —NHC(O)$R^9$ and —$SR^9$; and each occurrence of $R^9$ is independently selected from H, $C_1$-$C_6$ alkyl, $C_3$-$C_7$ cycloalkyl, $C_6$-$C_{10}$ aryl and benzyl.

The Compounds of Formula (I) (also referred to herein as the "Fused Tricyclic Heterocycle Derivatives") and pharmaceutically acceptable salts thereof can be useful, for example, for inhibiting HIV viral replication or replicon activity, and for treating or preventing HIV infection in a subject. Without being bound by any specific theory, it is believed that the Fused Tricyclic Heterocycle Derivatives inhibit HIV viral replication by inhibiting HIV Integrase.

Accordingly, the present invention provides methods for treating or preventing HIV infection in a subject, comprising administering to the subject an effective amount of at least one Fused Tricyclic Heterocycle Derivative.

The details of the invention are set forth in the accompanying detailed description below.

Although any methods and materials similar to those described herein can be used in the practice or testing of the present invention, illustrative methods and materials are now described. Other embodiments, aspects and features of the present invention are either further described in or will be apparent from the ensuing description, examples and appended claims.

DETAILED DESCRIPTION OF THE INVENTION

The present invention relates to Fused Tricyclic Heterocycle Derivatives, compositions comprising at least one Fused Tricyclic Heterocycle Derivative, and methods of using the Fused Tricyclic Heterocycle Derivatives for inhibiting HIV integrase, inhibiting HIV viral replication or for treating or preventing HIV infection in a subject.

DEFINITIONS AND ABBREVIATIONS

The terms used herein have their ordinary meaning and the meaning of such terms is independent at each occurrence thereof. That notwithstanding and except where stated otherwise, the following definitions apply throughout the specification and claims. Chemical names, common names, and chemical structures may be used interchangeably to describe the same structure. These definitions apply regardless of whether a term is used by itself or in combination with other terms, unless otherwise indicated. Hence, the definition of "alkyl" applies to "alkyl" as well as the "alkyl" portions of "hydroxyalkyl," "haloalkyl," "—O-alkyl," etc. . . . .

As used herein, and throughout this disclosure, the following terms, unless otherwise indicated, shall be understood to have the following meanings:

A "subject" is a human or non-human mammal. In one embodiment, a subject is a human. In another embodiment, a subject is a primate. In another embodiment, a subject is a monkey. In another embodiment, a subject is a chimpanzee. In still another embodiment, a subject is a rhesus monkey.

The term "effective amount" as used herein, refers to an amount of Fused Tricyclic Heterocycle Derivative and/or an additional therapeutic agent, or a composition thereof that is effective in producing the desired therapeutic, ameliorative, inhibitory or preventative effect when administered to a subject suffering from HIV infection or AIDS. In the combination therapies of the present invention, an effective amount can refer to each individual agent or to the combination as a whole, wherein the amounts of all agents administered are together effective, but wherein the component agent of the combination may not be present individually in an effective amount.

The term "preventing," as used herein with respect to an HIV viral infection or AIDS, refers to reducing the likelihood or severity of HIV infection or AIDS.

The term "alkyl," as used herein, refers to an aliphatic hydrocarbon group having one of its hydrogen atoms replaced with a bond. An alkyl group may be straight or branched and contain from about 1 to about 20 carbon atoms. In one embodiment, an alkyl group contains from about 1 to about 12 carbon atoms. In different embodiments, an alkyl group contains from 1 to 6 carbon atoms ($C_1$-$C_6$ alkyl) or from about 1 to about 4 carbon atoms ($C_1$-$C_4$ alkyl). Non-limiting examples of alkyl groups include methyl, ethyl, n-propyl, isopropyl, n-butyl, sec-butyl, isobutyl, tert-butyl, n-pentyl, neopentyl, isopentyl, n-hexyl, isohexyl and neohexyl. An alkyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —$NH_2$, —NH(alkyl), —N(alkyl)$_2$, —NH(cycloalkyl), —O—C(O)-alkyl, —O—C(O)-aryl, —O—C(O)-cycloalkyl, —C(O)OH and —C(O)O-alkyl. In one embodiment, an alkyl group is linear. In another embodiment, an alkyl group is branched. Unless otherwise indicated, an alkyl group is unsubstituted.

The term "alkenyl," as used herein, refers to an aliphatic hydrocarbon group containing at least one carbon-carbon double bond and having one of its hydrogen atoms replaced with a bond. An alkenyl group may be straight or branched and contain from about 2 to about 15 carbon atoms. In one embodiment, an alkenyl group contains from about 2 to about 12 carbon atoms. In another embodiment, an alkenyl group contains from about 2 to about 6 carbon atoms. Non-limiting examples of alkenyl groups include ethenyl, propenyl, n-butenyl, 3-methylbut-2-enyl, n-pentenyl, octenyl and decenyl. An alkenyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —$NH_2$, —NH(alkyl), —N(alkyl)$_2$, —NH(cycloalkyl), —O—C(O)-alkyl, —O—C(O)-aryl, —O—C(O)-cycloalkyl, —C(O)OH and —C(O)O-alkyl. The term "$C_2$-$C_6$ alkenyl" refers to an alkenyl group having from 2 to 6 carbon atoms. Unless otherwise indicated, an alkenyl group is unsubstituted.

The term "alkynyl," as used herein, refers to an aliphatic hydrocarbon group containing at least one carbon-carbon triple bond and having one of its hydrogen atoms replaced with a bond. An alkynyl group may be straight or branched and contain from about 2 to about 15 carbon atoms. In one embodiment, an alkynyl group contains from about 2 to about 12 carbon atoms. In another embodiment, an alkynyl group contains from about 2 to about 6 carbon atoms. Non-limiting examples of alkynyl groups include ethynyl, propynyl, 2-butynyl and 3-methylbutynyl. An alkynyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —$NH_2$, —NH(alkyl), —N(alkyl)$_2$, —NH(cycloalkyl), —O—C(O)-alkyl, —O—C(O)-aryl, —O—C(O)-cycloalkyl, —C(O)OH and —C(O)O-alkyl. The term "$C_2$-$C_6$ alkynyl" refers to an alkynyl group having from 2 to 6 carbon atoms. Unless otherwise indicated, an alkynyl group is unsubstituted.

The term "alkylene," as used herein, refers to an alkyl group, as defined above, wherein one of the alkyl group's hydrogen atoms has been replaced with a bond. Non-limiting examples of alkylene groups include —$CH_2$—, —$CH_2CH_2$—, —$CH_2CH_2CH_2$—, —$CH_2CH_2CH_2CH_2$—, —CH($CH_3$)$CH_2CH_2$—, —CH($CH_3$)— and —$CH_2$CH($CH_3$)$CH_2$—. In one embodiment, an alkylene group has from 1 to about 6 carbon atoms. In another embodiment, an alkylene group has from about 3 to about 5 carbon atoms. In another embodiment, an alkylene group is branched. In another embodiment, an alkylene group is linear. In one embodiment, an alkylene group is —$CH_2$—. The term "$C_1$-$C_6$ alkylene" refers to an alkylene group having from 1 to 6 carbon atoms. The term "$C_3$-$C_5$ alkylene" refers to an alkylene group having from 3 to 5 carbon atoms.

The term "alkenylene," as used herein, refers to an alkenyl group, as defined above, wherein one of the alkenyl group's hydrogen atoms has been replaced with a bond. Non-limiting examples of alkenylene groups include —CH=CH—, —CH=CHCH$_2$—, —CH$_2$CH=CH—, —CH$_2$CH=CHCH$_2$—, —CH=CHCH$_2$CH$_2$—, —CH$_2$CH$_2$CH=CH— and —CH(CH$_3$)CH=CH—. In one embodiment, an alkenylene group has from 2 to about 6 carbon atoms. In another embodiment, an alkenylene group has from about 2 to about 4 carbon atoms. In another embodiment, an alkenylene group is branched. In another embodiment, an alkenylene group is linear. The term "$C_2$-$C_6$ alkylene" refers to an alkenylene group having from 2 to 6 carbon atoms. The term "$C_2$-$C_4$ alkenylene" refers to an alkylene group having from 2 to 4 carbon atoms.

The term "aryl," as used herein, refers to an aromatic monocyclic or multicyclic ring system comprising from about 6 to about 14 carbon atoms. In one embodiment, an aryl group contains from about 6 to about 10 carbon atoms. An aryl group can be optionally substituted with one or more "ring system substituents" which may be the same or different, and are as defined herein below. In one embodiment, an aryl group can be optionally fused to a cycloalkyl or cycloalkanoyl group. Non-limiting examples of aryl groups include phenyl and naphthyl. In one embodiment, an aryl group is phenyl. Unless otherwise indicated, an aryl group is unsubstituted.

The term "arylene," as used herein, refers to a bivalent group derived from an aryl group, as defined above, by removal of a hydrogen atom from a ring carbon of an aryl group. An arylene group can be derived from a monocyclic or multicyclic ring system comprising from about 6 to about 14 carbon atoms. In one embodiment, an arylene group contains from about 6 to about 10 carbon atoms. In another embodiment, an arylene group is a naphthylene group. In another embodiment, an arylene group is a phenylene group. An arylene group can be optionally substituted with one or more "ring system substituents" which may be the same or different, and are as defined herein below. An arylene group is divalent and either available bond on an arylene group can connect to either group flanking the arylene group. For example, the group "A-arylene-B," wherein the arylene group is:

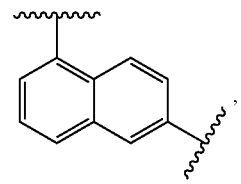 [SMILES: *c1ccc2c(*)cccc2c1]

is understood to represent both:

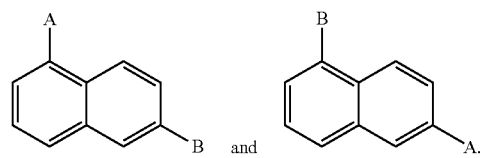

In one embodiment, an arylene group can be optionally fused to a cycloalkyl or cycloalkanoyl group. Non-limiting examples of arylene groups include phenylene and naphthalene. In one embodiment, an arylene group is unsubstituted. In another embodiment, an arylene group is:

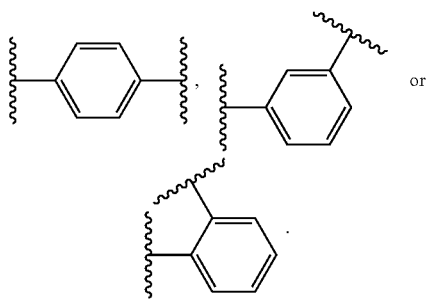

Unless otherwise indicated, an arylene group is unsubstituted.

The term "cycloalkyl," as used herein, refers to a non-aromatic mono- or multicyclic ring system comprising from about 3 to about 10 ring carbon atoms. In one embodiment, a cycloalkyl contains from about 5 to about 10 ring carbon atoms. In another embodiment, a cycloalkyl contains from about 3 to about 7 ring atoms. In another embodiment, a cycloalkyl contains from about 5 to about 6 ring atoms. The term "cycloalkyl" also encompasses a cycloalkyl group, as defined above, which is fused to an aryl (e.g., benzene) or heteroaryl ring. Non-limiting examples of monocyclic cycloalkyls include cyclopropyl, cyclobutyl, cyclopentyl, cyclohexyl, cycloheptyl and cyclooctyl. Non-limiting examples of multicyclic cycloalkyls include 1-decalinyl, norbornyl and adamantyl. A cycloalkyl group can be optionally substituted with one or more "ring system substituents" which may be the same or different, and are as defined herein below. In one embodiment, a cycloalkyl group is unsubstituted. The term "3 to 7-membered cycloalkyl" refers to a cycloalkyl group having from 3 to 7 ring carbon atoms. Unless otherwise indicated, a cycloalkyl group is unsubstituted. A ring carbon atom of a cycloalkyl group may be functionalized as a carbonyl group. An illustrative example of such a cycloalkyl group (also referred to herein as a "cycloalkanoyl" group) includes, but is not limited to, cyclobutanoyl:

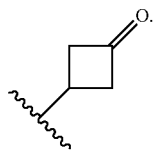 [SMILES: *C1CC(=O)C1]

The term "halo," as used herein, means —F, —Cl, —Br or —I.

The term "haloalkyl," as used herein, refers to an alkyl group as defined above, wherein one or more of the alkyl group's hydrogen atoms has been replaced with a halogen. In one embodiment, a haloalkyl group has from 1 to 6 carbon atoms. In another embodiment, a haloalkyl group is substituted with from 1 to 3 F atoms. Non-limiting examples of haloalkyl groups include —CH$_2$F, —CHF$_2$, —CF$_3$, —CH$_2$Cl and —CCl$_3$. The term "C$_1$-C$_6$ haloalkyl" refers to a haloalkyl group having from 1 to 6 carbon atoms.

The term "hydroxyalkyl," as used herein, refers to an alkyl group as defined above, wherein one or more of the alkyl group's hydrogen atoms have been replaced with an —OH group. In one embodiment, a hydroxyalkyl group has from 1 to 6 carbon atoms. Non-limiting examples of hydroxyalkyl groups include —CH$_2$OH, —CH$_2$CH$_2$OH, —CH$_2$CH$_2$CH$_2$OH and —CH$_2$CH(OH)CH$_3$. The term "C$_1$-C$_6$ hydroxyalkyl" refers to a hydroxyalkyl group having from 1 to 6 carbon atoms.

The term "heteroaryl," as used herein, refers to an aromatic monocyclic or multicyclic ring system comprising about 5 to about 14 ring atoms, wherein from 1 to 4 of the ring atoms is independently O, N or S and the remaining ring atoms are carbon atoms. In one embodiment, a heteroaryl group has 5 to 10 ring atoms. In another embodiment, a heteroaryl group is monocyclic and has 5 or 6 ring atoms. In another embodiment, a heteroaryl group is bicyclic. A heteroaryl group can be optionally substituted by one or more "ring system substituents" which may be the same or different, and are as defined herein below. A heteroaryl group is joined via a ring carbon atom, and any nitrogen atom of a heteroaryl can be optionally oxidized to the corresponding N-oxide. The term "heteroaryl" also encompasses a heteroaryl group, as defined above, which is fused to a benzene ring. Non-limiting examples of heteroaryls include pyridyl, pyrazinyl, furanyl, thienyl, pyrimidinyl, pyridone (including N-substituted pyridones), isoxazolyl, isothiazolyl, oxazolyl, oxadiazolyl, thiazolyl, pyrazolyl, furazanyl, pyrrolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, benzimidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like, and all isomeric forms thereof. The term "heteroaryl" also refers to partially saturated heteroaryl moieties such as, for example, tetrahydroisoquinolyl, tetrahydroquinolyl and the like. In one embodiment, a heteroaryl group is a 5-membered heteroaryl. In another embodiment, a heteroaryl group is a 6-membered monocyclic heteroaryl. In another embodiment, a heteroaryl group comprises a 5- to 6-membered monocyclic heteroaryl group fused to a benzene ring. Unless otherwise indicated, a heteroaryl group is unsubstituted.

The term "heterocycloalkyl," as used herein, refers to a non-aromatic saturated monocyclic or multicyclic ring system comprising 3 to about 11 ring atoms, wherein from 1 to 4 of the ring atoms are independently O, S, N or Si, and the remainder of the ring atoms are carbon atoms. A heterocycloalkyl group can be joined via a ring carbon, ring silicon atom or ring nitrogen atom. In one embodiment, a heterocycloalkyl group is monocyclic and has from about 3 to about 7 ring atoms. In another embodiment, a heterocycloalkyl group is monocyclic has from about 4 to about 7 ring atoms. In another embodiment, a heterocycloalkyl group is bicyclic and has from about 7 to about 11 ring atoms. In still another embodiment, a heterocycloalkyl group is monocyclic and has 5 or 6 ring atoms. In one embodiment, a heterocycloalkyl group is monocyclic. In another embodiment, a heterocycloalkyl group is bicyclic. There are no adjacent oxygen and/or sulfur atoms present in the ring system. Any —NH group in a heterocycloalkyl ring may exist protected such as, for example, as an —N(BOC), —N(Cbz), —N(Tos) group and the like; such protected heterocycloalkyl groups are considered part of this invention. The term "heterocycloalkyl" also encompasses a heterocycloalkyl group, as defined above, which is fused to an aryl (e.g., benzene) or heteroaryl ring. A heterocycloalkyl group can be optionally substituted by one or more "ring system substituents" which may be the same or different, and are as defined herein below. The nitrogen or sulfur atom of the heterocycloalkyl can be optionally oxidized to the corresponding N-oxide, S-oxide or S,S-dioxide. Non-limiting examples of monocyclic heterocycloalkyl rings include oxetanyl, piperidyl, pyrrolidinyl, piperazinyl, morpholinyl, thiomorpholinyl, thiazolidinyl, 1,4-dioxanyl, tetrahydrofuranyl, tetrahydrothiophenyl, delta-lactam, delta-lactone and the like, and all isomers thereof.

A ring carbon atom of a heterocycloalkyl group may be functionalized as a carbonyl group. An illustrative example of such a heterocycloalkyl group is:

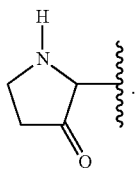 [SMILES: *C1NCCC1=O]

In one embodiment, a heterocycloalkyl group is a 5-membered monocyclic heterocycloalkyl. In another embodiment, a heterocycloalkyl group is a 6-membered monocyclic heterocycloalkyl. The term "3 to 6-membered monocyclic heterocycloalkyl" refers to a monocyclic heterocycloalkyl group having from 3 to 6 ring atoms. The term "4 to 7-membered monocyclic heterocycloalkyl" refers to a monocyclic heterocycloalkyl group having from 4 to 7 ring atoms. The term "7 to 11-membered bicyclic heterocycloalkyl" refers to a bicyclic heterocycloalkyl group having from 7 to 11 ring atoms. Unless otherwise indicated, a heterocycloalkyl group is unsubstituted.

The term "ring system substituent," as used herein, refers to a substituent group attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, -alkylene-aryl, -arylene-alkyl, -alkylene-heteroaryl, -alkenylene-heteroaryl, -alkynylene-heteroaryl, —OH, hydroxyalkyl, haloalkyl, —O-alkyl, —O-haloalkyl, -alkylene-O-alkyl, —O-aryl, —O-alkylene-aryl, acyl, —C(O)-aryl, halo, —NO$_2$, —CN, —SF$_5$, —C(O)OH, —C(O)O-alkyl, —C(O)O-aryl, —C(O)O-alkylene-aryl, —S(O)-alkyl, —S(O)$_2$-alkyl, —S(O)-aryl, —S(O)$_2$-aryl, —S(O)-heteroaryl, —S(O)$_2$-heteroaryl, —S-alkyl, —S-aryl, —S-heteroaryl, —S-alkylene-aryl, —S-alkylene-heteroaryl, —S(O)$_2$-alkylene-aryl, —S(O)$_2$-alkylene-heteroaryl, —Si(alkyl)$_2$, —Si(aryl)$_2$, —Si(heteroaryl)$_2$, —Si(alkyl)(aryl), —Si(alkyl)(cycloalkyl), —Si(alkyl)(heteroaryl), cycloalkyl, heterocycloalkyl, —O—C(O)-alkyl, —O—C(O)-aryl, —O—C(O)-cycloalkyl, —C(=N—CN)—NH$_2$, —C(=NH)—NH$_2$, —C(=NH)—NH(alkyl), —N(Y$_1$)(Y$_2$), -alkylene-N(Y$_1$)(Y$_2$), —C(O)N(Y$_1$)(Y$_2$) and —S(O)$_2$N(Y$_1$)(Y$_2$), wherein Y$_1$ and Y$_2$ can be the same or different and are independently selected from the group consisting of hydrogen, alkyl, aryl, cycloalkyl, and -alkylene-aryl. "Ring system substituent" may also mean a single moiety which simultaneously replaces two available hydrogens on two adjacent carbon atoms (one H on each carbon) on a ring system. Examples of such moiety are methylenedioxy, ethylenedioxy, —C(CH$_3$)$_2$— and the like which form moieties such as, for example:

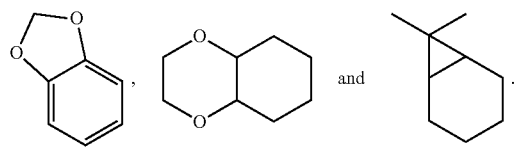

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "in substantially purified form," as used herein, refers to the physical state of a compound after the compound is isolated from a synthetic process (e.g., from a reaction mixture), a natural source, or a combination thereof. The term "in substantially purified form," also refers to the physical state of a compound after the compound is obtained from a purification process or processes described herein or well-known to the skilled artisan (e.g., chromatography, recrystallization and the like), in sufficient purity to be characterizable by standard analytical techniques described herein or well-known to the skilled artisan.

It should also be noted that any carbon as well as heteroatom with unsatisfied valences in the text, schemes, examples and tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in Organic Synthesis* (1991), Wiley, New York.

When any substituent or variable (e.g., alkyl, $R^1$, $R^7$, etc.) occurs more than one time in any constituent or in Formula (I), its definition on each occurrence is independent of its definition at every other occurrence, unless otherwise indicated.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g., a drug precursor) that is transformed in vivo to provide a Fused Tricyclic Heterocycle Derivative or a pharmaceutically acceptable salt of the compound. The transformation may occur by various mechanisms (e.g., by metabolic or chemical processes), such as, for example, through hydrolysis in blood. For example, if a Fused Tricyclic Heterocycle Derivative or a pharmaceutically acceptable salt, hydrate or solvate of the compound contains a carboxylic acid functional group, a prodrug can comprise an ester formed by the replacement of the hydrogen atom of the acid group with a group such as, for example, $(C_1-C_8)$alkyl, $(C_2-C_{12})$alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—$(C_1-C_2)$alkylamino$(C_2-C_3)$alkyl (such as β-dimethylaminoethyl), carbamoyl-$(C_1-C_2)$alkyl, N,N-di $(C_1-C_2)$alkylcarbamoyl-$(C_1-C_2)$alkyl and piperidino-, pyrrolidino- or morpholino$(C_2-C_3)$alkyl, and the like.

Similarly, if a Fused Tricyclic Heterocycle Derivative contains an alcohol functional group, a prodrug can be formed by the replacement of one or more of the hydrogen atoms of the alcohol groups with a group such as, for example, $(C_1-C_6)$alkanoyloxymethyl, 1-(($C_1-C_6$)alkanoyloxy)ethyl, 1-methyl-1-(($C_1-C_6$)alkanoyloxy)ethyl, $(C_1-C_6)$ alkoxycarbonyloxymethyl, N—$(C_1-C_6)$alkoxycarbonylaminomethyl, succinoyl, $(C_1-C_6)$alkanoyl, α-amino$(C_1-C_4)$ alkyl, α-amino$(C_1-C_4)$alkylene-aryl, arylacyl and α-aminoacyl, or α-aminoacyl-α-aminoacyl, where each α-aminoacyl group is independently selected from the naturally occurring L-amino acids, or glycosyl (the radical resulting from the removal of a hydroxyl group of the hemiacetal form of a carbohydrate).

If a Fused Tricyclic Heterocycle Derivative incorporates an amine functional group, a prodrug can be formed by the replacement of a hydrogen atom in the amine group with a group such as, for example, R-carbonyl-, RO-carbonyl-, NRR'-carbonyl- wherein R and R' are each independently $(C_1-C_{10})$alkyl, $(C_3-C_7)$ cycloalkyl, benzyl, a natural α-aminoacyl, —C(OH)C(O)OY$^1$ wherein Y$^1$ is H, $(C_1-C_6)$ alkyl or benzyl, —C(OY$^2$)Y$^3$ wherein Y$^2$ is $(C_1-C_4)$ alkyl and Y$^3$ is $(C_1-C_6)$alkyl; carboxy $(C_1-C_6)$alkyl; amino$(C_1-C_4)$alkyl or mono-N- or di-N,N—$(C_1-C_6)$alkylaminoalkyl; —C(Y$^4$)Y$^5$ wherein Y$^4$ is H or methyl and Y$^5$ is mono-N- or di-N,N—$(C_1-C_6)$alkylamino morpholino; piperidin-1-yl or pyrrolidin-1-yl, and the like.

Pharmaceutically acceptable esters of the present compounds include the following groups: (1) carboxylic acid esters obtained by esterification of the hydroxy group of a hydroxyl compound, in which the non-carbonyl moiety of the carboxylic acid portion of the ester grouping is selected from straight or branched chain alkyl (e.g., methyl, ethyl, n-propyl, isopropyl, t-butyl, sec-butyl or n-butyl), alkoxyalkyl (e.g., methoxymethyl), aralkyl (e.g., benzyl), aryloxyalkyl (for example, phenoxymethyl), aryl (e.g., phenyl optionally substituted with, for example, halogen, $C_{1-4}$alkyl, —O—($C_{1-4}$alkyl) or amino); (2) sulfonate esters, such as alkyl- or aralkylsulfonyl (for example, methanesulfonyl); (3) amino acid esters, including those corresponding to both natural and non-natural amino acids (e.g., L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di ($C_{6-24}$)acyl glycerol.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of solvates include ethanolates, methanolates, and the like. A "hydrate" is a solvate wherein the solvent molecule is water.

One or more compounds of the invention may optionally be converted to a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS Pharm Sci Techours.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than room temperature, and cooling the solution at a rate sufficient to form crystals which are then isolated by standard methods. Analytical techniques such as, for example IR spectroscopy, show the presence of the solvent (or water) in the crystals as a solvate (or hydrate).

The Fused Tricyclic Heterocycle Derivatives can form salts which are also within the scope of this invention. Reference to a Fused Tricyclic Heterocycle Derivative herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a Fused Tricyclic Heterocycle Derivative contains both a basic moiety, such as, but not limited to a pyridine or imidazole, and an acidic moiety, such as, but not limited to a carboxylic acid, zwitterions ("inner salts") may be formed and are included within the term "salt(s)" as used herein. In one embodiment, the salt is a pharmaceutically acceptable (i.e., non-toxic, physiologically acceptable) salt. In another embodiment, the salt is other than a pharmaceutically acceptable salt. Salts of the Compounds of Formula (I) may be formed, for example, by reacting a Fused Tricyclic Heterocycle Derivative with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamine, t-butyl amine, choline, and salts with amino acids such as arginine, lysine and the like. Basic nitrogen-containing groups may be quarternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Diastereomeric mixtures can be separated into their individual diastereomers on the basis of their physical chemical differences by methods well-known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Sterochemically pure compounds may also be prepared by using chiral starting materials or by employing salt resolution techniques. Also, some of the Fused Tricyclic Heterocycle Derivatives may be atropisomers (e.g., substituted biaryls) and are considered as part of this invention. Enantiomers can also be directly separated using chiral chromatographic techniques.

It is also possible that the Fused Tricyclic Heterocycle Derivatives may exist in different tautomeric forms, and all such forms are embraced within the scope of the invention. For example, all keto-enol and imine-enamine forms of the compounds are included in the invention.

All stereoisomers (for example, geometric isomers, optical isomers and the like) of the present compounds (including those of the salts, solvates, hydrates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. If a Fused Tricyclic Heterocycle Derivative incorporates a double bond or a fused ring, both the cis- and trans-forms, as well as mixtures, are embraced within the scope of the invention.

Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate", "ester", "prodrug" and the like, is intended to apply equally to the salt, solvate, ester and prodrug of enantiomers, stereoisomers, rotamers, tautomers, positional isomers, racemates or prodrugs of the inventive compounds.

Recitation or depiction of a specific compound in the claims (i.e., a species) without a specific stereoconfiguration designation, or with such a designation for less than all chiral centers, is intended to encompass the racemate, racemic mixtures, each individual enantiomer, a diastereoisomeric mixture and each individual diastereomer of the compound where such forms are possible due to the presence of one or more asymmetric centers.

In the Compounds of Formula (I), the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1H$) and deuterium ($^2H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched Compounds of Formula (I) can be prepared without undue experimentation by conventional techniques well known to those skilled in the art or by processes analogous to those described in the Schemes and Examples herein using appropriate isotopically-enriched reagents and/or intermediates. In one embodiment, a Compound of Formula (I) has one or more of its hydrogen atoms replaced with deuterium.

Polymorphic forms of the Fused Tricyclic Heterocycle Derivatives, and of the salts, solvates, hydrates, esters and prodrugs of the Fused Tricyclic Heterocycle Derivatives, are intended to be included in the present invention.

General List of Abbreviations

AcOH=acetic acid
Alk=alkyl
Ar=aryl
Boc=tert-butoxycarbonyl
br=broad
d=doublet
DCE=1,2-dichloroethane
DEA=N,N-diethylamine
DHP=dihydropyran
DIEA=N,N-diisopropylethylamine
DMA=N,N-dimethylacetamide
DMF=dimethylformamide
DMSO=dimethyl sulfoxide
EDC=1-ethyl-3-(3'-dimethylaminopropyl)carbodiimide hydrochloride
ESI=electrospray ionization
EtOAc=ethyl acetate
EtOH=ethanol
HATU=2-(1H-7-Azabenzotriazol-1-yl)-1,1,3,3-tetramethyl uronium hexafluorophosphate
HOAt=1-hydroxy-7-azabenzotriazole
HOBt=1-hydroxybenzotriazole
HRMS=high resolution mass spectrometry
LCMS=liquid chromatography/mass sepectrometry
LiHMDS=lithium bis(trimethylsilyl)amide
LRMS=low resolution mass spectrometry
m=multiplet
mCPBA=meta-chloroperoxybenzoic acid
min=minutes
MS=mass spectroscopy
NMR=nuclear magnetic resonance spectroscopy
Piv=pivalate, 2,2-dimethylpropanoyl Ph=phenyl
s=singlet
SFC=supercritical fluid chromatography
t=triplet
TEA=triethylamine
TFA=trifluoroacetic acid
THF=tetrahydrofuran
wt %=weight percent The Compounds of Formula (I)

The present invention provides Fused Tricyclic Heterocycle Derivatives of Formula (I):

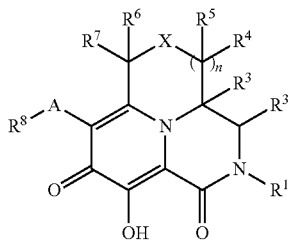

(I)

and pharmaceutically acceptable salts thereof, wherein $R^1$-$R^8$, n, A and X are defined above for the Compounds of Formula (I).

In one embodiment, the Compounds of Formula (I) have Formula (Ia'):

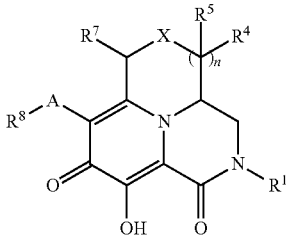

(Ia')

and pharmaceutically acceptable salts thereof,
wherein:

A is $C_1$-$C_1$ alkylene, $C_2$-$C_4$ alkenylene, arylene, $C_3$-$C_7$ cycloalkyl, 5 or 6-membered monocyclic heteroaryl, 4 to 7-membered heterocycloalkyl, —O—, —NH—C(O)—, —C(O)NH— or —C(O)—;

X is O, —N($C_1$-$C_6$ alkyl)- or —CH$_2$, such that when X=O or —N($C_1$-$C_6$ alkyl)-, then $R^4$, $R^5$, $R^6$ and $R^7$ are each other than —OR$^9$, —N(R$^9$)$_2$ or halo;

n is 0 or 1;

$R^1$ is $C_1$-$C_6$ alkyl, which is optionally substituted with up to 3 groups, each independently selected from $C_3$-$C_7$ cycloalkyl, 5 or 6-membered monocyclic heteroaryl, 4 to 6-membered monocyclic heterocycloalkyl, $C_6$-$C_{10}$ aryl, halo, $C_1$-$C_6$ haloalkyl, —OR$^{11}$, —N(R$^{11}$)$_2$, —C(O)R$^{11}$, —C(O)N(R$^{11}$)$_2$, —NHC(O)R$^{11}$ and —SR$^{11}$, wherein said $C_3$-$C_7$ cycloalkyl group, said 5 or 6-membered monocyclic heteroaryl group, said 4 to 6-membered monocyclic heterocycloalkyl group and said $C_6$-$C_{10}$ aryl group can each be optionally and independently substituted with one or more groups, each independently selected from $C_1$-$C_6$ alkyl, $C_3$-$C_7$ cycloalkyl, 5 or 6-membered monocyclic heteroaryl, 4 to 6-membered monocyclic heterocycloalkyl, $C_6$-$C_{10}$ aryl, halo, $C_1$-$C_6$ haloalkyl, —OR$^9$, —N(R$^9$)$_2$, —C(O)R$^9$, —C(O)N(R$^9$)$_2$, —NHC(O)R$^9$ and —SR$^9$;

$R^2$, $R^5$, $R^6$ and $R^7$ are each independently selected from H, $C_1$-$C_6$ alkyl, $C_3$-$C_7$ cycloalkyl, halo, $C_1$-$C_6$ haloalkyl, —OR$^9$, —N(R$^9$)$_2$, —C(O)R$^9$, —C(O)N(R$^9$)$_2$ and —NHC(O)R$^9$, wherein said $C_1$-$C_6$ alkyl group can be optionally substituted with one or more groups, each independently selected from halo, —OH, —O($C_1$-$C_6$ alkyl), —NH$_2$, —NH($C_1$-$C_6$ alkyl), —N($C_1$-$C_6$ alkyl)$_2$, —SH or —S($C_1$-$C_6$ alkyl);

$R^3$ is H, $C_1$-$C_6$ alkyl, $C_3$-$C_7$ cycloalkyl, $C_1$-$C_6$ haloalkyl, —C(O)R$^9$, —C(O)N(R$^9$)$_2$ and —NHC(O)R$^9$, wherein said $C_1$-$C_6$ alkyl group can be optionally substituted with one or more groups, each independently selected from halo, —OH, —O($C_1$-$C_6$ alkyl), —NH$_2$, —NH($C_1$-$C_6$ alkyl), —N($C_1$-$C_6$ alkyl)$_2$, —SH or —S($C_1$-$C_6$ alkyl);

$R^4$ is H, or $R^4$ and $R^5$ and the common carbon atom to which they are attached, join to form an endocyclic —C(O)— group;

$R^8$ is selected from $C_1$-$C_6$ alkyl, —($C_1$-$C_3$ alkylene)$_n$-($C_3$-$C_7$ cycloalkyl), —($C_1$-$C_3$ alkylene)$_n$-(5 or 6-membered monocyclic heteroaryl), —($C_1$-$C_3$ alkylene)$_n$-(4 to 6-membered monocyclic heterocycloalkyl) and —($C_1$-$C_3$ alkylene)$_n$-($C_6$-$C_{10}$ aryl), wherein said $C_3$-$C_7$ cycloalkyl group, said 5 or 6-membered monocyclic heteroaryl group, said 4 to 6-membered monocyclic heterocycloalkyl group and said $C_6$-$C_{10}$ aryl group can each be optionally and independently substituted with up to 5 groups, each independently selected from $C_1$-$C_6$ alkyl, $C_3$-$C_7$ cycloalkyl, 5 or 6-membered monocyclic heteroaryl, 4 to 6-membered monocyclic heterocycloalkyl, $C_6$-$C_{10}$ aryl, halo, $C_1$-$C_6$ haloalkyl, —OR$^9$, —N(R$^9$)$_2$, —C(O)R$^9$, —C(O)N(R$^9$)$_2$, —NHC(O)R$^9$ and —SR$^9$; and each occurrence of R$^9$ is independently selected from H, $C_1$-$C_6$ alkyl, $C_3$-$C_7$ cycloalkyl, $C_6$-$C_{10}$ aryl and benzyl.

In one embodiment, the Compounds of Formula (I) have Formula (Ia):

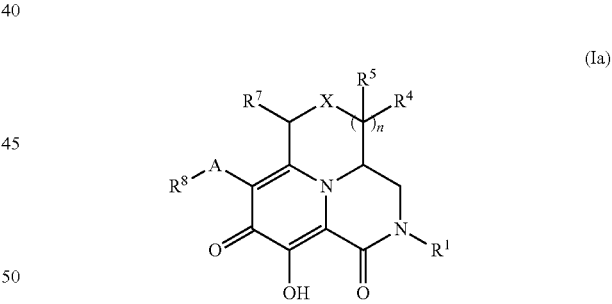

(Ia)

and pharmaceutically acceptable salts thereof,
wherein:

A is 5 or 6-membered monocyclic heteroaryl or —NH—C(O)—;

X is O, —N($C_1$-$C_6$ alkyl)- or —C(R$^{10}$)(R$^{11}$), such that when X=O or —N($C_1$-$C_6$ alkyl)-, then $R^4$, $R^5$, $R^6$ and $R^7$ are each other than —OR$^9$, —N(R$^9$)$_2$ or halo;

n is 0 or 1, such that when n is 0, then $R^4$ and $R^5$ are not present;

$R^1$ is $C_1$-$C_6$ alkyl, which is optionally substituted with a group selected from phenyl, $C_3$-$C_7$ cycloalkyl, 5 or 6-membered monocyclic heteroaryl and —OR$^9$, wherein said phenyl group and said 5 or 6-membered monocyclic heteroaryl group can each be optionally and independently substituted with up to two groups, each independently selected from $C_1$-$C_6$ alkyl, $C_3$-$C_7$ cycloalkyl, 5 or 6-membered monocyclic heteroaryl, 4 to 6-membered monocyclic heterocycloalkyl, $C_6$-$C_{10}$ aryl, halo, $C_1$-$C_6$ haloalkyl, —$OR^9$, —$N(R^9)_2$, —$C(O)R^9$, —$C(O)N(R^9)_2$, —$NHC(O)R^9$ and —$SR^9$;

$R^4$ is H, or $R^4$ and $R^5$ and the common carbon atom to which they are attached, join to form an endocyclic —C(O)— group;

$R^5$, $R^{10}$ and $R^{11}$ are each independently selected from H, $C_1$-$C_6$ alkyl and —$OR^9$;

$R^7$ is selected from H, $C_1$-$C_6$ alkyl, —$OR^9$ and —OH;

$R^8$ is selected from $C_1$-$C_6$ alkyl or benzyl, wherein the phenyl moiety of said benzyl group can be optionally and independently substituted with up to 3 groups, each independently selected from $C_1$-$C_6$ alkyl, $C_3$-$C_7$ cycloalkyl, 5 or 6-membered monocyclic heteroaryl, 4 to 6-membered monocyclic heterocycloalkyl, $C_6$-$C_{10}$ aryl, halo, $C_1$-$C_6$ haloalkyl, —$OR^9$, —$N(R^9)_2$, —$C(O)R^9$, —$C(O)N(R^9)_2$, —$NHC(O)R^9$ and —$SR^9$; and each occurrence of $R^9$ is independently selected from H, $C_1$-$C_6$ alkyl, $C_3$-$C_7$ cycloalkyl, $C_6$-$C_{10}$ aryl and benzyl.

In one embodiment, the Compounds of Formula (I) have Formula (Ib):

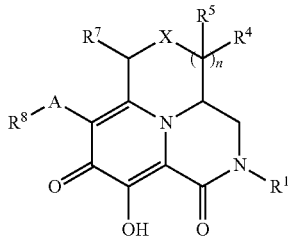

(Ib)

and pharmaceutically acceptable salts and prodrugs thereof, wherein:

A is pyrazolyl, thiadiazolyl, triazolyl, thiazolyl, oxazolyl, oxadiazolyl or —NHC(O)—;

X is O, —$N(C_1$-$C_6$ alkyl)- or —$C(R^{10})(R^{11})$, such that when X=O or —$N(C_1$-$C_6$ alkyl)-, then $R^4$, $R^5$, $R^6$ and $R^7$ are each other than —$OR^9$, —$N(R^9)_2$ or halo;

n is 0 or 1, such that when n is 0, then $R^4$ and $R^5$ are not present;

$R^1$ is $C_1$-$C_6$ alkyl, which is optionally substituted with a group selected from phenyl, $C_3$-$C_7$ cycloalkyl, 5 or 6-membered monocyclic heteroaryl and —O—($C_1$-$C_6$ alkyl), wherein said phenyl group and said 5 or 6-membered monocyclic heteroaryl group can each be optionally and independently substituted with up to two groups, each independently selected from $C_1$-$C_6$ alkyl, halo and —O—($C_1$-$C_6$ alkyl);

$R^4$ is H, or $R^4$ and $R^5$ and the common carbon atom to which they are attached, join to form an endocyclic —C(O)— group;

$R^5$, $R^{10}$ and $R^{11}$ are each independently selected from H, $C_1$-$C_6$ alkyl and —O—($C_1$-$C_6$ alkyl);

$R^7$ is selected from H, $C_1$-$C_6$ alkyl, —O—($C_1$-$C_6$ alkyl) and —OH;

$R^8$ is selected from $C_1$-$C_6$ alkyl or benzyl, wherein the phenyl moiety of said benzyl group can be optionally and independently substituted with up to 3 groups, each independently selected from $C_1$-$C_6$ alkyl, —O—($C_1$-$C_6$ alkyl) and halo; and each occurrence of $R^9$ is independently selected from H, $C_1$-$C_6$ alkyl, $C_3$-$C_7$ cycloalkyl, $C_6$-$C_{10}$ aryl and benzyl.

In one embodiment, A is —NH—C(O)—.

In another embodiment, A is 5-membered heteroaryl.

In another embodiment, A is pyrazolyl, thiadiazolyl, triazolyl, thiazolyl, oxazolyl, oxadiazolyl or —NHC(O)—.

In still another embodiment, A is pyrazolyl, thiadiazolyl, triazolyl, thiazolyl, oxazolyl or oxadiazolyl.

In another embodiment, A is pyrazolyl, thiadiazolyl or —NHC(O)—.

In a further embodiment, A is thiadiazolyl.

In another embodiment, A is pyrazolyl.

In one embodiment, X is O.

In another embodiment, X is —$N(C_1$-$C_6$ alkyl)-.

In another embodiment, X is —$CH_2$—.

In one embodiment, $R^1$ is $C_1$-$C_6$ alkyl, which is optionally substituted with a group selected from phenyl, $C_3$-$C_7$ cycloalkyl, 5 or 6-membered monocyclic heteroaryl and —O—($C_1$-$C_6$ alkyl), wherein said phenyl group and said 5 or 6-membered monocyclic heteroaryl group can each be optionally and independently substituted with up to two groups, each independently selected from $C_1$-$C_6$ alkyl, halo and —O—($C_1$-$C_6$ alkyl).

In another embodiment, $R^1$ is $C_1$-$C_6$ alkyl, which is optionally substituted with a group selected from cyclopropyl, phenyl, pyridyl and methoxy, wherein said phenyl group and said 5 or 6-membered monocyclic heteroaryl group can each be optionally and independently substituted with up to 5 groups, each independently selected from methoxy, $C_1$-$C_6$ alkyl and fluoro.

In another embodiment, $R^1$ is $C_1$-$C_6$ alkyl.

In another embodiment, $R^1$ is —($C_1$-$C_6$ alkyl)-($C_3$-$C_7$ cycloalkyl).

In still another embodiment, $R^1$ is ethyl.

In another embodiment, $R^1$ is isopropyl.

In another embodiment, $R^1$ is selected from methyl, ethyl, isopropyl, isobutyl, —$CH_2CH_2OCH_3$, —$CH(CH_3)CH_2CH_2OCH_3$, para-fluorobenzyl, —$CH_2$-cyclopropyl and —$CH_2$-pyridyl.

In one embodiment, $R^2$ is H.

In one embodiment, $R^3$ is H.

In another embodiment, $R^2$ and $R^3$ are each H.

In one embodiment, $R^4$ is H.

In another embodiment, $R^2$, $R^3$ and $R^4$ are each H.

In one embodiment, $R^5$ is H.

In another embodiment, $R^2$, $R^3$, $R^4$ and $R^5$ are each H.

In one embodiment, $R^6$ is H.

In another embodiment, $R^6$ is —OH.

In one embodiment, $R^7$ is H.

In another embodiment, $R^7$ is —OH.

In another embodiment, $R^7$ is —O—($C_1$-$C_6$ alkyl).

In still another embodiment, $R^7$ is methoxy.

In one embodiment, $R^2$, $R^3$, $R^4$, $R^5$ and $R^6$ are each H and $R^7$ is H, methoxy or —OH.

In another embodiment, $R^2$, $R^3$, $R^4$, $R^5$ and $R^6$ are each H and $R^7$ is methoxy.

In another embodiment, $R^2$, $R^3$, $R^4$, $R^5$ and $R^6$ are each H, n is 0, and $R^7$ is methoxy.

In one embodiment, $R^1$ is $C_1$-$C_6$ alkyl; $R^2$, $R^3$, $R^4$, $R^5$ and $R^6$ are each H; and $R^7$ is H, methoxy or —OH.

In another embodiment, $R^1$ is ethyl; $R^2$, $R^3$, $R^4$, $R^5$ and $R^6$ are each H; and $R^7$ is methoxy.

In one embodiment, $R^8$ is benzyl, wherein the phenyl moiety of said benzyl group can be optionally and independently substituted with up to 3 groups, each independently selected from —$OR^{11}$, $C_1$-$C_6$ alkyl and halo.

In another embodiment, $R^8$ is benzyl, wherein the phenyl moiety of said benzyl group can be optionally and independently substituted with up to 3 groups, each independently selected from F, Cl and methyl.

In another embodiment, $R^8$ is selected from:

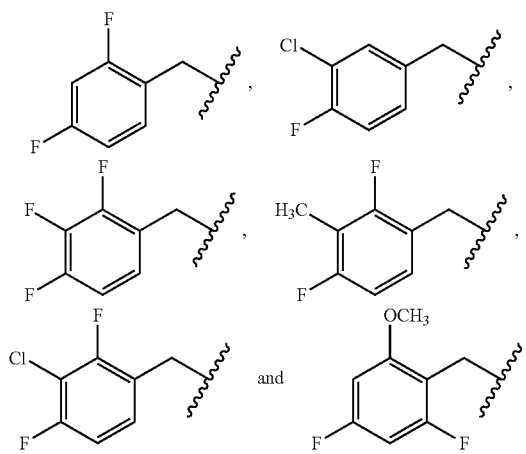

In still another embodiment, $R^8$ is $C_1$-$C_6$ alkyl.

In another embodiment, $R^8$ is methyl.

In one embodiment, X is —CH—; n is 0; and $R^7$ is H, methoxy or —OH.

In another embodiment, X is —O—; n is 1; and $R^4$, $R^5$ and $R^7$ are each H.

In one embodiment, (i) $R^1$ is $C_1$-$C_6$ alkyl, which is optionally substituted with a group selected from $C_3$-$C_7$ cycloalkyl, phenyl, 5 or 6-membered monocyclic heteroaryl and —O—($C_1$-$C_6$ alkyl), wherein said phenyl group and said 5 or 6-membered monocyclic heteroaryl group can each be optionally and independently substituted with up to two groups, each independently selected from $C_1$-$C_6$ alkyl, halo and —O—($C_1$-$C_6$ alkyl), and (ii) $R^8$ is benzyl, wherein the phenyl moiety of said benzyl group can be optionally and independently substituted with up to 3 groups, each independently selected from —$OR^{11}$, $C_1$-$C_6$ alkyl and halo.

In another embodiment, (i) $R^1$ is selected from methyl, ethyl, isopropyl, isobutyl, —$CH_2CH_2OCH_3$, —$CH(CH_3)CH_2CH_2OCH_3$, para-fluorobenzyl —$CH_2$-cyclopropyl and —$CH_2$-pyridyl, and (ii) $R^8$ is selected from:

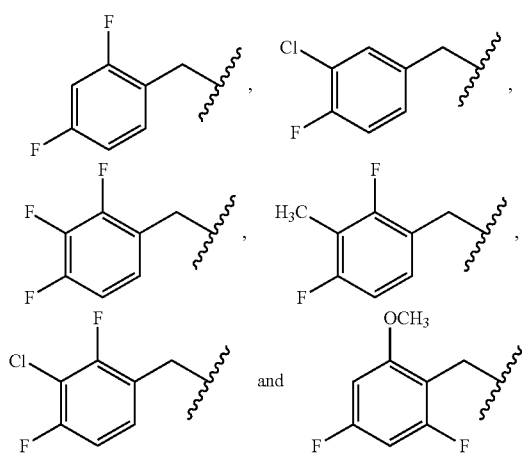

In one embodiment, the Compounds of Formula (I) have Formula (Id):

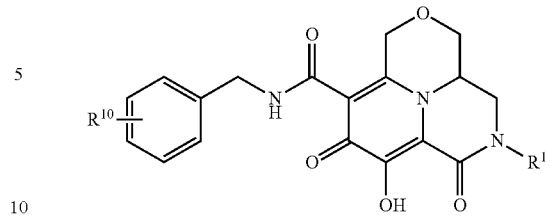

and pharmaceutically acceptable salts and prodrugs thereof, wherein:

$R^1$ is $C_1$-$C_6$ alkyl; and
$R^{10}$ represents up to 3 phenyl group substituents, each independently selected from $C_1$-$C_6$ alkyl, —O—($C_1$-$C_6$ alkyl) and halo.

In one embodiment, the Compounds of Formula (I) have Formula (Ie):

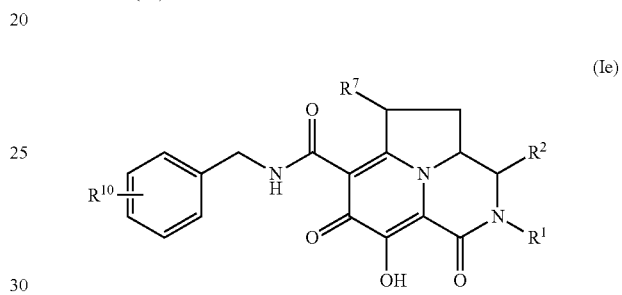

and pharmaceutically acceptable salts and prodrugs thereof, wherein:

$R^1$ is $C_1$-$C_6$ alkyl, which is optionally substituted with $C_3$-$C_7$ cycloalkyl, —O—($C_1$-$C_6$ alkyl), $C_1$-$C_6$ haloalkyl or phenyl, wherein said phenyl substituent is optionally substituted with halo;
$R^2$ is H or —O—($C_1$-$C_6$ alkyl);
$R^7$ is H, $C_1$-$C_6$ alkyl or —O—($C_1$-$C_6$ alkyl); and
$R^{10}$ represents up to 3 phenyl group substituents, each independently selected from $C_1$-$C_6$ alkyl, —O—($C_1$-$C_6$ alkyl) and halo.

In one embodiment, for the Compounds of Formula (Ie), $R^1$ is $C_1$-$C_6$ alkyl.

In another embodiment, for the Compounds of Formula (Ie), $R^1$ is methyl.

In another embodiment, for the Compounds of Formula (Ie), $R^1$ is ethyl.

In another embodiment, for the Compounds of Formula (Ie), $R^1$ is isopropyl.

In one embodiment, for the Compounds of Formula (Ie), $R^2$ is H.

In one embodiment, for the Compounds of Formula (Ie), $R^7$ is H.

In another embodiment, for the Compounds of Formula (Ie), $R^7$ is $C_1$-$C_6$ alkyl.

In another embodiment, for the Compounds of Formula (Ie), $R^7$ is —O—($C_1$-$C_6$ alkyl).

In another embodiment, for the Compounds of Formula (Ie), $R^7$ is methoxy.

In still another embodiment, for the Compounds of Formula (Ie), $R^1$ is ethoxy.

In one embodiment, for the Compounds of Formula (Ie), each occurrence of $R^{10}$ is halo.

In one embodiment, for the Compounds of Formula (Ie), $R^1$ is $C_1$-$C_6$ alkyl; $R^2$ is H, $R^7$ is —O—($C_1$-$C_6$ alkyl); and each occurrence of $R^{10}$ is halo.

In one embodiment, variables $R^1$-$R^{11}$, n, A and X for the Compounds of Formula (I) are selected independently of each other.
In another embodiment, the Compounds of Formula (I) are in substantially purified form.
In one embodiment, the present invention provides the following Compounds of Formula (I):
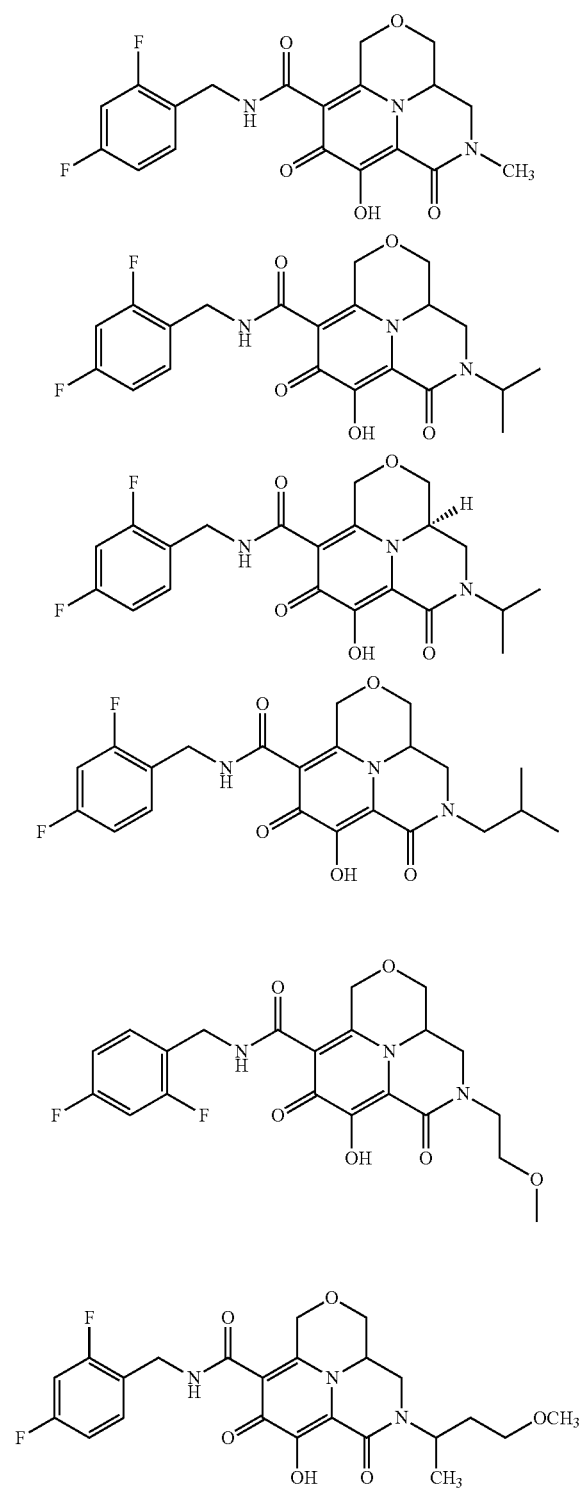
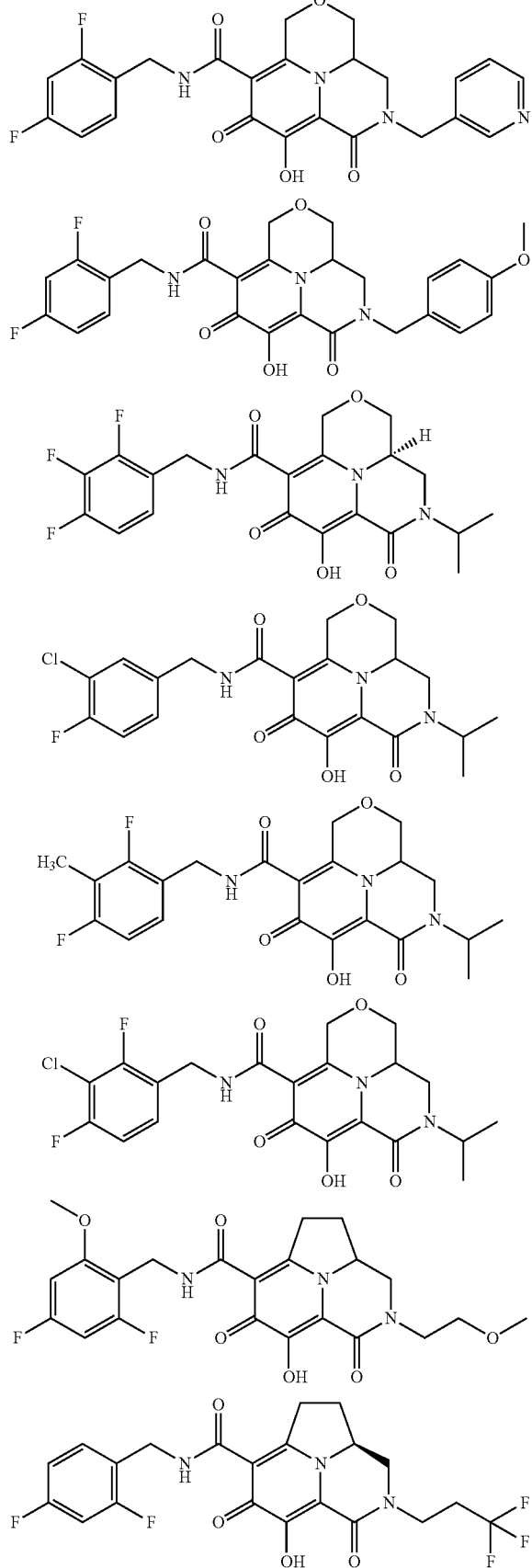

-continued
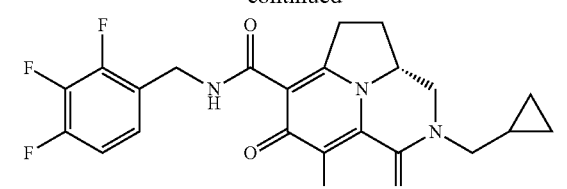
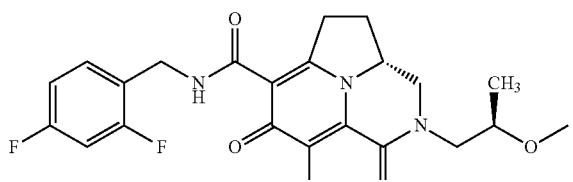
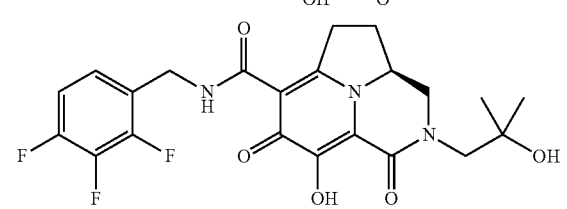
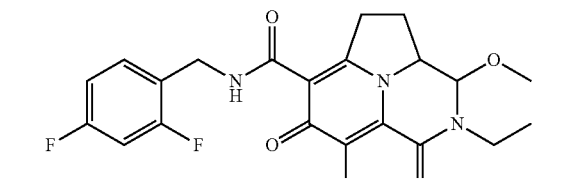
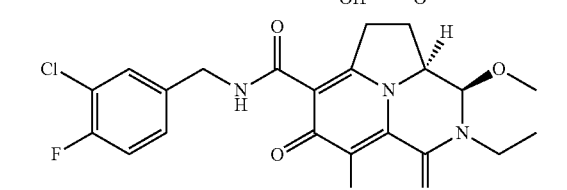
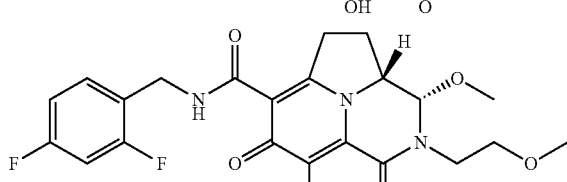
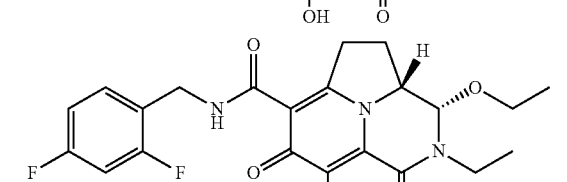
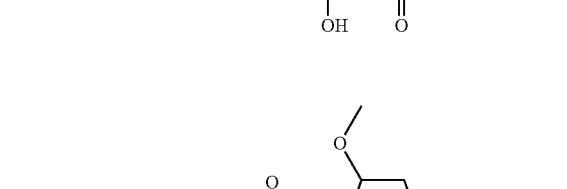
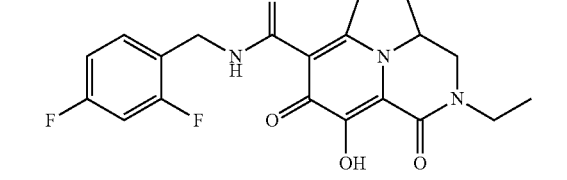
-continued
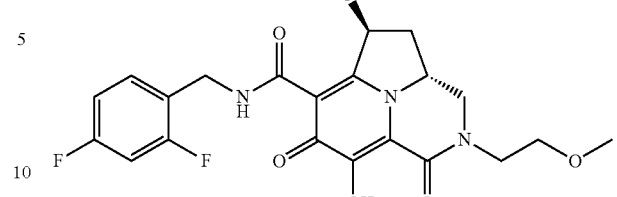
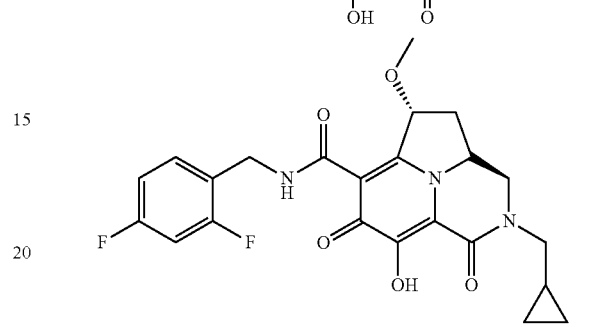
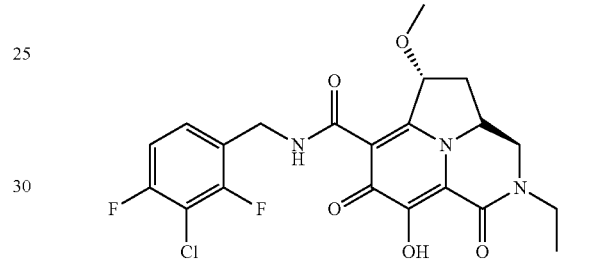
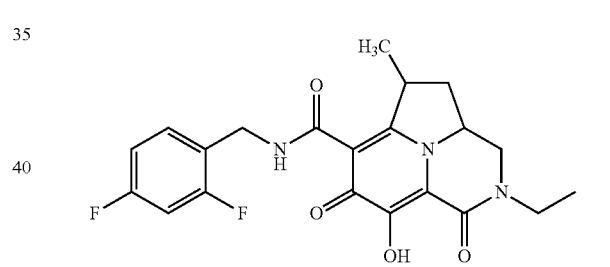
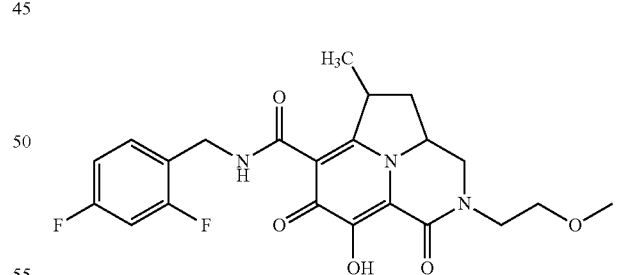
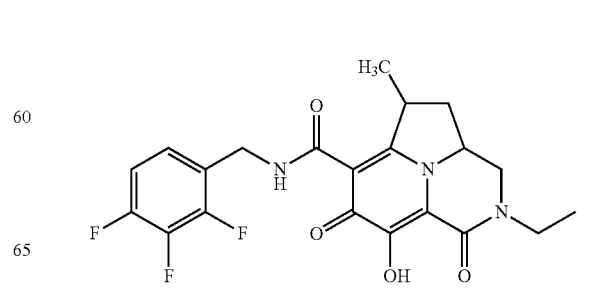

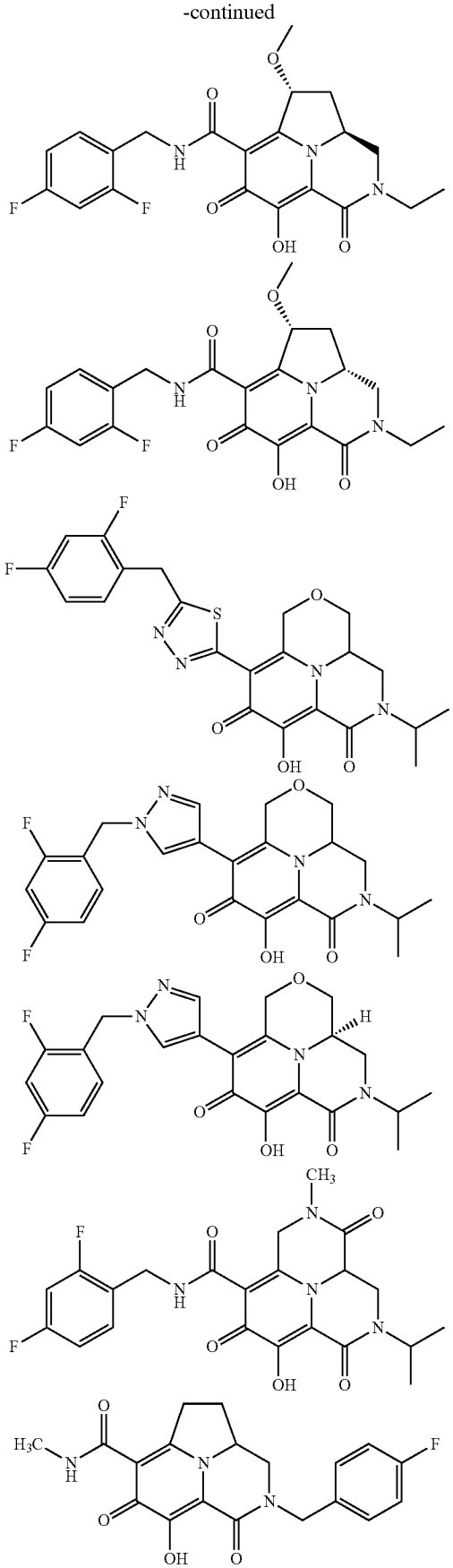
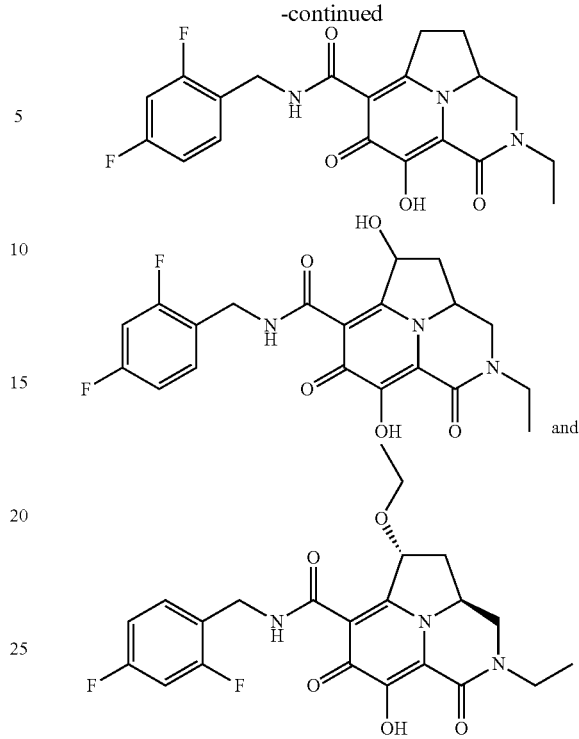

or a pharmaceutically acceptable salt thereof.

Other embodiments of the present invention include the following:

(a) A pharmaceutical composition comprising an effective amount of a Compound of Formula (I) or a pharmaceutically acceptable salt thereof, and a pharmaceutically acceptable carrier.

(b) The pharmaceutical composition of (a), further comprising a second therapeutic agent selected from the group consisting of HIV antiviral agents, immunomodulators, and anti-infective agents.

(c) The pharmaceutical composition of (b), wherein the HIV antiviral agent is an antiviral selected from the group consisting of HIV protease inhibitors, HIV integrase inhibitors, nucleoside reverse transcriptase inhibitors, CCR5 co-receptor antagonists and non-nucleoside reverse-transcriptase inhibitors.

(d) A pharmaceutical combination that is (i) a Compound of Formula (I) and (ii) a second therapeutic agent selected from the group consisting of HIV antiviral agents, immunomodulators, and anti-infective agents; wherein the Compound of Formula (I) and the second therapeutic agent are each employed in an amount that renders the combination effective for inhibiting HIV replication, or for treating HIV infection and/or reducing the likelihood or severity of symptoms of HIV infection.

(e) The combination of (d), wherein the HIV antiviral agent is an antiviral selected from the group consisting of HIV protease inhibitors, HIV integrase inhibitors, nucleoside reverse transcriptase inhibitors, CCR5 co-receptor antagonists and non-nucleoside reverse-transcriptase inhibitors.

(f) A method of inhibiting HIV replication in a subject in need thereof which comprises administering to the subject an effective amount of a Compound of Formula (I).

(g) A method of treating HIV infection and/or reducing the likelihood or severity of symptoms of HIV infection in a subject in need thereof which comprises administering to the subject an effective amount of a Compound of Formula (I).

(h) The method of (g), wherein the Compound of Formula (I) is administered in combination with an effective amount of at least one second therapeutic agent selected from the group consisting of HIV antiviral agents, immunomodulators, and anti-infective agents.

(i) The method of (h), wherein the HIV antiviral agent is an antiviral selected from the group consisting of HIV protease inhibitors, HIV integrase inhibitors, nucleoside reverse transcriptase inhibitors, CCR5 co-receptor antagonists and non-nucleoside reverse-transcriptase inhibitors.

(j) A method of inhibiting HIV replication in a subject in need thereof which comprises administering to the subject the pharmaceutical composition of (a), (b) or (c) or the combination of (d) or (e).

(k) A method of treating HIV infection and/or reducing the likelihood or severity of symptoms of HIV infection in a subject in need thereof which comprises administering to the subject the pharmaceutical composition of (a), (b) or (c) or the combination of (d) or (e).

The present invention also includes a compound of the present invention for use (i) in, (ii) as a medicament for, or (iii) in the preparation of a medicament for: (a) medicine, (b) inhibiting HIV replication or (c) treating HIV infection and/or reducing the likelihood or severity of symptoms of HIV infection. In these uses, the compounds of the present invention can optionally be employed in combination with one or more second therapeutic agents selected from HIV antiviral agents, anti-infective agents, and immunomodulators.

Additional embodiments of the invention include the pharmaceutical compositions, combinations and methods set forth in (a)-(k) above and the uses set forth in the preceding paragraph, wherein the compound of the present invention employed therein is a compound of one of the embodiments, aspects, classes, sub-classes, or features of the compounds described above. In all of these embodiments, the compound may optionally be used in the form of a pharmaceutically acceptable salt or hydrate as appropriate. It is understood that references to compounds would include the compound in its present form as well as in different forms, such as polymorphs, solvates and hydrates, as applicable.

It is further to be understood that the embodiments of compositions and methods provided as (a) through (k) above are understood to include all embodiments of the compounds, including such embodiments as result from combinations of embodiments.

The Compounds of Formula (I) may be referred to herein by chemical structure and/or by chemical name. In the instance that both the structure and the name of a Compound of Formula (I) are provided and a discrepancy is found to exist between the chemical structure and the corresponding chemical name, it is understood that the chemical structure will predominate.

Non-limiting examples of the Compounds of Formula (I) include compounds 1-38 as set forth below, and pharmaceutically acceptable salts thereof.

Methods for Making the Compounds of Formula (I)

The Compounds of Formula (I) may be prepared from known or readily prepared starting materials, following methods known to one skilled in the art of organic synthesis. Methods useful for making the Compounds of Formula (I) are set forth in the Examples below and generalized in Schemes A-G, below. Alternative synthetic pathways and analogous structures will be apparent to those skilled in the art of organic synthesis. Unless otherwise indicated, all variables are as defined above.

Scheme A depicts a general method for preparing compounds of the present invention wherein a reductive amination between chiral aldehyde 1 and amine 2 provides key amine building block 3. This amine is coupled with carboxylic acid 4 under standard conditions to provide amide 5. Next, acid-mediated global deprotection concurrently removes three protecting groups and liberates an intermediate amino alcohol, which is then cyclized under mild basic biphasic conditions to provide diol 6. Mesylation of 6 affords a mixture of mono- and bis-mesylated intermediate, which is treated with NaOH in situ to affect an intramolecular cyclization to tricyclic morpholine 7. Selective bromination with NBS followed by amidation under carbonylative conditions provides penultimate intermediate 9, which is deprotected under mild acidic conditions with TFA to provide representative compounds of the invention of formula 10.

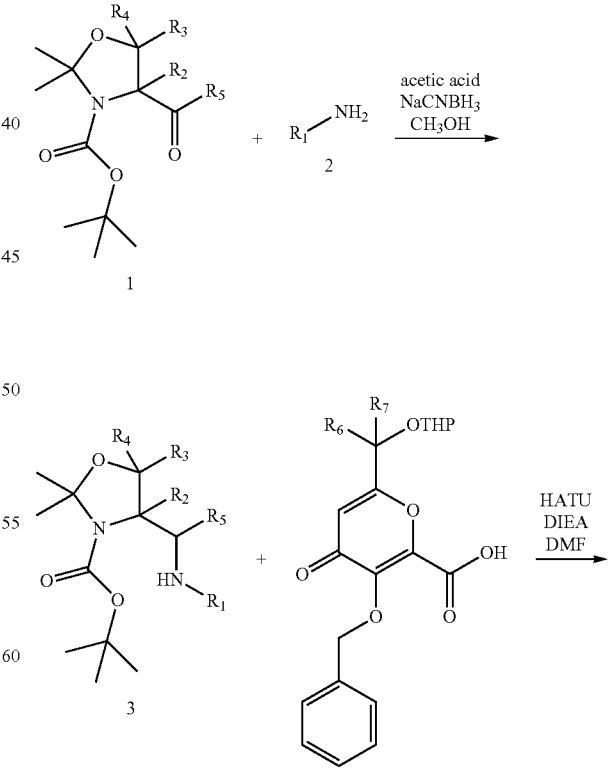

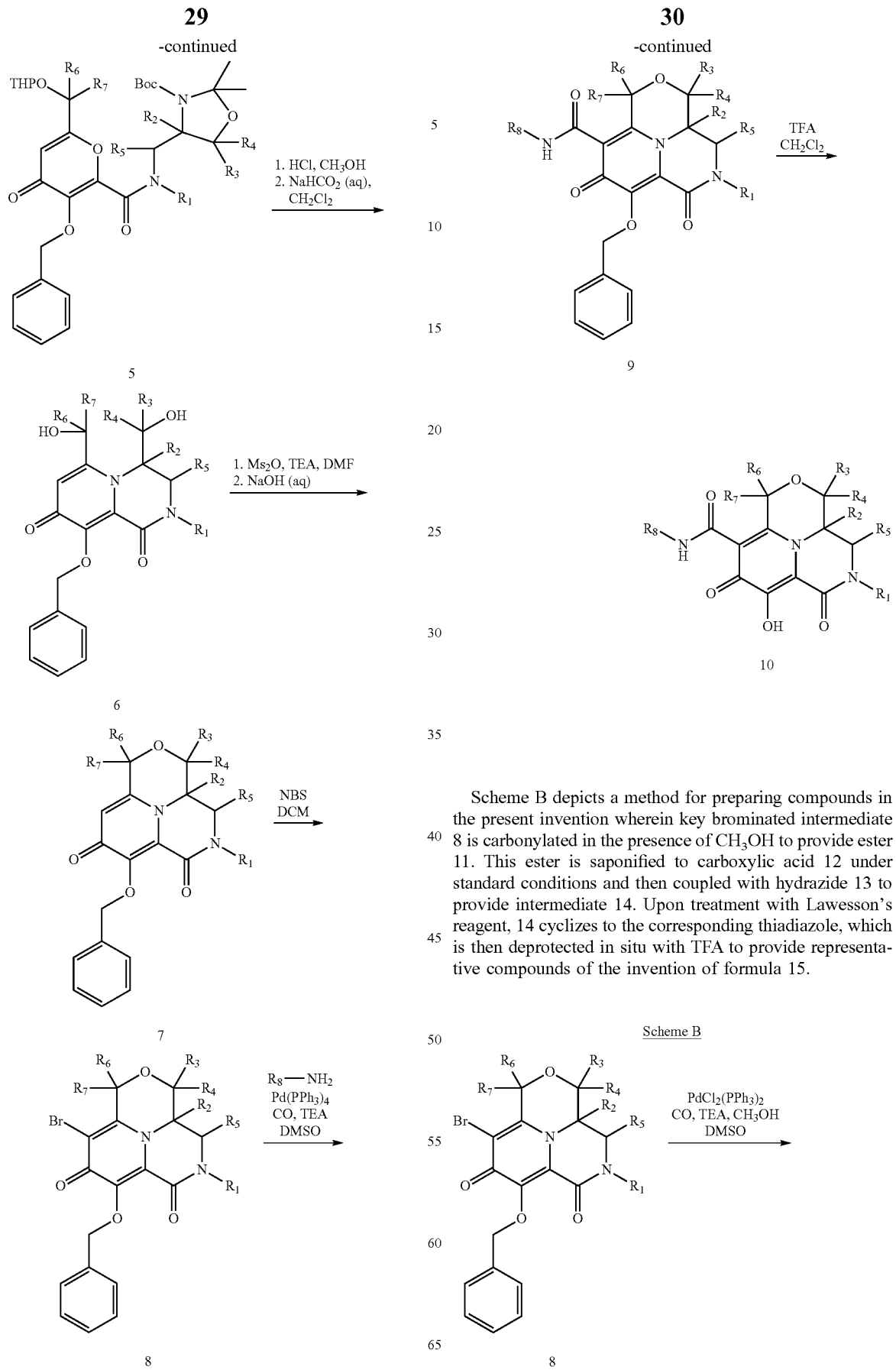

Scheme B depicts a method for preparing compounds in the present invention wherein key brominated intermediate 8 is carbonylated in the presence of $CH_3OH$ to provide ester 11. This ester is saponified to carboxylic acid 12 under standard conditions and then coupled with hydrazide 13 to provide intermediate 14. Upon treatment with Lawesson's reagent, 14 cyclizes to the corresponding thiadiazole, which is then deprotected in situ with TFA to provide representative compounds of the invention of formula 15.

Scheme B

Scheme C

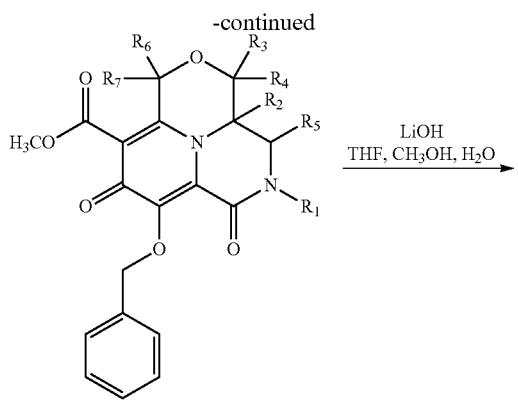

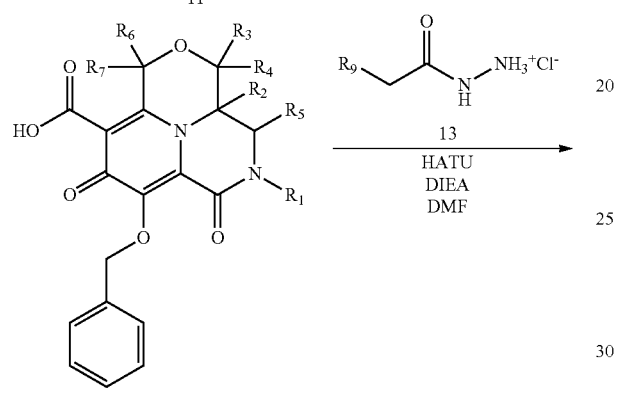

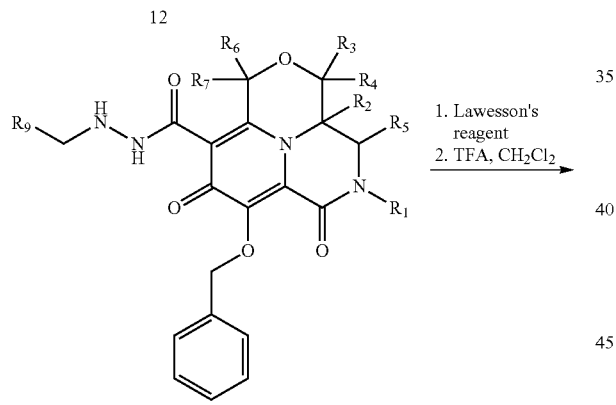

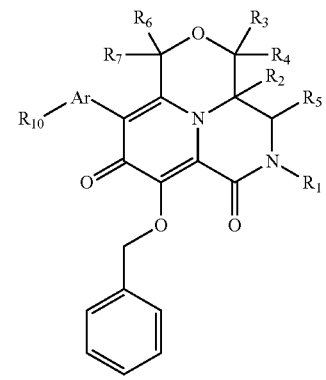

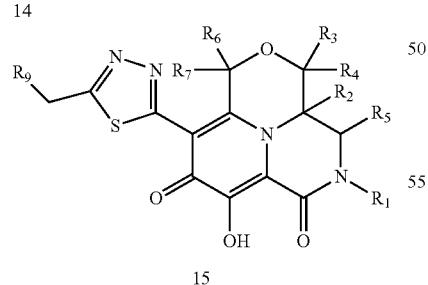

Scheme C depicts a method for preparing compounds in the present invention wherein key brominated intermediate 8 is coupled with aryl boronates of the form 16 under Suzuki coupling conditions to provide an intermediate arene product which is deprotected under mild acidic conditions with TFA to provide representative compounds of the invention of formula 17.

Scheme D depicts a method for preparing compounds in the present invention wherein key brominated intermediate 8 is coupled to a TMS alkyne building block under Sonogashia coupling conditions to provide intermediates of the form 19. 19 undergoes a [3+2] cycloaddition with azides of the form 20 to provide N-linked triazoles of the form 21. 21 can be readily deprotected under mild acidic conditions with TFA to provide representative compounds of the invention of formula 22.

Scheme D

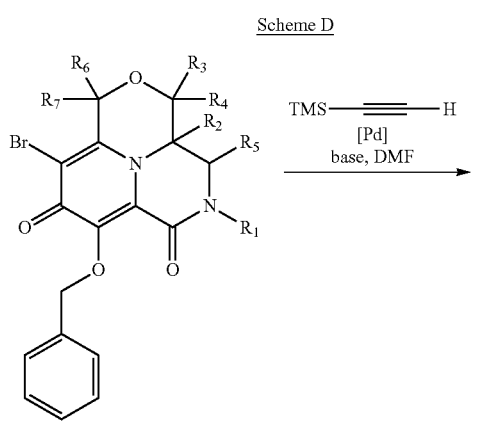

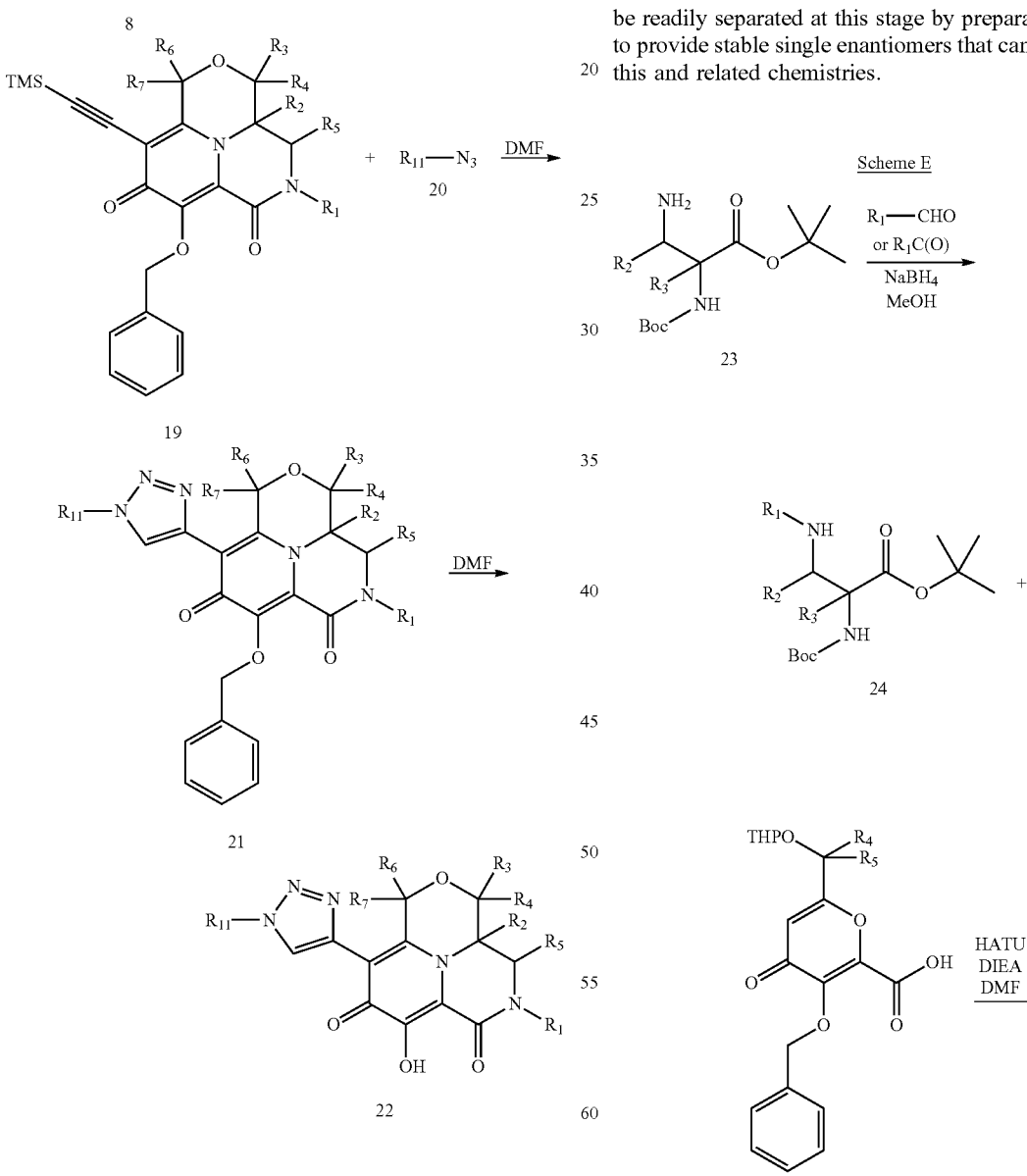

to provide amide 25. Next, acid-mediated deprotection concurrently removes two protecting groups and facilitates cyclization to provide bicyclic ester 26. Mesylation of the primary alcohol of 26 under standard conditions affords intermediate 27, which is then treated with methylamine under forcing conditions to concurrently displace the mesylate intermolecularly followed by intramolecular cyclization of the resulting secondary amine onto the pendant ester to provide tricyclic piperazinone 28. Selective bromination with NBS followed by amidation under carbonylative conditions provides penultimate intermediate 30, which is deprotected under mild acidic conditions with TFA to provide representative compounds of the invention of formula 31.

Bromide 29 of Scheme E is a valuable common intermediate. It is formed as mixture of enantiomers, but these can be readily separated at this stage by preparative chiral SFC to provide stable single enantiomers that can be advanced in this and related chemistries.

Scheme E depicts a general method for preparing compounds of the present invention wherein a reductive amination between chiral amine 23 and either a ketone or an aldehyde provides key amine building block 24. This amine is coupled with carboxylic acid 4 under standard conditions

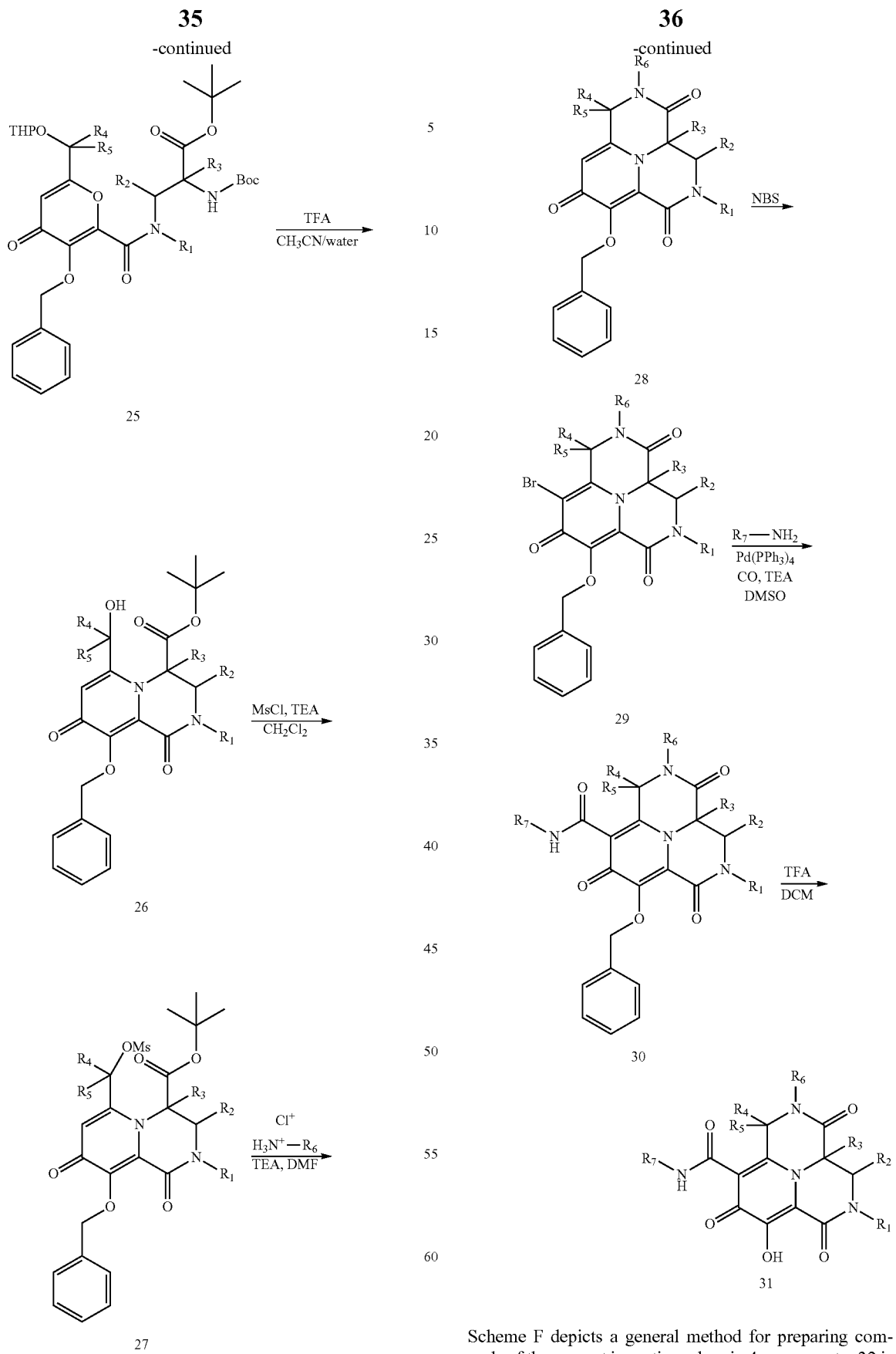
Scheme F depicts a general method for preparing compounds of the present invention wherein 4-pyrone ester 32 is converted first to the corresponding benzylic bromide 33, and subsequently to the corresponding phosphonate 34 through an Arbuzov reaction. 34 undergoes an olefination with chiral carbonyl compound 35, the product of which is hydrogenated under standard conditions, and re-protected to 37. One-pot deprotection mediated by TFA, followed by thermal cyclization and in situ acylation affords key bicyclic building block 40. While 38 and 39 can be isolated/characterized and the indicated operations carried out independently, they are typically carried all the way to the more stable 40. Mesylation of the free hydroxyl moiety followed by cyclization furnishes key tricyclic building block 42. 42 is then brominated selectively, and then subjected to carbonylative amidation catalyzed by Pd(PPh$_3$)$_4$ to provide the penultimate amide intermediate 44. Finally, LiCl-mediated demethylation provides representative compounds of the invention of formula 45.

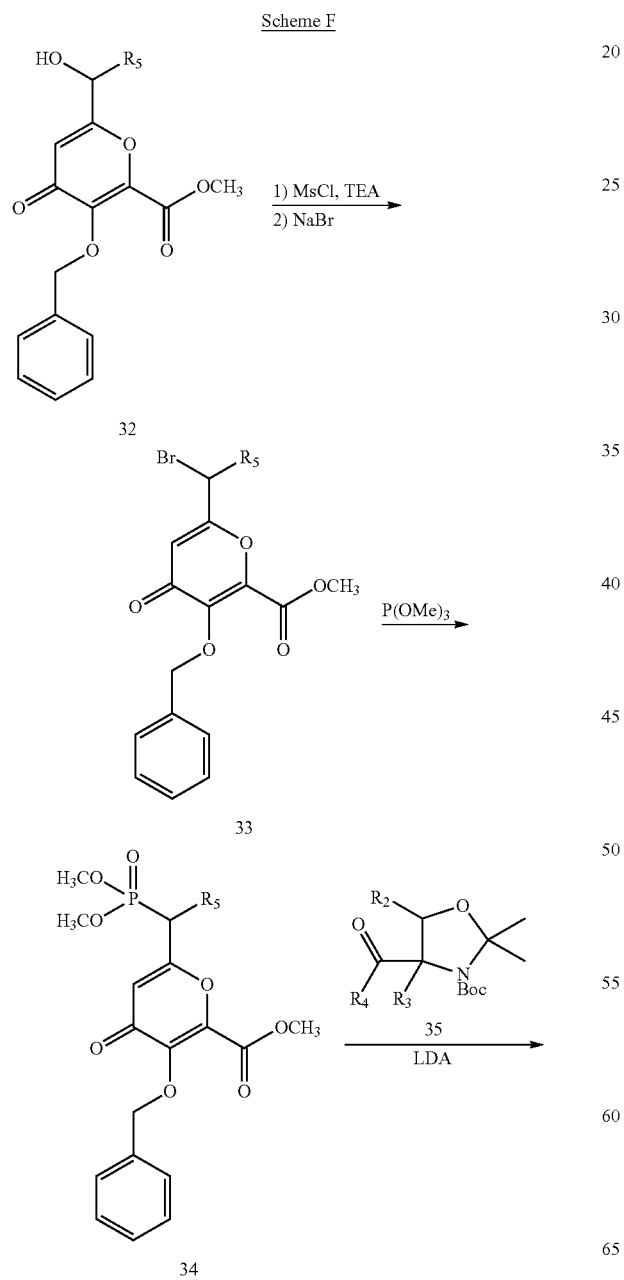

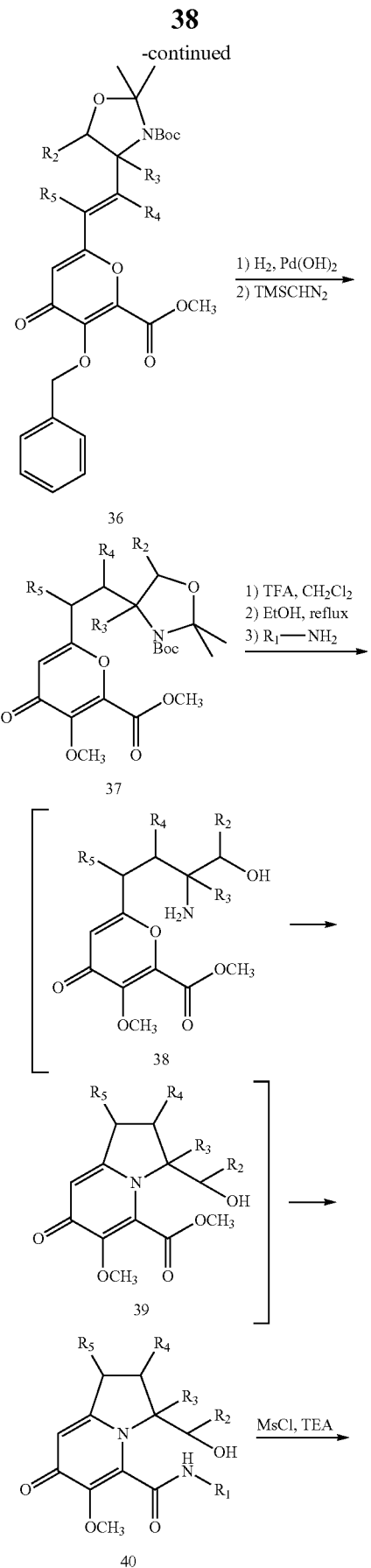

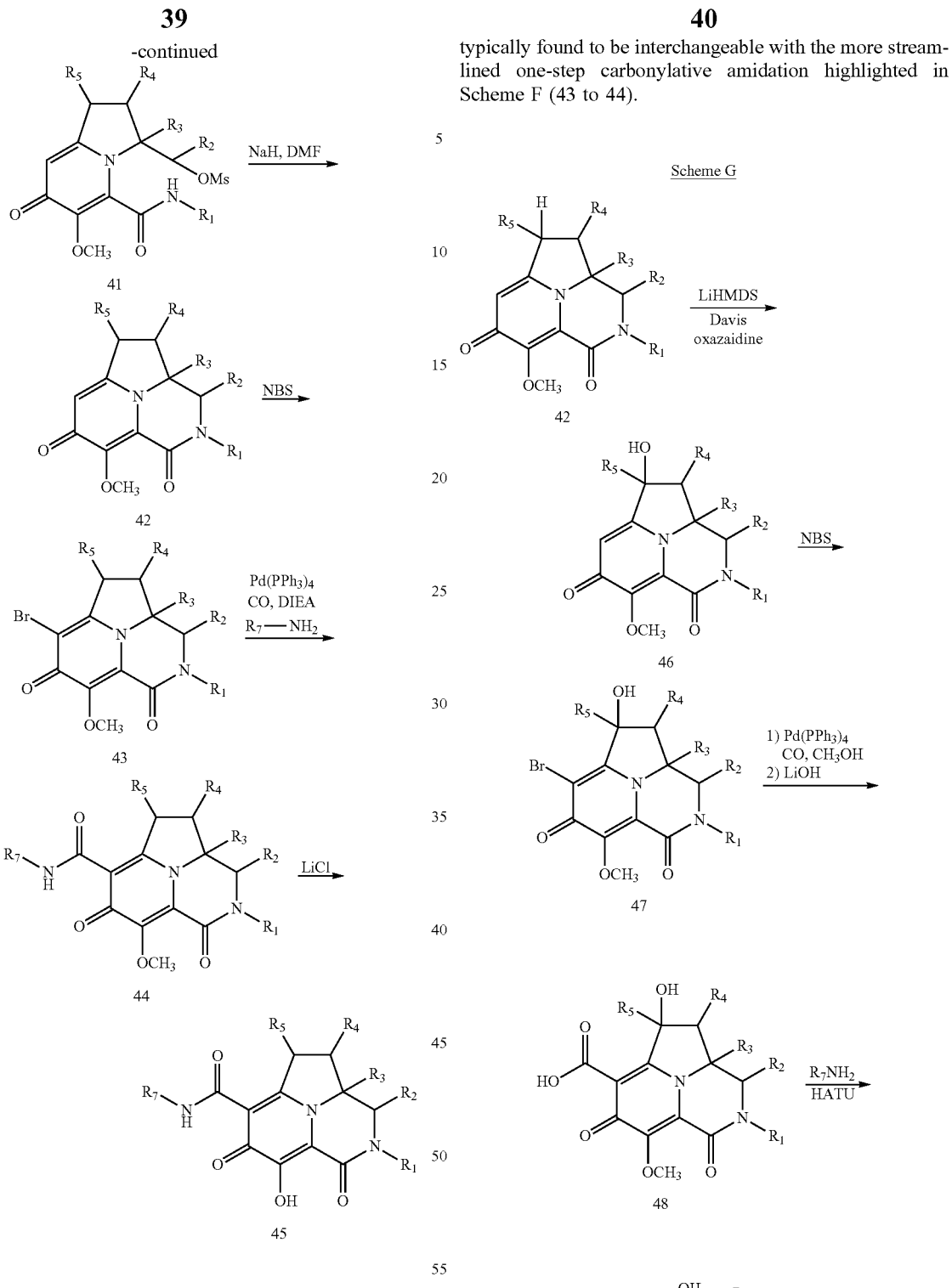

typically found to be interchangeable with the more streamlined one-step carbonylative amidation highlighted in Scheme F (43 to 44).

Scheme G depicts a general method for preparing compounds of the present invention wherein advanced tricyclic intermediate 42 from Scheme F can be oxidized at the benzylic position in the presence of Davis oxaziridine to provide alcohol 46. Using the a protocol similar to that described in Scheme F, 46 is brominated, carboxylated, and saponified to provide carboxylic acid 48. 48 then undergoes a standard amide coupling reaction and then LiCl-mediated demethylation to provide representative compounds of the invention of formula 50. This indicated sequence of steps (carboxylation, saponification, amide coupling) has been

41

-continued

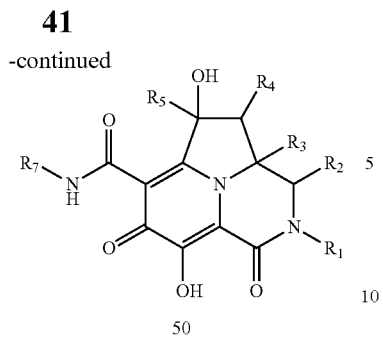
50

Scheme H depicts a general method for preparing compounds of the present invention wherein advanced bicyclic intermediate 40 from Scheme F is oxidized to the corresponding aldehyde resulting in the in situ cyclization of the pendant amide moiety to furnish hydroxy tricycle 51. This compound is then methylated to furnish 52, and then subsequently advanced through a sequence similar to that shown in Scheme F to furnish methoxy compounds of the general structure 55.

Scheme H

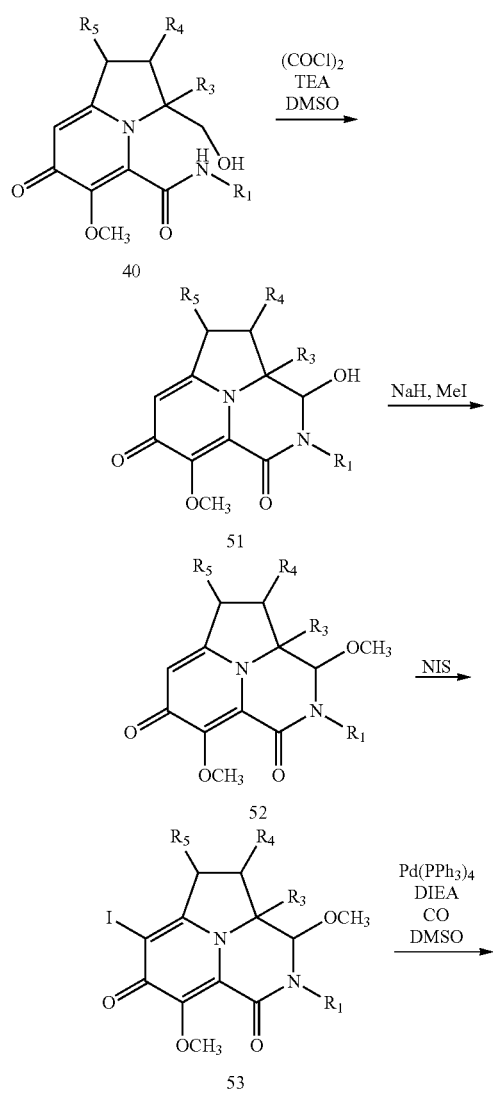

42

-continued

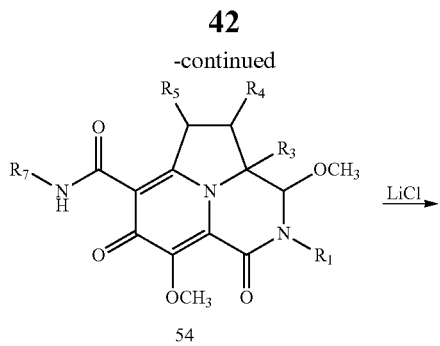
54

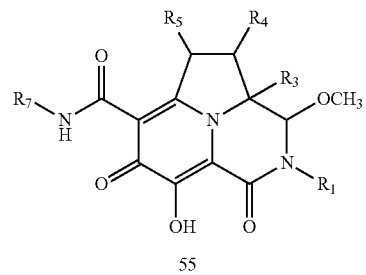
55

Scheme I depicts a general method for preparing compounds of the present invention wherein advanced tricyclic intermediate 46 from Scheme G is methylated, and then subsequently advanced through a sequence similar to that shown in Scheme F to furnish methoxy compounds of the general structure 59.

Scheme I

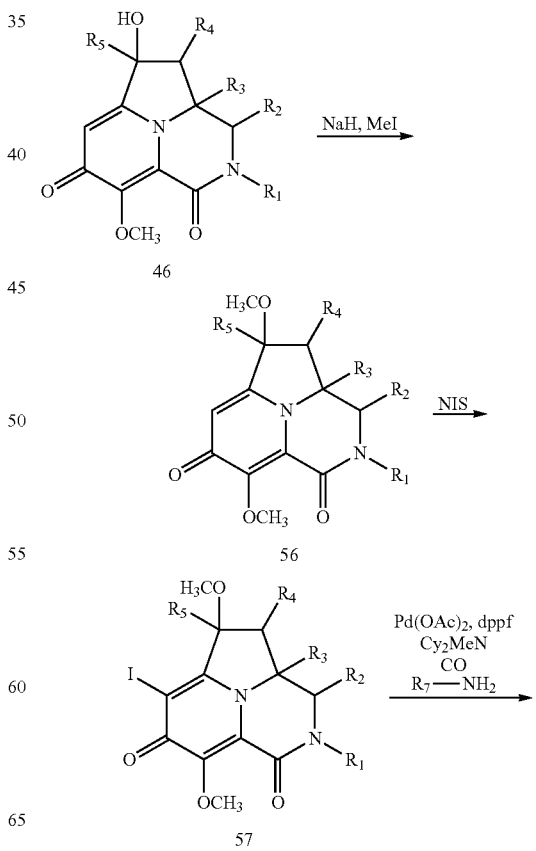

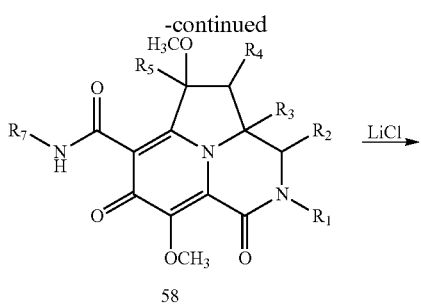

58

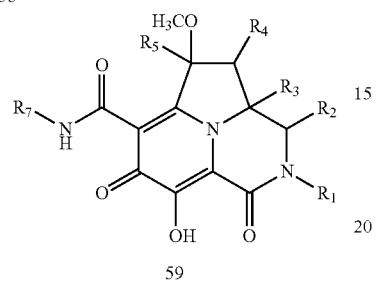

59

In the methods for preparing compounds of the present invention set forth in the foregoing schemes, functional groups in various moieties and substituents (in addition to those already explicitly noted in the foregoing schemes) may be sensitive or reactive under the reaction conditions employed and/or in the presence of the reagents employed. Such sensitivity/reactivity can interfere with the progress of the desired reaction to reduce the yield of the desired product, or possibly even preclude its formation. Accordingly, it may be necessary or desirable to protect sensitive or reactive groups on any of the molecules concerned. Protection can be achieved by means of conventional protecting groups, such as those described in *Protective Groups in Organic Chemistry*, ed. J. F. W. McOmie, Plenum Press, 1973 and in T. W. Greene & P. G. M. Wuts, *Protective Groups in Organic Synthesis*, John Wiley & Sons, 3$^{rd}$ edition, 1999, and 2$^{nd}$ edition, 1991. The protecting groups may be removed at a convenient subsequent stage using methods known in the art. Alternatively the interfering group can be introduced into the molecule subsequent to the reaction Step of concern.

One skilled in the art of organic synthesis will recognize that the synthesis of compounds with multiple reactive functional groups, such as —OH and NH$_2$, may require protection of certain functional groups (i.e., derivatization for the purpose of chemical compatibility with a particular reaction condition). Suitable protecting groups for the various functional groups of these compounds and methods for their installation and removal are well-known in the art of organic chemistry. A summary of many of these methods can be found in Greene & Wuts, *Protecting Groups in Organic Synthesis*, John Wiley & Sons, 3$^{rd}$ edition (1999).

One skilled in the art of organic synthesis will also recognize that one route for the synthesis of the Compounds of Formula (I) may be more desirable depending on the choice of appendage substituents. Additionally, one skilled in the relevant art will recognize that in some cases the order of reactions may differ from that presented herein to avoid functional group incompatibilities and thus adjust the synthetic route accordingly.

Compounds of formula 10, 15, 17, 22, 31, 45, 50, 55, and 59, and their indicated intermediates may be further elaborated using methods that would be well-known to those skilled in the art of organic synthesis or, for example, the methods described in the Examples below, to make the full scope of the Compounds of Formula (I).

The starting materials used and the intermediates prepared using the methods set forth in Schemes A-G may be isolated and purified if desired using conventional techniques, including but not limited to filtration, distillation, crystallization, chromatography and alike. Such materials can be characterized using conventional means, including physical constants and spectral data.

EXAMPLES

General Methods

The following examples serve only to illustrate the invention and its practice. The examples are not to be construed as limitations on the scope or spirit of the invention. In these examples, all temperatures are degrees Celsius unless otherwise noted, and "room temperature" refers to a temperature in a range of from about 20° C. to about 25° C. Mass spectra (MS) were measured by electrospray ion-mass spectroscopy (ESI). $^1$H NMR spectra were recorded on Varian or Bruker instruments at 400-500 MHz. Compounds described herein were synthesized as racemic mixtures unless otherwise stated in the experimental procedures.

Example 1

Preparation of Intermediate Compounds A and B

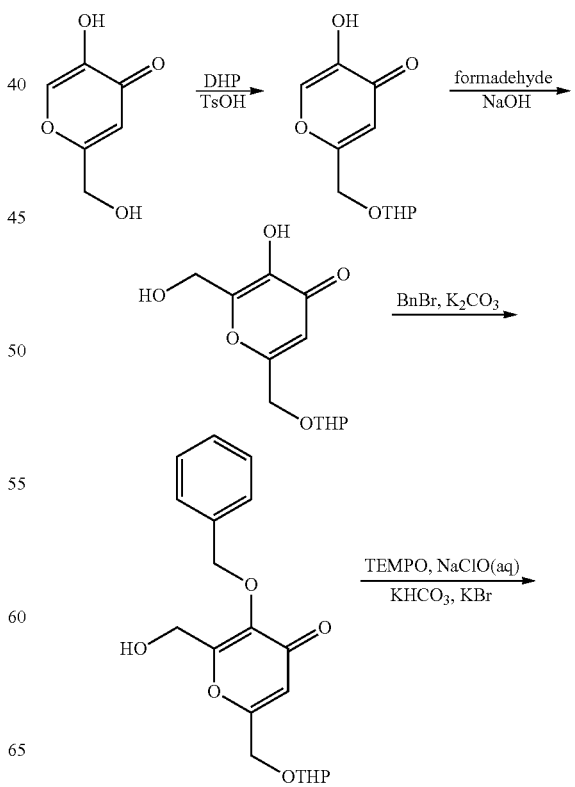

Step 1: 5-hydroxy-2-(((tetrahydro-2H-pyran-2-yl)oxy)methyl)-4H-pyran-4-one

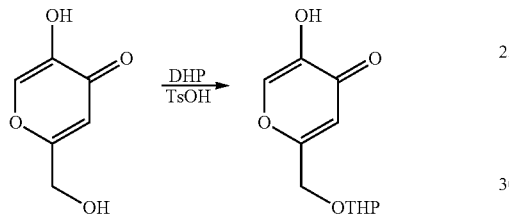

Into a 5-L 4-necked round-bottom flask, purged and maintained with an inert atmosphere of N$_2$, was placed a solution of 5-hydroxy-2-(hydroxymethyl)-4H-pyran-4-one (225 g, 1.58 mol) in CH$_2$Cl$_2$ (2 L) and DHP (158 g, 1.88 mol). This was followed by the addition of 4-methylbenzene-1-sulfonic acid (2.7 g, 15.68 mmol) at 10° C. The resulting solution was stirred for 3 h at room temperature. The reaction was then quenched by the addition of 0.5 N aqueous NaOH (20 mL). The resulting mixture was washed with brine (200 mL). The organic layer was separated and concentrated in vacuo, to provide the title compound (250 g) as a yellow solid, which was used in the subsequent step without further purification.

Step 2: 3-hydroxy-2-(hydroxymethyl)-6-(((tetrahydro-2H-pyran-2-yl)oxy)methyl)-4H-pyran-4-one

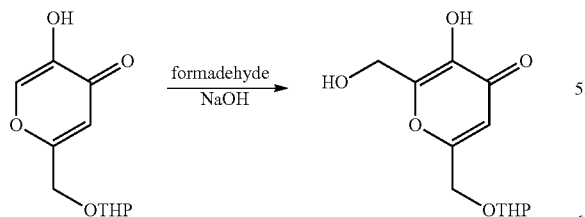

Into a 5-L 4-necked round-bottom flask, purged and maintained with an inert atmosphere of N$_2$, was placed a solution of 5-hydroxy-2-(((tetrahydro-2H-pyran-2-yl)oxy)methyl)-4H-pyran-4-one (250 g, 1.11 mol) in water (1 L), formaldehyde (100 mL) and 1 N aqueous NaOH (1 L). The resulting solution was stirred overnight at room temperature. The pH of the solution was adjusted to pH=5 with AcOH, then extracted with EtOAc (3×500 mL). The organic layers were combined, dried over Na$_2$SO$_4$ and concentrated in vacuo to provide the title compound (310 g, unpurified) as a yellow oil, which was used in the subsequent step without further purification.

Step 3: 3-(benzyloxy)-2-(hydroxymethyl)-6-(((tetrahydro-2H-pyran-2-yl)oxy)-methyl)-4H-pyran-4-one

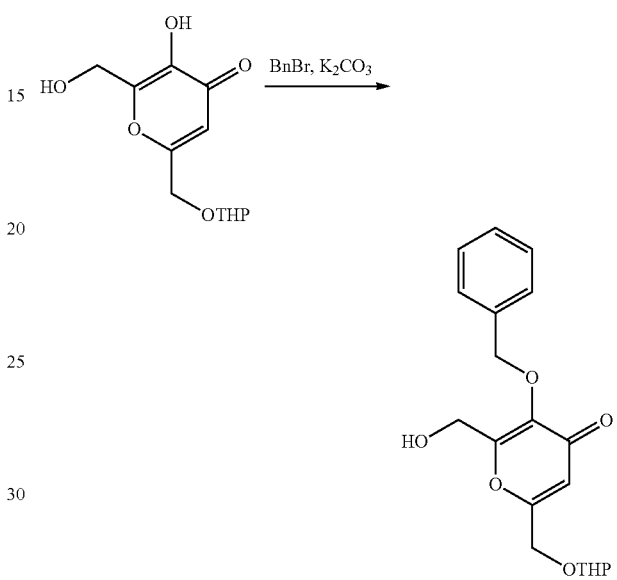

Into a 2-L 4-necked round-bottom flask, purged and maintained with an inert atmosphere of N$_2$, was placed a solution 3-hydroxy-2-(hydroxymethyl)-6-(((tetrahydro-2H-pyran-2-yl)oxy)methyl)-4H-pyran-4-one (310 g, 1.21 mol) in DMF (1.2 L), K$_2$CO$_3$ (334 g, 2.40 mol) and benzyl bromide (217 g, 1.27 mol). The resulting solution was stirred at room temperature for 16 h and then poured into water (5 L). The resulting solution was extracted with of EtOAc (3×1000 mL). The organic layers were combined, dried over Na$_2$SO$_4$ and concentrated under vacuum to provide the title compound (350 g, 84% over 2 steps) as a yellow oil, which was used in the subsequent step without further purification.

Step 4: 3-(benzyloxy)-4-oxo-6-(((tetrahydro-2H-pyran-2-yl)oxy)methyl)-4H-pyran-2-carboxylic acid (Intermediate A)

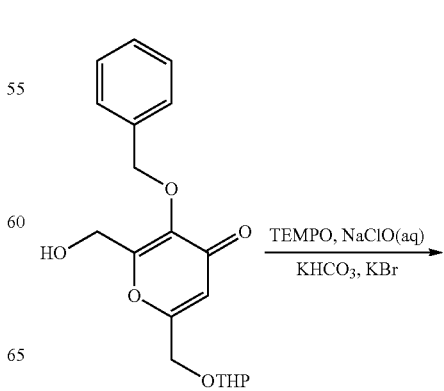

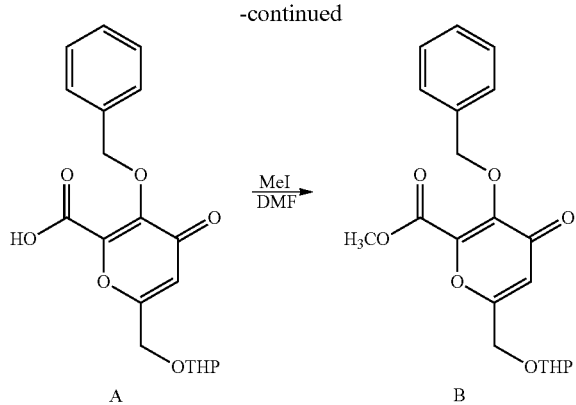

-continued

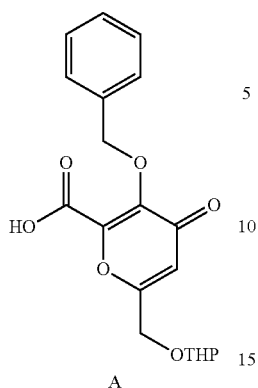

A

Into a 10-L 4-necked round-bottom flask, purged and maintained with an inert atmosphere of N₂, was placed a solution of 3-(benzyloxy)-2-(hydroxymethyl)-6-(((tetrahydro-2H-pyran-2-yl)oxy)methyl)-4H-pyran-4-one (350 g, 1.01 mol) in CH₂Cl₂ (3.5 L), TEMPO (3.16 g, 20.22 mmol), a 1 N aqueous solution of KHCO₃ (300 mL), and a solution of potassium bromide (24 g, 201.68 mmol) in water (20 mL). This was followed by the addition of aqueous NaClO (748.6 g, 30%) added dropwise with stirring at 0° C. over 30 min. The resulting solution was stirred overnight at room temperature. The reaction mixture was cooled to 5° C. with an ice/salt bath, and the pH adjusted to pH3 with 5% aqueous NaHSO₄. The resulting solution was extracted with EtOAc (6×500 mL). The organic layers were combined, dried over Na₂SO₄ and concentrated in vacuo to provide Intermediate Compound A (125 g, 34%) as a white solid.

Step 5: methyl 3-(benzyloxy)-4-oxo-6-(((tetrahydro-2H-pyran-2-yl)oxy)methyl)-4H-pyran-2-carboxylate (Intermediate B)

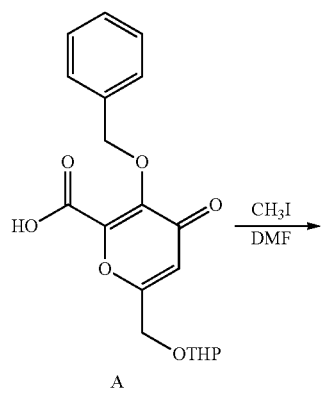

-continued

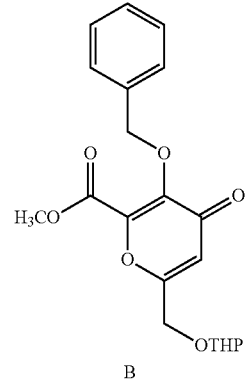

B

Into a 2-L 4-necked round-bottom flask, purged and maintained with an inert atmosphere of nitrogen, was placed a solution of 3-(benzyloxy)-4-oxo-6-(((tetrahydro-2H-pyran-2-yl)oxy)methyl)-4H-pyran-2-carboxylic acid (125 g, 346.9 mmol) in DMF (600 mL), Cs₂CO₃ (226 g, 695.38 mmol), and iodomethane (98.6 g, 694.66 mmol). The resulting solution was stirred at room temperature for 16 h. Next, it was poured into 2 L of water/ice. The solid was collected by filtration and dried in an oven under reduced pressure to provide Intermediate Compound B (105 g, 81%) as a yellow solid. LRMS (+ESI) m/z=375. ¹H NMR (400 MHz, CDCl₃): δ 7.48-7.44 (2H, d); 7.39-7.29 (3H, m); 6.58 (1H, s); 5.31 (2H, s); 4.74-4.72 (1H, d); 4.59-4.54 (1H, d); 4.40-4.35 (1H, d); 3.86-3.78 (4H, m); 3.58-3.54 (1H, m); 1.87-1.65 (6H, m).

Example 2

Preparation of Intermediate Compound C

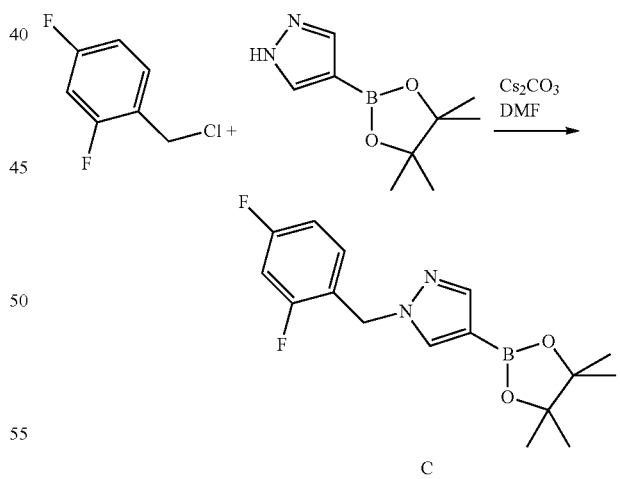

C 1-(chloromethyl)-2,4-difluorobenzene (948 mg, 5.8 mL) and 4-(4,4,5,5-tetramethyl-1,3,2-dioxaborolan-2-yl)-1H-pyrazole (750 mg, 3.87 mmol) were combined in DMF (12 mL) at room temperature. Solid Cs₂CO₃ (2.5 g, 7.73 mmol) was then added, and the reaction mixture was stirred at room temperature for 16 h. The reaction mixture was filtered through a scintered glass funnel, and the filtrate was purified directly by gradient elution on reverse phase (50×250 mm (5 um) Sunfire Prep C18; 27 to 62% CH₃CN/water w/ 0.1%

TFA modifier over 30 min at 90 mL/min) to provide Intermediate Compound C (540 mg, 44%) as an orange oil. LRMS (+ESI) m/z=321.4.

Example 3

Preparation of Intermediate Compound D

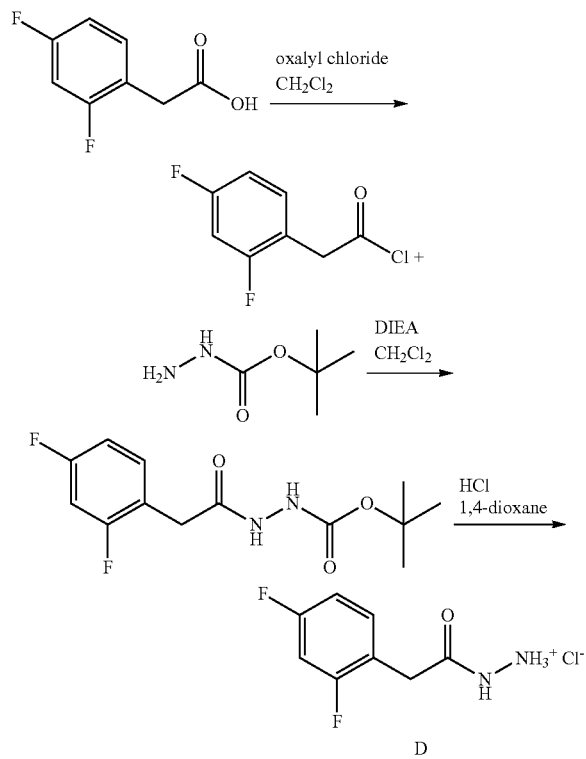

Step 1: 2-(2,4-difluorophenyl)acetyl chloride

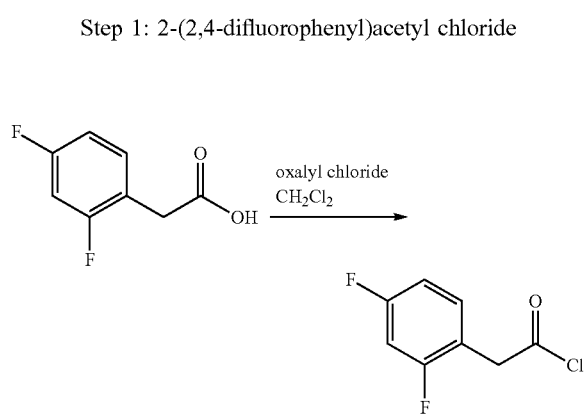

To a solution of 2-(2,4-difluorophenyl)acetic acid (1.15 g, 6.68 mmol) in CH$_2$Cl$_2$ (66.8 mL) was added oxalyl chloride (4.01 mL, 8.02 mmol) followed by 2 drops of DMF. The solution was stirred for 2 h at room temperature and then concentrated to dryness in vacuo. The resulting unpurified residue (1.27 g) was used in the subsequent step without further purification, assuming quantitative conversion.

Step 2: tert-butyl 2-(2-(2,4-difluorophenyl)acetyl) hydrazinecarboxylate

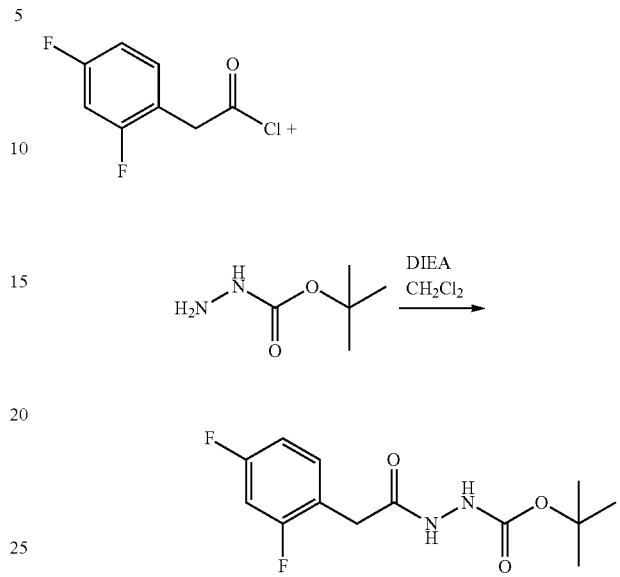

A solution of unpurified 2-(2,4-difluorophenyl)acetyl chloride (0.406 g, 2.13 mmol) in CH$_2$Cl$_2$ (5 mL) was added dropwise to a stirring solution of tert-butyl hydrazinecarboxylate (0.282 g, 2.130 mmol) and DIEA (0.446 ml, 2.56 mmol) in CH$_2$Cl$_2$ (21.3 mL). The reaction mixture was stirred for 16 h at room temperature, and then washed sequentially with 1 N aqueous HCl (30 mL) and saturated aqueous NaHCO$_3$ (30 mL). The organic phase was dried over Na$_2$SO$_4$ and concentrated in vacuo, and the resulting unpurified residue (0.564 g) was used in the subsequent step without further purification.

Step 3: 2-(2,4-difluorophenyl)acetohydrazide hydrochloride

To unpurified tert-butyl 2-(2-(2,4-difluorophenyl)acetyl) hydrazinecarboxylate (0.564 g, 1.970 mmol) in 1,4-dioxane (19.70 mL) was added a 4 N 1,4-dioxane solution of HCl (1.72 mL, 6.90 mmol) and stirred for 2 days at room temperature. The reaction mixture was concentrated in vacuo, and the resulting hydrochloride salt (0.395 g) was used in subsequent chemistry without further purification. LRMS (+ESI) m/z=187.1.

Example 4
Preparation of Compounds 2 and 3
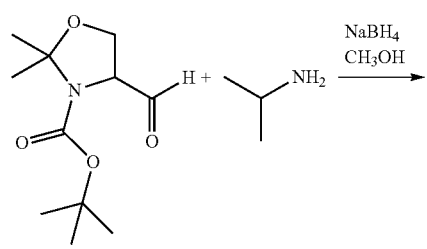
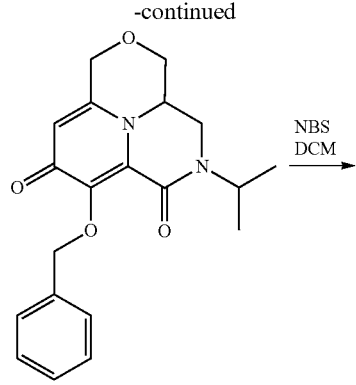
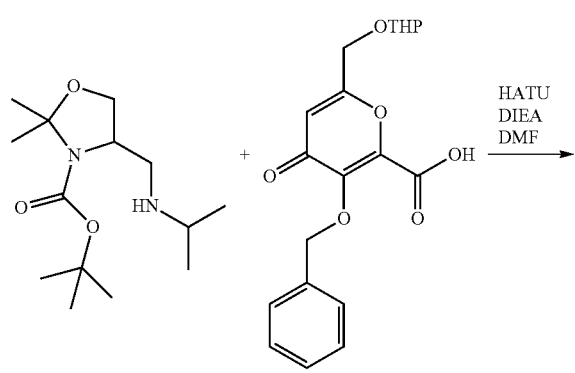
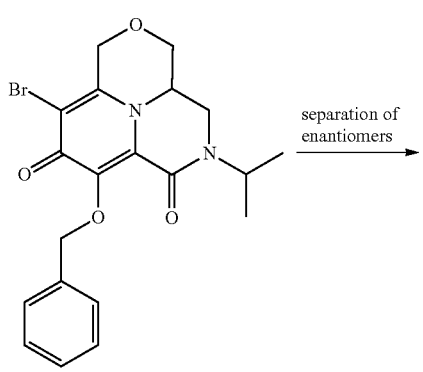
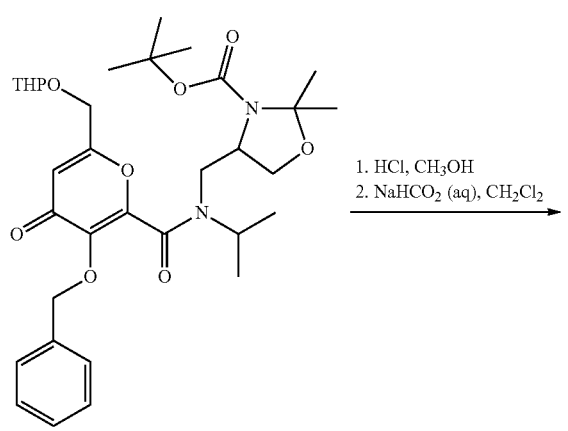
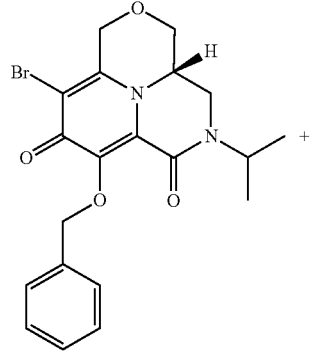
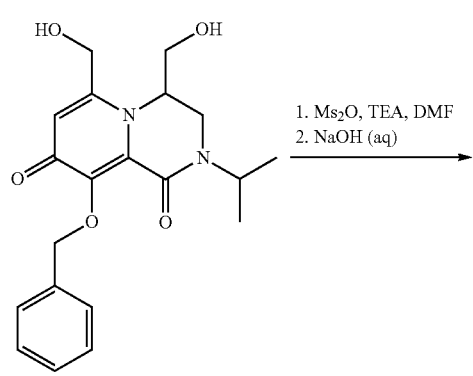
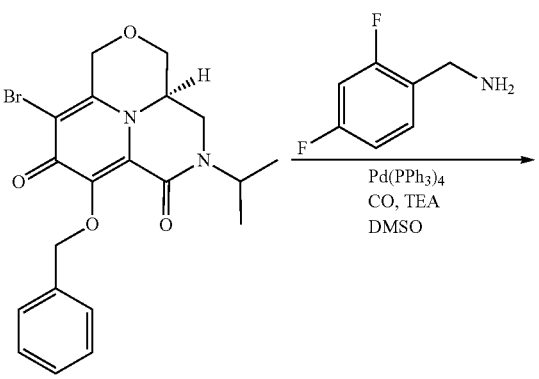

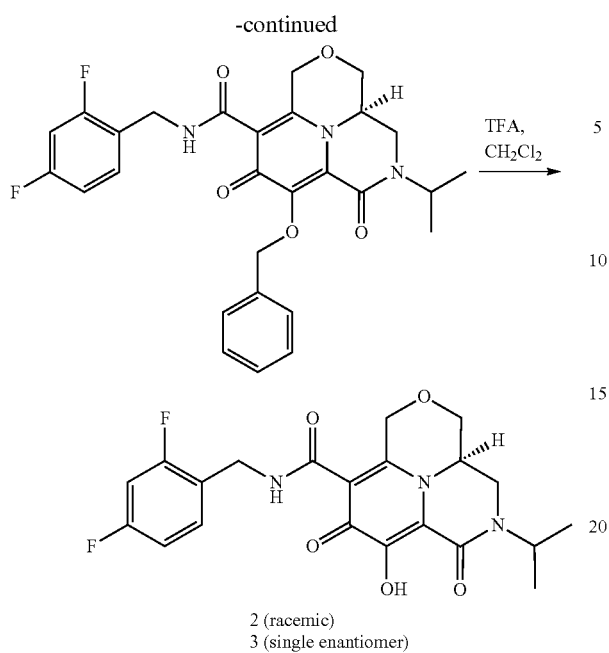

2 (racemic)
3 (single enantiomer)

Step 1: tert-butyl 4-((isopropylamino)methyl)-2,2-dimethyloxazolidine-3-carboxylate

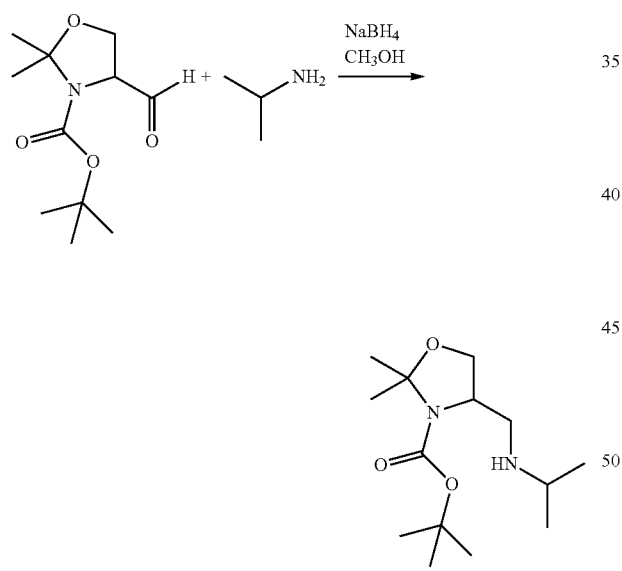

To tert-butyl 4-formyl-2,2-dimethyloxazolidine-3-carboxylate (10 g, 43.6 mmol) in CH$_3$OH (87 mL) was added isopropylamine (14.86 mL, 174 mmol). The resulting mixture was stirred at 50° C. for 16 h. The mixture was cooled to room temperature and NaBH$_4$ (4.95 g, 131 mmol) was added. The resulting mixture was stirred at room temperature for 1 hour. Saturated aqueous NaHCO$_3$ (100 mL) was added and the slurry was extracted with ~4:1 CH$_2$Cl$_2$/EtOH (2×500 mL). The organics were combined and concentrated to provide the title compound (11.9 g, 99%) as a pale yellow oil. LRMS (+ESI) m/z=273.5.

Step 2: tert-butyl 4-((3-(benzyloxy)-N-isopropyl-4-oxo-6-(((tetrahydro-2H-pyran-2-yl)oxy)methyl)-4H-pyran-2-carboxamido)methyl)-2,2-dimethyloxazolidine-3-carboxylate

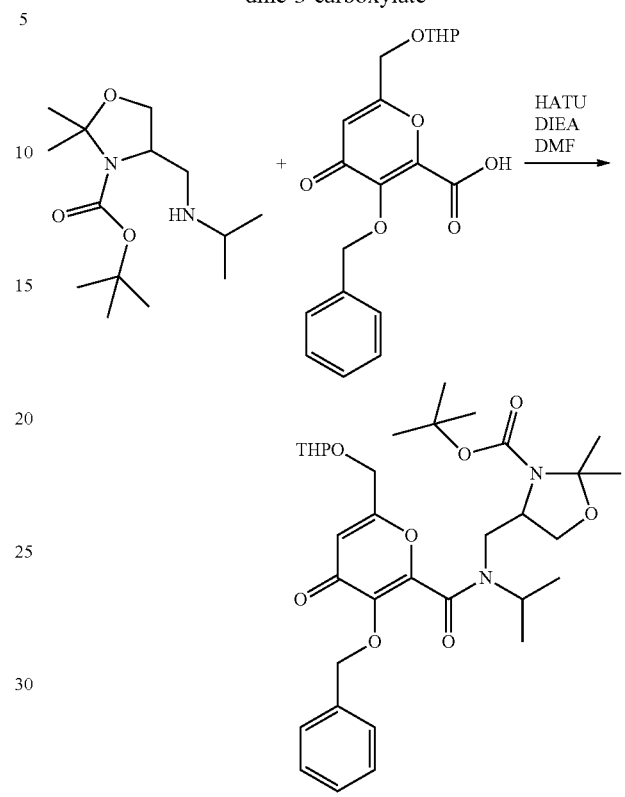

A solution of tert-butyl 4-((isopropylamino)methyl)-2,2-dimethyloxazolidine-3-carboxylate (10 g, 36.7 mmol) and Intermediate A (12.4 g, 34.4 mmol) in DMF (68.8 mL) was treated with HATU (14.39 g, 37.9 mmol) then DIEA (18.03 mL, 103 mmol). The mixture was stirred at room temperature for 10 min and then partitioned between water (300 mL) and EtOAc (500 mL). The organic phase was washed with water (2×300 mL) and brine (1×200 mL), and then dried over Na$_2$SO$_4$, filtered, then concentrated in vacuo. The resulting residue (~24 g) was used in the subsequent step without further purification. LRMS (+ESI) m/z=615.4.

Step 3: 9-(benzyloxy)-4,6-bis(hydroxymethyl)-2-isopropyl-3,4-dihydro-1H-pyrido[1,2-a]pyrazine-1,8(2H)-dione

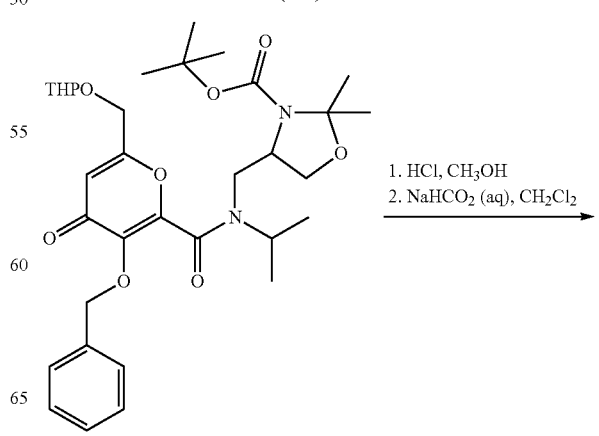

-continued

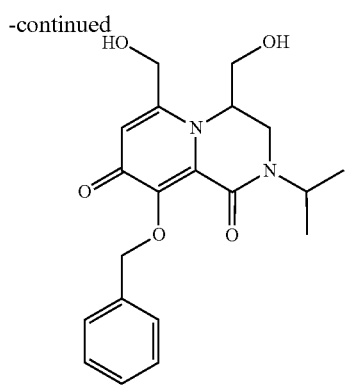

A solution of tert-butyl 4-((3-(benzyloxy)-N-isopropyl-4-oxo-6-((((tetrahydro-2H-pyran-2-yl)oxy)methyl)-4H-pyran-2-carboxamido)methyl)-2,2-dimethyloxazolidine-3-carboxylate (21.2 g, 34.5 mmol) in CH$_3$OH (86 mL) was treated with concentrated HCl (7.18 mL, 86 mmol) and stirred at 70° C. for 30 min. The mixture was concentrated in vacuo and the residue suspended in CH$_2$Cl$_2$ (100 mL), treated with saturated aqueous NaHCO$_3$ (100 mL), stirred vigorously for 20 min, and the layers were then separated. The aqueous phase was back-extracted with ~4:1 CH$_2$Cl$_2$/EtOH (3×500 mL). The organic layers were combined and concentrated in vacuo to provide the title compound (12.8 g) as a tan foam, which was used in the subsequent step without further purification. LRMS (+ESI) m/z=373.3.

Step 4: 7-(benzyloxy)-5-isopropyl-3,3a,4,5-tetrahydro-1H-2-oxa-3a1,5-diazaphenalene-6,8-dione

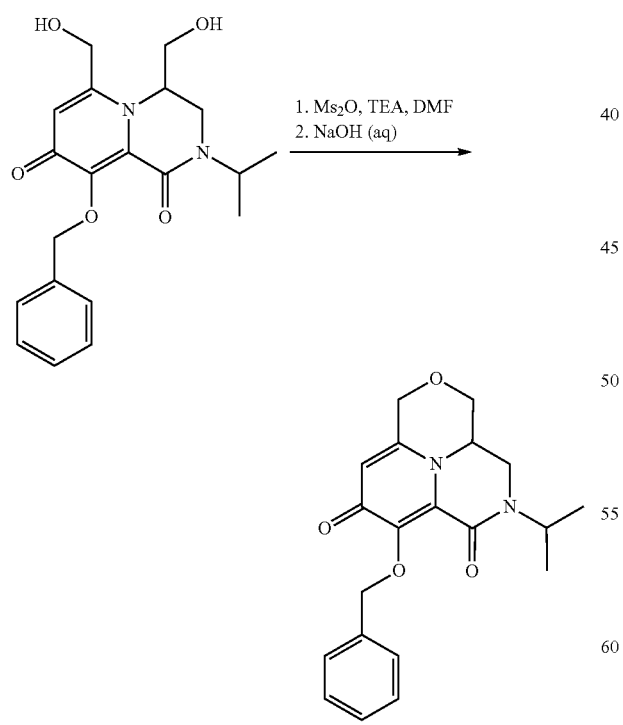

A solution of 9-(benzyloxy)-4,6-bis(hydroxymethyl)-2-isopropyl-3,4-dihydro-1H-pyrido[1,2-a]pyrazine-1,8(2H)-dione (12.8 g, 34.4 mmol) in DMF (344 mL) was treated with TEA (9.58 mL, 68.7 mmol) and cooled to 0° C. The mixture was treated with methanesulfonic anhydride (5.99 g, 34.4 mmol) and was stirred at 0° C. for 20 min. The mixture was treated with 1 N aqueous NaOH (172 mL, 172 mmol) and stirred at 0° C. for 20 min. Next, the reaction mixture was extracted with CH$_2$Cl$_2$ (400 mL). The aqueous phase was back-extracted with a ~4:1 mixture of CH$_2$Cl$_2$:EtOH (2×500 mL). The organic phases were combined and the total volume reduced to ~250 mL (primarily DMF), and the resulting solution was carried on to the subsequent step without further purification assuming quantitative conversion. LRMS (+ESI) m/z=355.2.

Step 5: (S) and (R)-7-(benzyloxy)-9-bromo-5-isopropyl-3,3a,4,5-tetrahydro-1H-2-oxa-3a1,5-diazaphenalene-6,8-dione

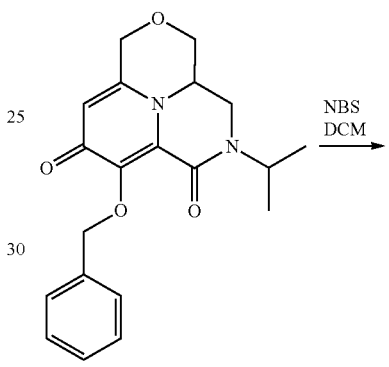

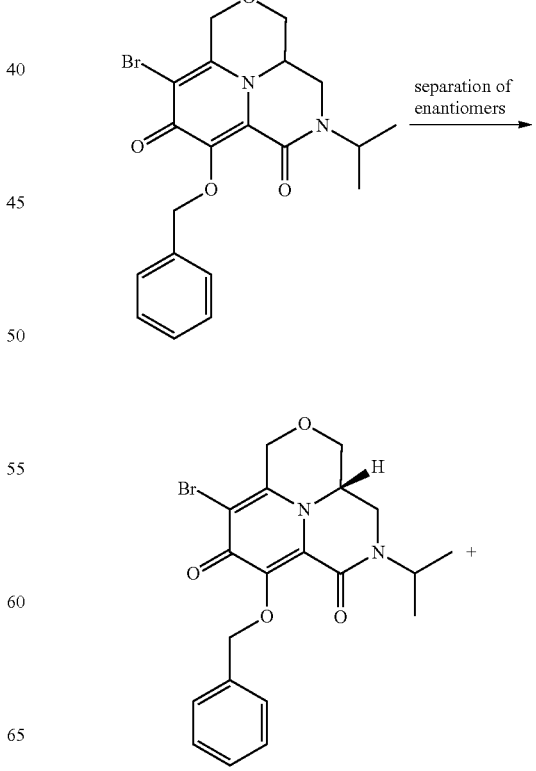

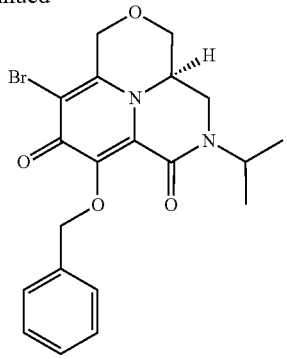

A solution of unpurified 7-(benzyloxy)-5-isopropyl-3,3a,4,5-tetrahydro-1H-2-oxa-3a1,5-diazaphenalene-6,8-dione in ~250 mL DMF (12 g, 33.9 mmol) from the previous step was diluted with DCM (100 mL, 0.1 M total concentration), treated with NBS (9.04 g, 50.8 mmol), and stirred at room temperature for 10 min. The mixture was concentrated and partitioned between water (300 mL) and EtOAc (400 mL). The aqueous phase was back-extracted with EtOAc (400 mL) and then with CH$_2$Cl$_2$ (400 mL). The combined organic phases were dried over Na$_2$SO$_4$, filtered, and concentrated in vacuo. The resulting residue was purified by gradient elution on silica gel (RediSep-Rf-330 g, 0 to 100% [10% MeOH in CH$_2$Cl$_2$]/CH$_2$Cl$_2$, 35 minute gradient) to provide the title racemic compound as an orange oil (6.8 g, 45.6% over 4 steps, ~80% pure). LRMS (+ESI) m/z=433.3. $^1$H NMR (500 MHz, CDCl$_3$): δ 7.70 (d, J=7.4 Hz, 2H); 7.33-7.35 (m, 3H); 5.34 (d, J=9.4 Hz, 1H); 5.04 (d, J=9.4 Hz, 1H); 4.94 (d, J=16.7 Hz, 1H); 4.80-4.82 (m, 1H); 4.71 (d, J=16.8 Hz, 1H); 4.01-4.07 (m, 2H); 3.74 (t, J=11.3 Hz, 1H); 3.31 (t, J=12.8 Hz, 1H); 2.96-2.98 (m, 1H); 1.13 (d, J=6.7 Hz, 3H); 0.99 (d, J=6.9 Hz, 3H).

Enantiomers were separated by chiral preparative SFC (2-cm×25-cm OD-H column; isocratic [50% (0.1% DEA/CH$_3$OH)]/[50% CO$_2$]; 50 mL/min flowrate; 220 nm) to provide (S) and (R)-7-(benzyloxy)-9-bromo-5-isopropyl-3,3a,4,5-tetrahydro-1H-2-oxa-3a1,5-diazaphenalene-6,8-diones as tan solids. The second eluting enantiomer was determined to be the enantiomer of interest.

Step 6: (R)-7-(benzyloxy)-N-(2,4-difluorobenzyl)-5-isopropyl-6,8-dioxo-3,3a,4,5,6,8-hexahydro-1H-2-oxa-3a1,5-diazaphenalene-9-carboxamide A suspension of (R)-7-(benzyloxy)-9-bromo-5-isopropyl-3,3a,4,5-tetrahydro-1H-2-oxa-3a1,5-diazaphenalene-6,8-dione (200 mg, 0.462 mmol), DIEA (0.403 mL, 2.308 mmol), (2,4-difluorophenyl)methanamine (264 mg, 1.846 mmol), and Pd(PPh$_3$)$_4$ (213 mg, 0.185 mmol) in DMSO (15.4 mL) was degassed with a stream of N$_2$, the flask was evacuated, and back-filled three times with CO$_{(g)}$. The reaction mixture was stirred under a CO$_{(g)}$ atmosphere (balloon) at 100° C. for 16 hours. The mixture was partitioned between water (50 mL) and EtOAc (50 mL). The organic phase was washed with water (50 mL) and brine (50 mL), dried over Na$_2$SO$_4$, filtered, and in vacuo. The resulting residue was purified by gradient elution on reverse phase (30×150 mm (5 um) Sunfire Prep C18; 5 to 95% CH$_3$CN/water w/ 0.1% TFA modifier over 20 min at 40 mL/min) to provide the title compound (167 mg, 69%) as a tan foam. LRMS (+ESI) m/z=524.3. $^1$H NMR (500 MHz, CDCl$_3$): δ 11.03 (s, 1H); 7.61 (d, J=7.4 Hz, 2H); 7.33-7.35 (m, 4H); 6.81-6.83 (m, 2H); 5.73 (d, J=18.4 Hz, 1H); 5.40 (d, J=9.9 Hz, 1H); 5.17-5.18 (m, 2H); 4.88-4.89 (m, 1H); 4.58-4.60 (m, 2H); 4.21-4.24 (m, 2H); 3.59 (t, J=11.0 Hz, 1H); 3.28-3.30 (m, 1H); 3.12 (t, J=12.4 Hz, 1H); 1.22 (d, J=6.6 Hz, 3H); 1.15 (d, J=6.9 Hz, 3H).

Step 7: (R)—N-(2,4-difluorobenzyl)-7-hydroxy-5-isopropyl-6,8-dioxo-3,3a,4,5,6,8-hexahydro-1H-2-oxa-3a1,5-diazaphenalene-9-carboxamide (Compound 3)

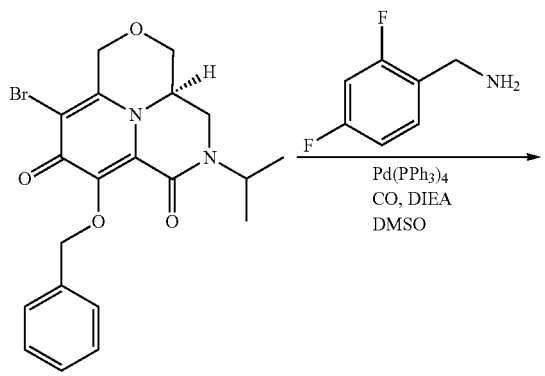
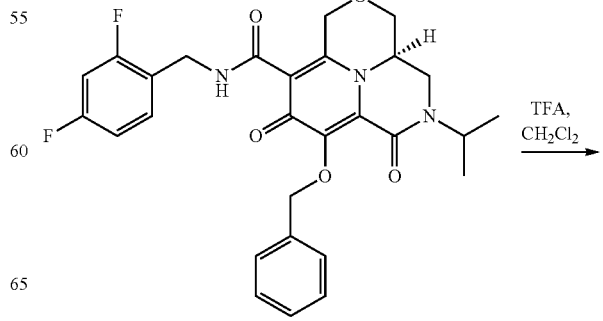

-continued

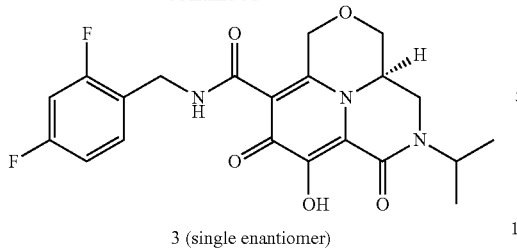

3 (single enantiomer)

A solution of (R)-7-(benzyloxy)-N-(2,4-difluorobenzyl)-5-isopropyl-6,8-dioxo-3,3a,4,5,6,8-hexahydro-1H-2-oxa-3a1,5-diazaphenalene-9-carboxamide (167 mg, 0.319 mmol) in TFA (1.5 mL, 19.47 mmol) was heated to 60° C. and stirred for 10 min. The mixture was concentrated in vacuo and purified directly by gradient elution on reverse phase (30×150 mm (5 um) Sunfire Prep C18; 5 to 95% $CH_3CN$/water w/ 0.1% TFA modifier over 20 min at 40 mL/min) to provide compound 2 (83.8 mg, 60.6%) as an off-white crystalline solid. LRMS (+ESI) m/z=434.2. $^1$H NMR (400 MHz, $CDCl_3$): δ 10.71 (s, 1H); 7.36 (q, J=7.8 Hz, 1H); 6.78-6.81 (m, 2H); 5.52 (d, J=17.9 Hz, 1H); 5.09 (d, J=17.9 Hz, 1H); 4.92-4.94 (m, 1H); 4.56 (bm, 2H); 4.24-4.27 (m, 2H); 3.72 (t, J=10.7 Hz, 1H); 3.40-3.42 (m, 2H); 1.26 (d, J=6.8 Hz, 3H); 1.23 (d, J=6.8 Hz, 3H).

Racemic 7-(benzyloxy)-9-bromo-5-isopropyl-3,3a,4,5-tetrahydro-1H-2-oxa-3a1,5-diazaphenalene-6,8-dione was also carried forth according to the methods described in above to provide racemic compound 2:

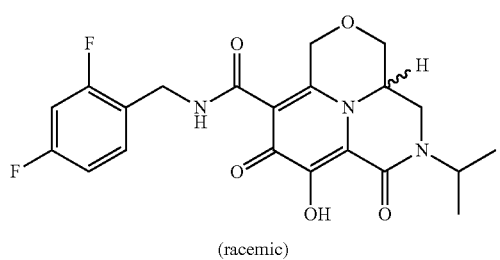

(racemic)

LRMS (+ESI) m/z = 434.2

Example 5

Preparation of Compound 13

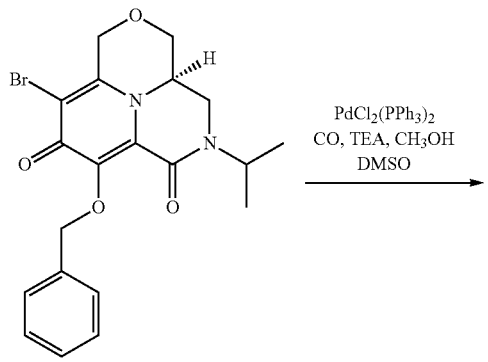

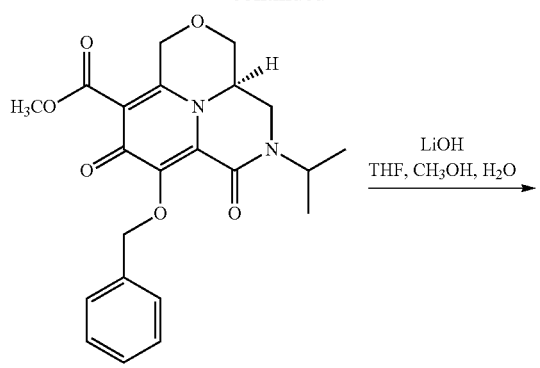

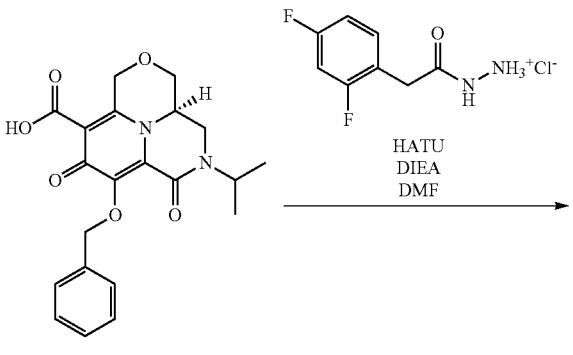

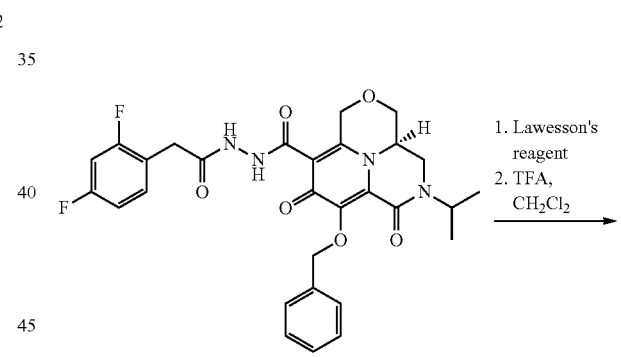

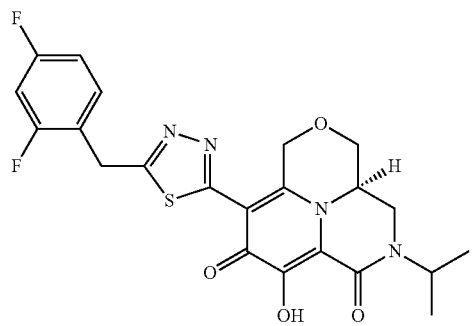

13

Step 1: methyl 7-(benzyloxy)-5-isopropyl-6,8-di-oxo-3,3a,4,5,6,8-hexahydro-1H-2-oxa-3a1,5-diaza-phenalene-9-carboxylate

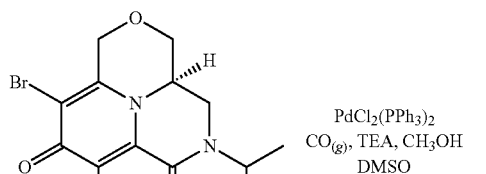

A suspension of 7-(benzyloxy)-9-bromo-5-isopropyl-3,3a,4,5-tetrahydro-1H-2-oxa-3a1,5-diazaphenalene-6,8-dione (Example 4, 100 mg, 0.231 mmol), DIEA (202 µl, 1.154 mmol), and Pd(PPh₃)₄ (107 mg, 0.092 mmol) in DMSO (5770 µl) and CH₃OH (1923 µl) was degassed with N₂ for 2 min. Next, the flask was evacuated and back-filled with three times with CO$_{(g)}$. The reaction mixture was heated to 90° C. and stirred under an atmosphere of CO$_{(g)}$ (balloon) for 16 hours. The mixture was filtered through a syringe filter and the filtrate was purified directly by gradient elution on reverse phase (30×150 mm (5 um) Sunfire Prep C18; 5 to 95% CH₃CN/water w/ 0.1% TFA modifier over 20 min at 40 mL/min) to provide the title compound (14 mg, 14.7%) as a yellow film. LRMS (+ESI) m/z=413.2.

Step 2: 7-(benzyloxy)-5-isopropyl-6,8-dioxo-3,3a,4,5,6,8-hexahydro-1H-2-oxa-3a1,5-diazaphenalene-9-carboxylic acid

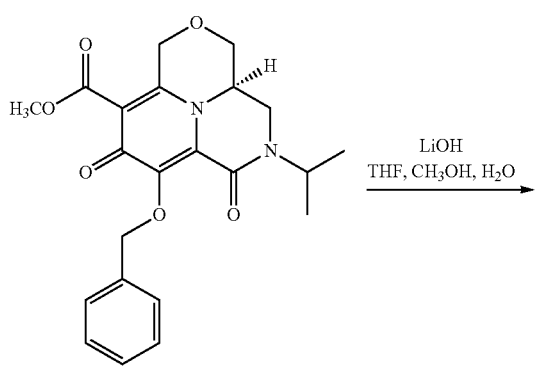

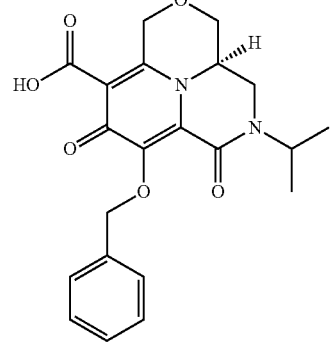

To a solution of methyl 7-(benzyloxy)-5-isopropyl-6,8-dioxo-3,3a,4,5,6,8-hexahydro-1H-2-oxa-3a1,5-diazaphenalene-9-carboxylate (14 mg, 0.034 mmol) in THF (226 µl), CH₃OH (56.6 µl), and water (56.6 µl) was added lithium hydroxide monohydrate (1.42 mg, 0.034 mmol). The reaction mixture was stirred for 1 hour at room temperature. Next, the reaction mixture was neutralized with 1 N HCl, concentrated in vacuo, and used in the subsequent step without further purification, assuming quantitative conversion. LRMS (+ESI) m/z=399.2.

Step 3: 7-(benzyloxy)-N'-(2-(2,4-difluorophenyl)acetyl)-5-isopropyl-6,8-dioxo-3,3a,4,5,6,8-hexahydro-1H-2-oxa-3a1,5-diazaphenalene-9-carbohydrazide

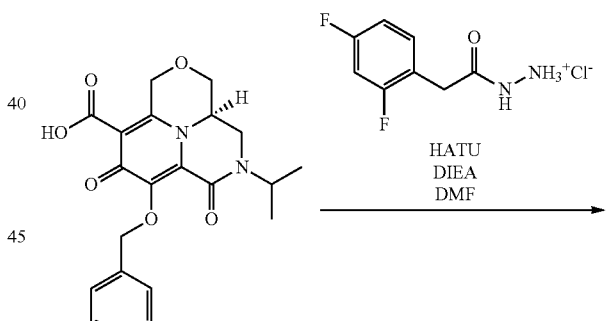

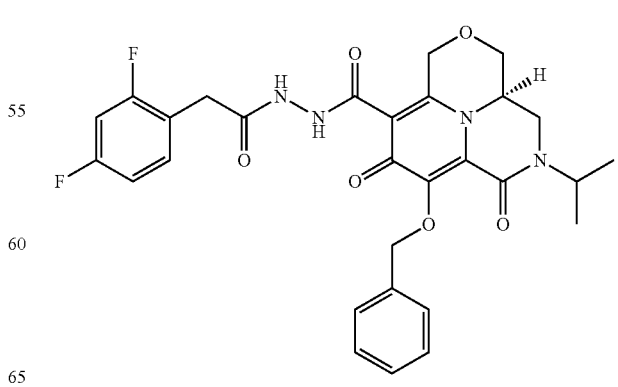

To a solution of unpurified 7-(benzyloxy)-5-isopropyl-6,8-dioxo-3,3a,4,5,6,8-hexahydro-1H-2-oxa-3a1,5-diazaphenalene-9-carboxylic acid (13.5 mg, 0.034 mmol) in DMF (339 μl) was added 2-(2,4-difluorophenyl)acetohydrazide hydrochloride (9.05 mg, 0.041 mmol), DIEA (23.67 μl, 0.136 mmol), and HATU (14.17 mg, 0.037 mmol). The solution was stirred for 10 min at room temperature, and then purified directly by gradient elution on reverse phase (30×150 mm (5 μm) Sunfire Prep C18; 5 to 95% CH$_3$CN/water w/ 0.1% TFA modifier over 20 min at 40 mL/min) to provide the title compound (8.5 mg, 44.3%) as a pale yellow film. LRMS (+ESI) m/z=567.3. $^1$H NMR (400 MHz, CDCl$_3$): δ 12.92 (s, 1H); 8.63 (s, 1H); 7.62 (d, J=7.2 Hz, 2H); 7.25-7.40 (m, 4H); 6.80-6.85 (m, 2H); 5.61 (d, J=18.0 Hz, 1H); 5.23 (d, J=9.4 Hz, 1H); 5.05-5.08 (m, 2H); 4.76-4.79 (m, 1H); 4.02-4.09 (m, 2H); 3.63 (s, 2H); 3.55 (t, J=11.1 Hz, 1H); 3.21 (t, J=12.5 Hz, 1H); 2.94 (d, J=13.7 Hz, 1H); 1.12 (d, J=6.6 Hz, 3H); 1.06 (d, J=6.9 Hz, 3H).

Step 4: 9-(5-(2,4-difluorobenzyl)-1,3,4-thiadiazol-2-yl)-7-hydroxy-5-isopropyl-3,3a,4,5-tetrahydro-1H-2-oxa-3a1,5-diazaphenalene-6,8-dione

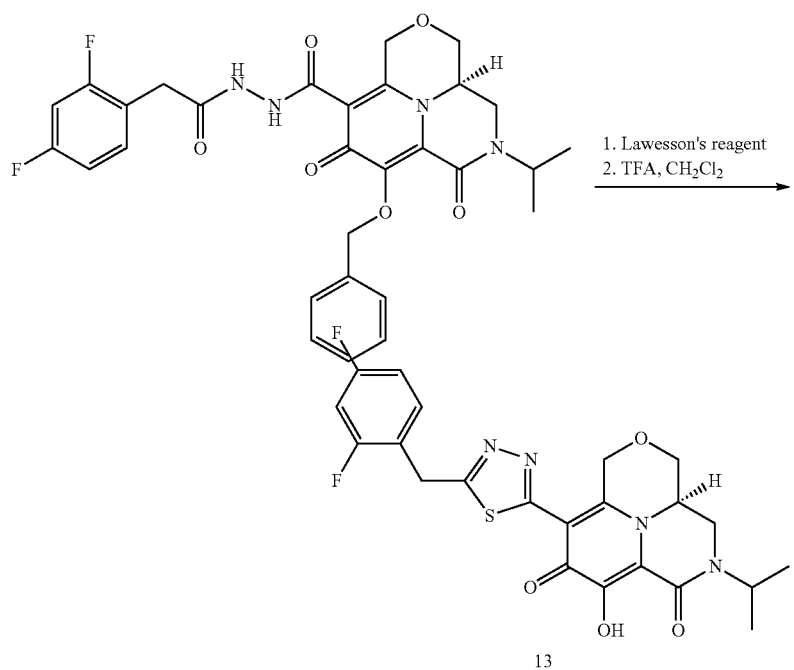

A solution of 7-(benzyloxy)-N'-(2-(2,4-difluorophenyl)acetyl)-5-isopropyl-6,8-dioxo-3,3a,4,5,6,8-hexahydro-1H-2-oxa-3a1,5-diazaphenalene-9-carbohydrazide (8.4 mg, 0.015 mmol) in THF (148 μl) was treated with Lawesson's Reagent (6.60 mg, 0.016 mmol) and stirred at 60° C. overnight. The reaction mixture was concentrated in vacuo, treated with TFA (228 μl, 2.97 mmol), and stirred at 60° C. for 15 minutes. The reaction mixture was again concentrated in vacuo and then purified by gradient elution on reverse phase (30×150 mm (5 um) Sunfire Prep C18; 5 to 95% CH$_3$CN/water w/ 0.1% TFA modifier over 20 min at 40 mL/min) to provide compound 13 (5.5 mg, 75%) as a tan solid. LRMS (+ESI) m/z=475.2. $^1$H NMR (500 MHz, CDCl$_3$): δ 7.34 (d, J=7.8 Hz, 1H); 6.83-6.85 (m, 2H); 5.67 (d, J=18.2 Hz, 1H); 5.20 (d, J=18.2 Hz, 1H); 4.98 (t, J=7.0 Hz, 1H); 4.44 (s, 2H); 4.31 (t, J=15.1 Hz, 2H); 3.84 (t, J=10.3 Hz, 1H); 3.44-3.47 (m, 2H); 1.29 (d, J=7.0 Hz, 3H); 1.25 (d, J=6.5 Hz, 3H).

Example 6

Preparation of Compound 14

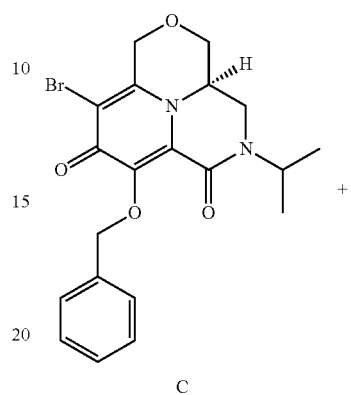

C

+

-continued

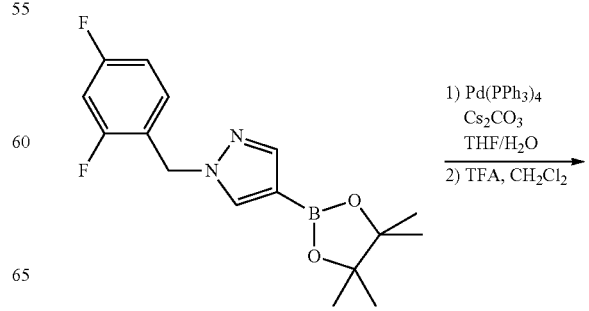

-continued

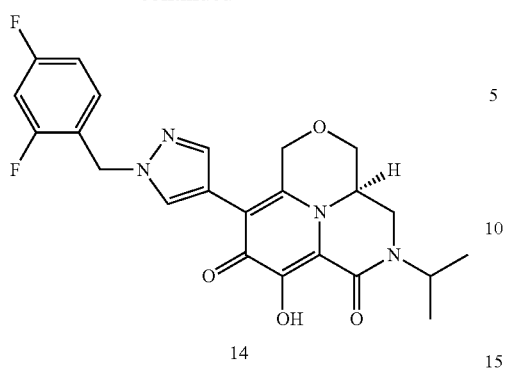

14

A suspension of 7-(benzyloxy)-9-bromo-5-isopropyl-3,3a,4,5-tetrahydro-1H-2-oxa-3a1,5-diazaphenalene-6,8-dione (Example 4, 15 mg, 0.035 mmol), 1-(2,4-difluorobenzyl)-4-(4,4,5,5-tetramethyl-1,3,2-dioxaborolan-2-yl)-1H-pyrazole (22.17 mg, 0.069 mmol), Pd(PPh₃)₄ (4.00 mg, 3.46 μmol) and Cs₂CO₃ (22.56 mg, 0.069 mmol) in THF (700 μl) and water (70 μl) was degassed under a stream of N₂ for 1 min, sealed in a pressure vial, and stirred at 110° C. for 16 hours. Next, the mixture was cooled to room temperature and treated with TFA (500 μl), heated to 60° C., and stirred for 10 min. The mixture was concentrated and purified directly by gradient elution on reverse phase (30×150 mm (5 μm) Sunfire Prep C18; 5 to 95% CH₃CN/water w/ 0.1% TFA modifier over 20 min at 40 mL/min) to provide compound 14 (8.2 g, 52%) as a tan film. LRMS (+ESI) m/z=457.2. ¹H NMR (500 MHz, CDCl₃): δ 8.00 (s, 1H); 7.46 (s, 1H); 7.38-7.40 (m, 1H); 6.82-6.90 (m, 2H); 5.35 (dd, J=19.7, 15.5 Hz, 2H); 4.97-4.98 (m, 1H); 4.86 (d, J=15.7 Hz, 1H); 4.68 (d, J=15.6 Hz, 1H); 4.27 (dd, J=11.8, 4.5 Hz, 1H); 4.19-4.21 (m, 1H); 3.75 (t, J=10.9 Hz, 1H); 3.40 (d, J=7.5 Hz, 2H); 1.25 (d, J=6.9 Hz, 3H); 1.23 (d, J=6.9 Hz, 3H).

Example 7

Preparation of Compound 16

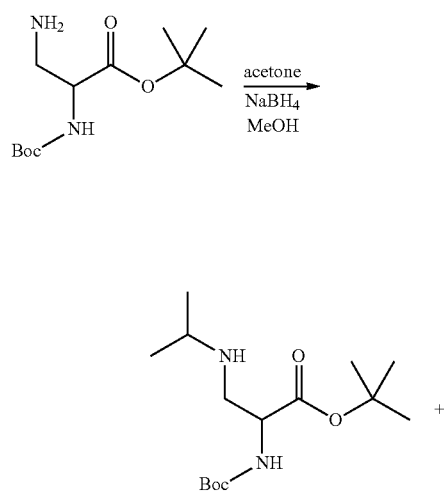

-continued

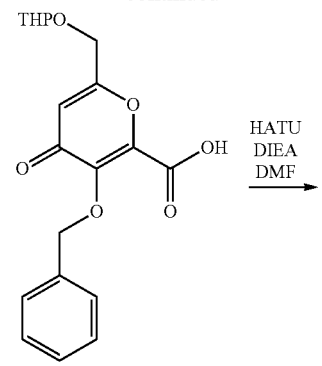

A

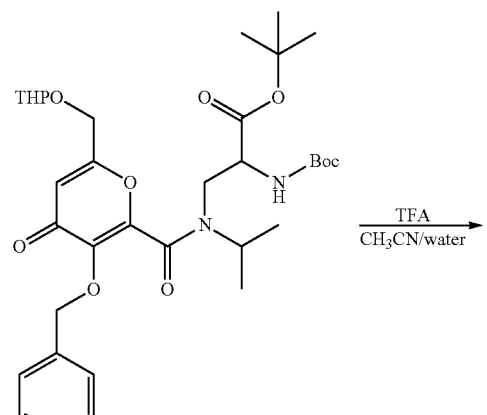

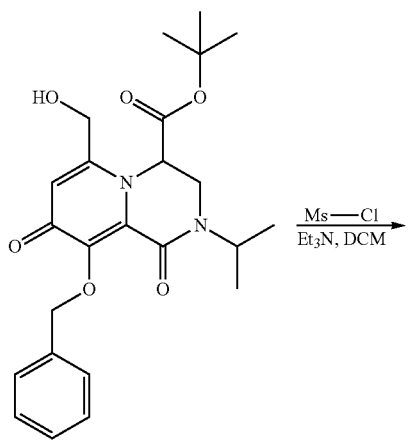

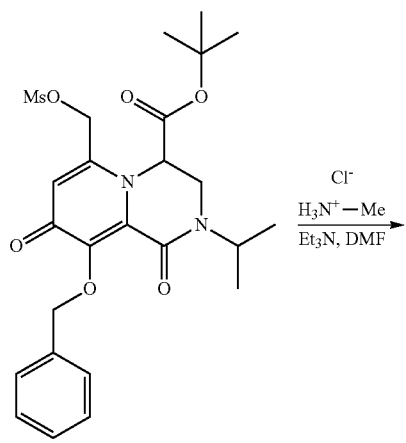

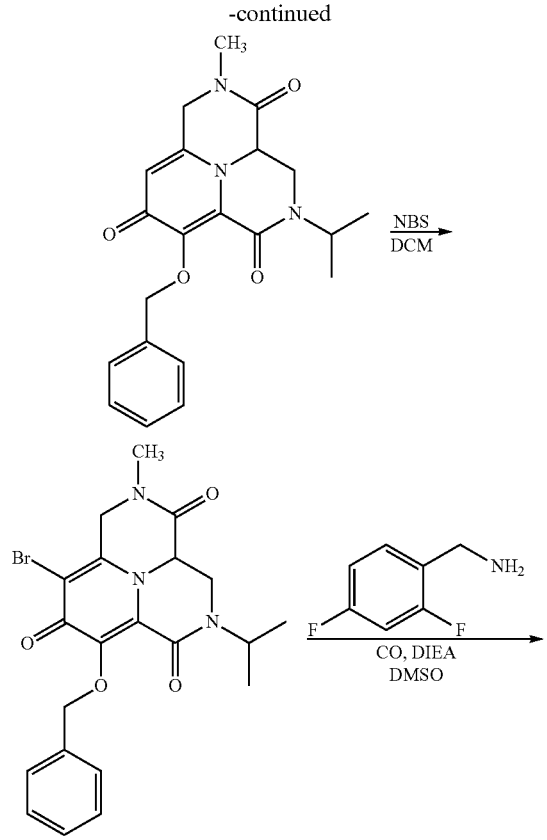

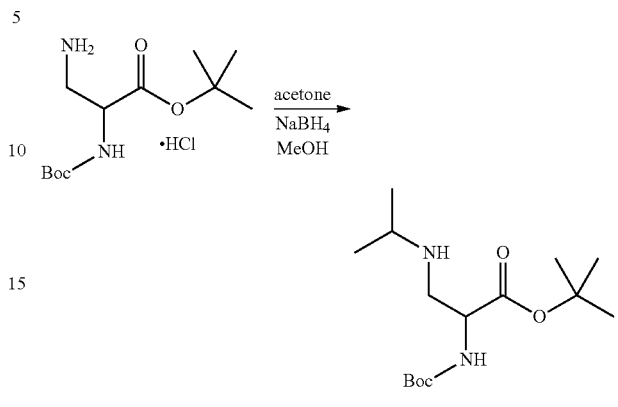

Step 1: tert-butyl 2-((tert-butoxycarbonyl)amino)-3-(isopropylamino)propanoate To tert-butyl 3-amino-2-((tert-butoxycarbonyl)amino) propanoate hydrochloride (16.9 mmol, 5 g) in CH$_3$OH (33.7 mL) was added acetone (84 mmol, 6.2 mL). The resulting mixture was stirred at 50° C. for 16 h. The mixture was cooled to room temperature and NaBH$_4$ (51 mmol, 1.9 g) was added. The resulting mixture was stirred at room temperature for 1 hour. Saturated aqeuous NaHCO$_3$ was added (50 mL) and the mixture was extracted with CH$_2$Cl$_2$ (3×200 mL). The organics were combined and concentrated in vacuo to provide the title compound (5.1 g, 100%) as a colorless oil. LRMS (+ESI) m/z=303.2. 1H NMR (499 MHz, DMSO): δ 6.98 (d, J=8.0 Hz, 1H); 3.92 (d, J=7.5 Hz, 1H); 2.74 (d, J=5.9 Hz, 2H); 2.64 (t, J=7.7 Hz, 1H); 1.39 (app s, 18H); 0.93 (d, J=6.0 Hz, 3H); 0.94 (d, J=6.0 Hz, 3H).

Step 2: tert-butyl 3-(3-(benzyloxy)-N-isopropyl-4-oxo-6-(((tetrahydro-2H-pyran-2-yl)oxy)methyl)-4H-pyran-2-carboxamido)-2-((tert-butoxycarbonyl)amino)propanoate

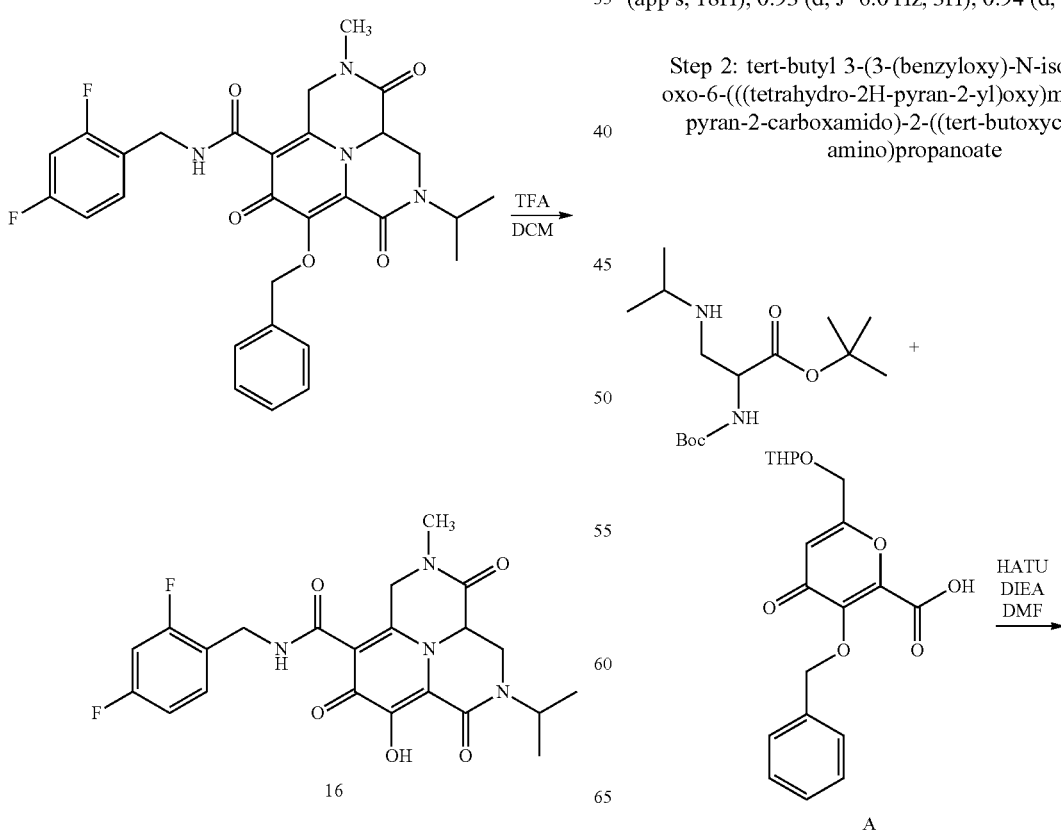

A

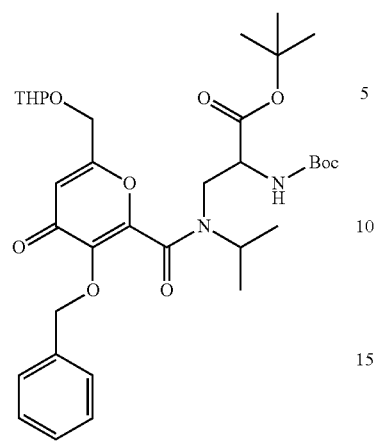

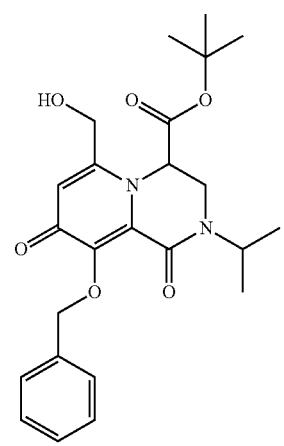

To tert-butyl 2-((tert-butoxycarbonyl)amino)-3-(isopropylamino)propanoate (17 mmol, 5.1 g) in DMF (43.5 mL) was added Intermediate A (13 mmol, 3.6 g) followed by DIEA (39.1 mmol, 6.8 mL) and HATU (19.6 mmol, 7.4 g). The resulting mixture was stirred at room temperature for 10 min. The reaction mixture was diluted with EtOAc (600 mL) and washed sequentially with saturated aqueous NaHCO$_3$ (200 mL) and water (3×200 mL), and the organic layer was separated. The organic layer was dried over MgSO$_4$, filtered and concentrated in vacuo. The residue was purified by gradient elution on SiO$_2$ (330 g SiO$_2$, 0 to 100% EtOAc in hexanes) to provide the title compound (6.5 g, 77%) as a yellow gum. LRMS (+ESI) m/z=645.4.

Step 3: tert-butyl 9-(benzyloxy)-6-(hydroxymethyl)-2-isopropyl-1,8-dioxo-2,3,4,8-tetrahydro-1H-pyrido[1,2-a]pyrazine-4-carboxylate To tert-butyl 3-(3-(benzyloxy)-N-isopropyl-4-oxo-6-(((tetrahydro-2H-pyran-2-yl)oxy)methyl)-4H-pyran-2-carboxamido)-2-((tert-butoxycarbonyl)amino)propanoate (4.9 mmol, 3.5 g) in a 95:5 mixture of CH$_3$CN/water (245 mL) was added concentrated TFA (150 mmol, 11.3 mL). The resulting mixture was stirred at 70° C. for 5 hours. The mixture was cooled to room temperature and diluted with CH$_2$Cl$_2$ (600 mL). The organic layer was carefully neutralized with saturated aqueous NaHCO$_3$, washed sequentially with saturated aqueous NaHCO$_3$ (200 mL) and water (200 mL), and the organic layer was then separated. The organic layer was dried over MgSO$_4$, filtered and concentrated in vacuo to provide the title compound (1.6 g, 73%) as a pale yellow foam which was carried on to the subsequent step without further purification. LRMS (+ESI) m/z=443.3.

Step 4: tert-butyl 9-(benzyloxy)-2-isopropyl-6-(((methylsulfonyl)oxy)methyl)-1,8-dioxo-2,3,4,8-tetrahydro-1H-pyrido[1,2-a]pyrazine-4-carboxylate

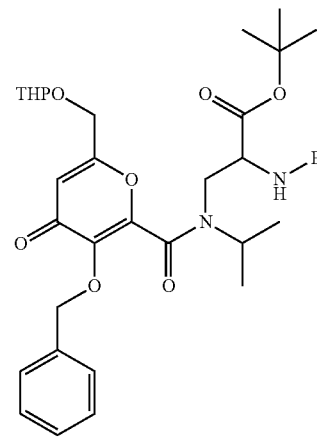

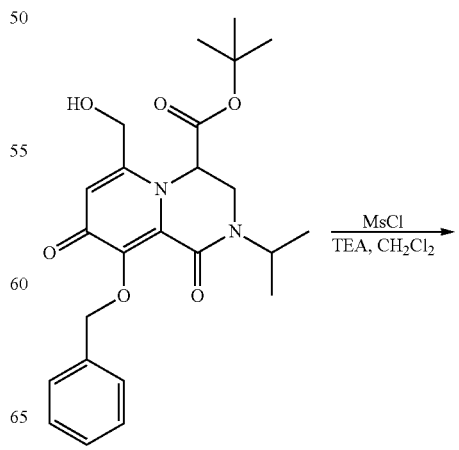

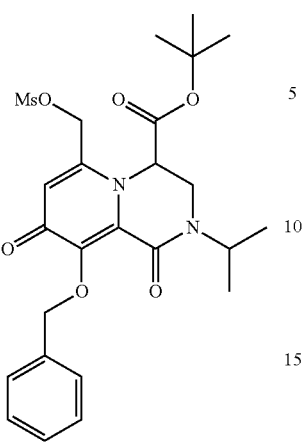

To tert-butyl 9-(benzyloxy)-6-(hydroxymethyl)-2-isopropyl-1,8-dioxo-2,3,4,8-tetrahydro-1H-pyrido[1,2-a]pyrazine-4-carboxylate (3.4 mmol, 1.5 g) in CH$_2$Cl$_2$ (17 mL) cooled to 0° C. was added TEA (8.5 mmol, 1.2 mL) followed by methanesulfonylchloride (4 mmol, 0.3 mL). The resulting mixture was warmed to room temperature and stirred for 5 min. The mixture was diluted with CH$_2$Cl$_2$ (150 mL), washed sequentially with saturated aqueous NaHCO$_3$ (35 mL) and water (35 mL), and the organic layer was separated. The organic layer was dried over MgSO$_4$, filtered and concentrated in vacuo to provide the title compound (1.7 g, 99%) as a pale yellow foam which was carried on to the subsequent step without further purification. LRMS (+ESI) m/z=521.3.

Step 5: 9-(benzyloxy)-2-isopropyl-5-methyl-3,3a,5,6-tetrahydro-2,3a1,5-triazaphenalene-1,4,8(2H)-trione

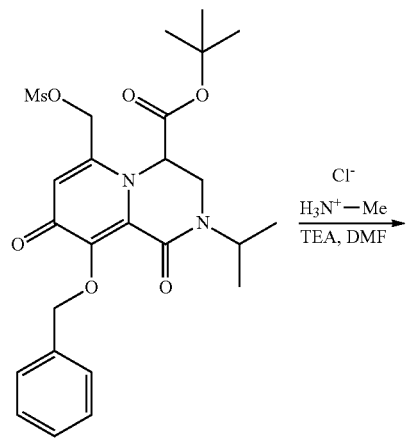

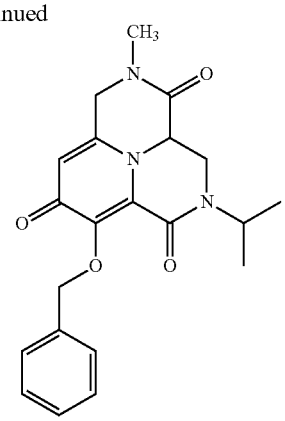

To tert-butyl 9-(benzyloxy)-2-isopropyl-6-(((methylsulfonyl)oxy)methyl)-1,8-dioxo-2,3,4,8-tetrahydro-1H-pyrido[1,2-a]pyrazine-4-carboxylate (3.3 mmol, 1.7 g) in DMF (17 mL) was added methylamine hydrochloride (5 mmol, 340 mg) followed by TEA (10 mmol, 1.4 mL). The resulting mixture was stirred at 70° C. for 2 h. The temperature was then increased to 140° C. and the mixture stirred at that temperature for 16 h. The mixture was cooled to room temperature, diluted with CH$_2$Cl$_2$ (150 mL), washed sequentially with saturated aqueous NaHCO$_3$ (35 mL) and water (35 mL), and the organic layer was separated. The organic layer was dried over MgSO$_4$, filtered and concentrated in vacuo to provide the title compound (1 g, 79%) as a brown foam which was carried on to the subsequent step without further purification. LRMS (+ESI) m/z=382.3.

Step 6: 9-(benzyloxy)-7-bromo-2-isopropyl-5-methyl-3,3a,5,6-tetrahydro-2,3a1,5-triazaphenalene-1,4,8(2H)-trione

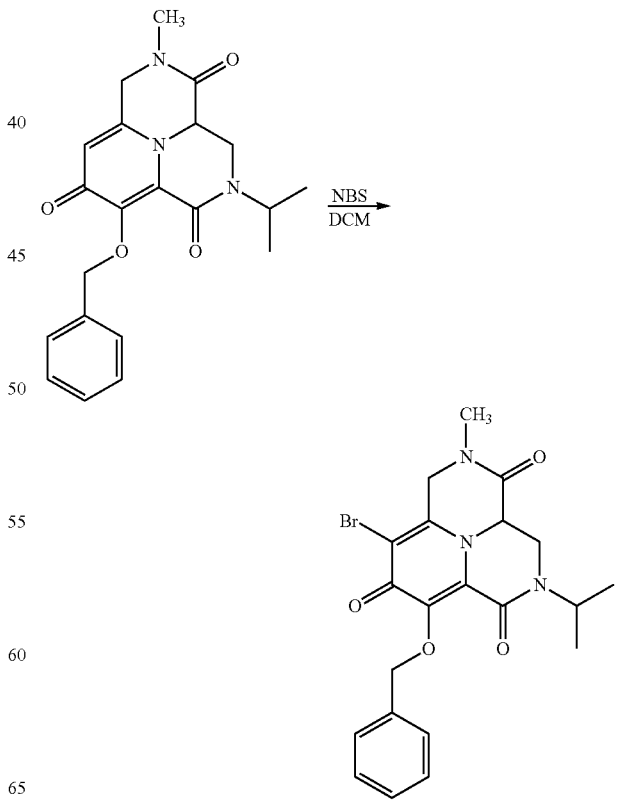

To 9-(benzyloxy)-2-isopropyl-5-methyl-3,3a,5,6-tetrahydro-2,3a1,5-triazaphenalene-1,4,8(2H)-trione (0.1 mmol, 40 mg) in $CH_2Cl_2$ (1 mL) was added NBS (0.1 mmol, 21 mg). The resulting mixture was stirred at room temperature for 5 minutes. The mixture was purified directly by gradient elution on $SiO_2$ (4 g $SiO_2$, 0 to 15% $CH_3OH$ in $CH_2Cl_2$) to provide the title compound (44 mg, 91%) as a yellow solid. LRMS (+ESI) m/z=462.1. 1H NMR (500 MHz, $CDCl_3$): δ 7.60 (d, J=7.3 Hz, 2H); 7.32 (dt, J=14.3, 7.2 Hz, 3H); 5.35 (d, J=9.9 Hz, 1H); 5.10 (d, J=9.8 Hz, 1H); 4.88-4.90 (m, 1H); 4.77 (d, J=17.2 Hz, 1H); 4.54 (t, J=16.0 Hz, 2H); 4.07 (dd, J=14.3, 3.4 Hz, 1H); 3.50 (t, J=13.0 Hz, 1H); 3.08 (s, 3H); 1.23 (d, J=6.8 Hz, 3H); 1.20 (d, J=6.8 Hz, 3H).

Step 7: 9-(benzyloxy)-N-(2,4-difluorobenzyl)-2-isopropyl-5-methyl-1,4,8-trioxo-1,2,3,3a,4,5,6,8-octahydro-2,3a1,5-triazaphenalene-7-carboxamide

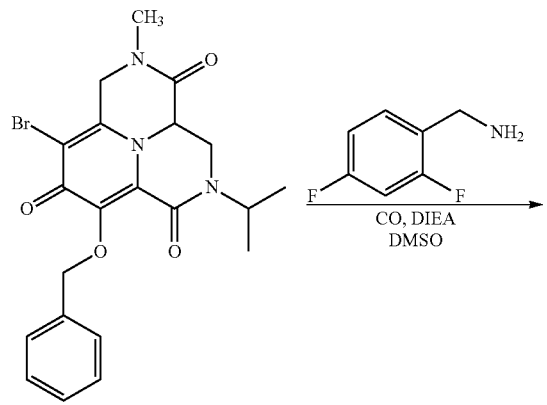

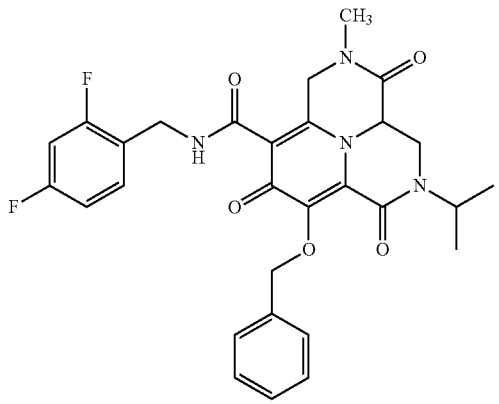

To 9-(benzyloxy)-7-bromo-2-isopropyl-5-methyl-3,3a,5,6-tetrahydro-2,3a1,5-triazaphenalene-1,4,8(2H)-trione (0.1 mmol, 42 mg) in DMSO (3 mL) was added 2,4-difluorobenzylamine (0.4 mmol, 52 mg), DIEA (0.5 mmol, 80 μL) and $Pd(PPh_3)_4$ (0.04 mmol, 42 mg) under nitrogen. The resulting mixture was evacuated and purged three times with $CO_{(g)}$ and stirred at 100° C. under a $CO_{(g)}$ atmosphere (balloon) overnight. The mixture was concentrated under a stream of nitrogen to remove volatiles and then purified directly by reverse phase chromatography (SunFire™ Prep C18 OBD™ 5 μm 30×150 mm column; 10 to 70% $CH_3CN$/water with 0.1% TFA modifier over 20 min) to provide the title compound (22 mg, 44%) as a white solid. LRMS (+ESI) m/z=551.3.

Step 8: N-(2,4-difluorobenzyl)-9-hydroxy-2-isopropyl-5-methyl-1,4,8-trioxo-1,2,3,3a,4,5,6,8-octahydro-2,3a1,5-triazaphenalene-7-carboxamide

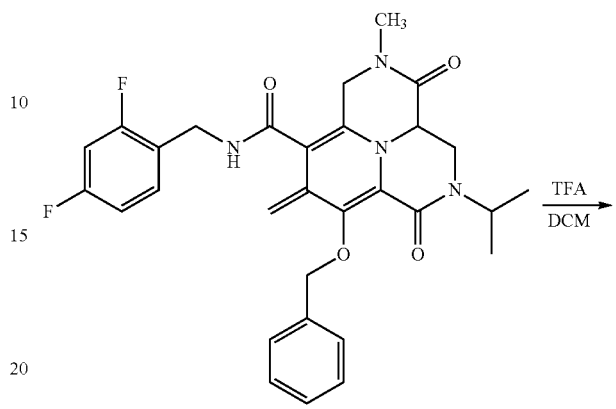

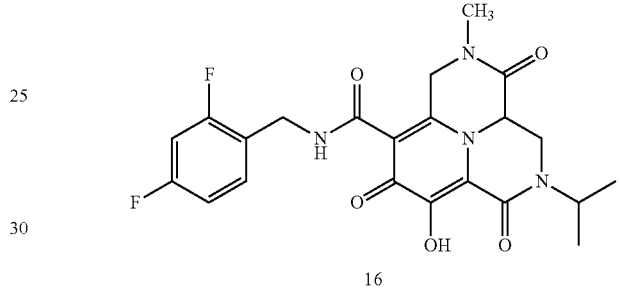

To 9-(benzyloxy)-N-(2,4-difluorobenzyl)-2-isopropyl-5-methyl-1,4,8-trioxo-1,2,3,3a,4,5,6,8-octahydro-2,3a1,5-triazaphenalene-7-carboxamide (0.04 mmol, 22 mg) in $CH_2Cl_2$ (1 mL) was added concentrated TFA (6.5 mmol, 500 μL). The resulting mixture was stirred at room temperature for 2 hours. The mixture was concentrated under a stream of $N_2$ to remove volatiles and then purified by reverse phase chromatography (SunFire™ Prep C18 OBD™ 5 μm 30×150 mm column; 10 to 70% $CH_3CN$/water with 0.1% TFA modifier over 20 minutes) to provide compound 16 (8 mg, 43%) as a white solid. LRMS (+ESI) m/z=461.2. 1H NMR (500 MHz, $CDCl_3$): δ 10.79 (s, 1H); 7.36 (q, J=7.6 Hz, 1H); 6.81-6.84 (m, 2H); 5.96 (d, J=19.3 Hz, 1H); 4.92-4.93 (m, 1H); 4.83 (d, J=19.3 Hz, 1H); 4.61 (t, J=13.6 Hz, 3H); 4.29 (dd, J=14.2, 4.0 Hz, 1H); 3.57 (dd, J=14.2, 12.0 Hz, 1H); 3.17 (s, 3H); 1.31 (d, J=6.8 Hz, 3H); 1.27 (d, J=6.8 Hz, 3H).

Example 8

Preparation of Compound 17

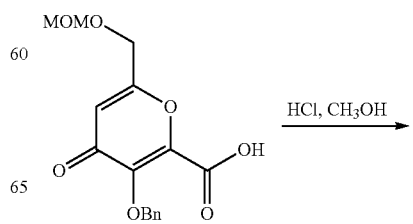

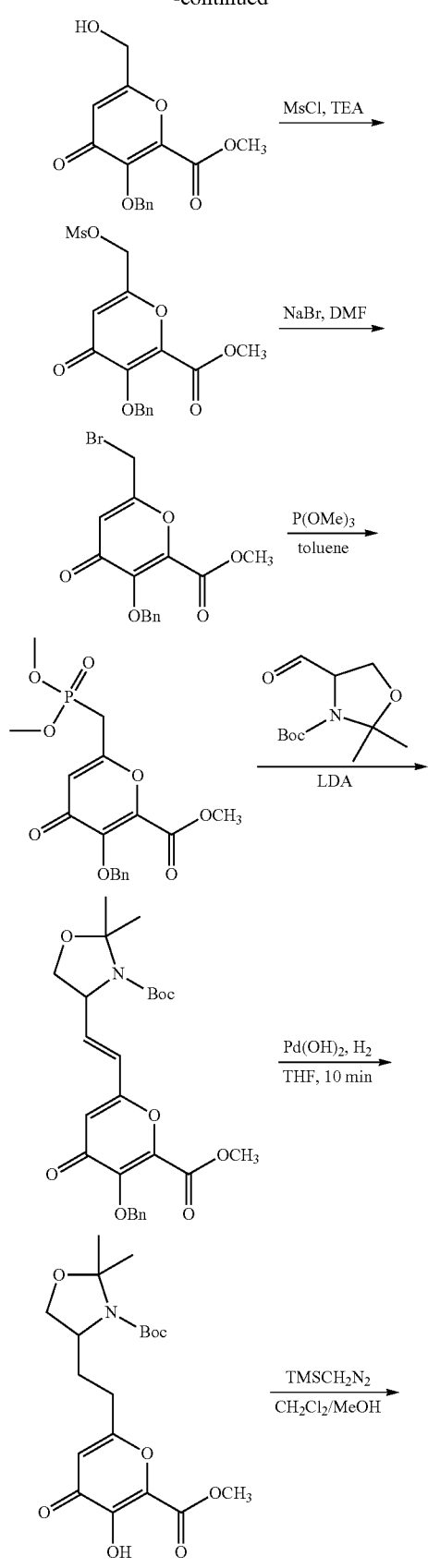
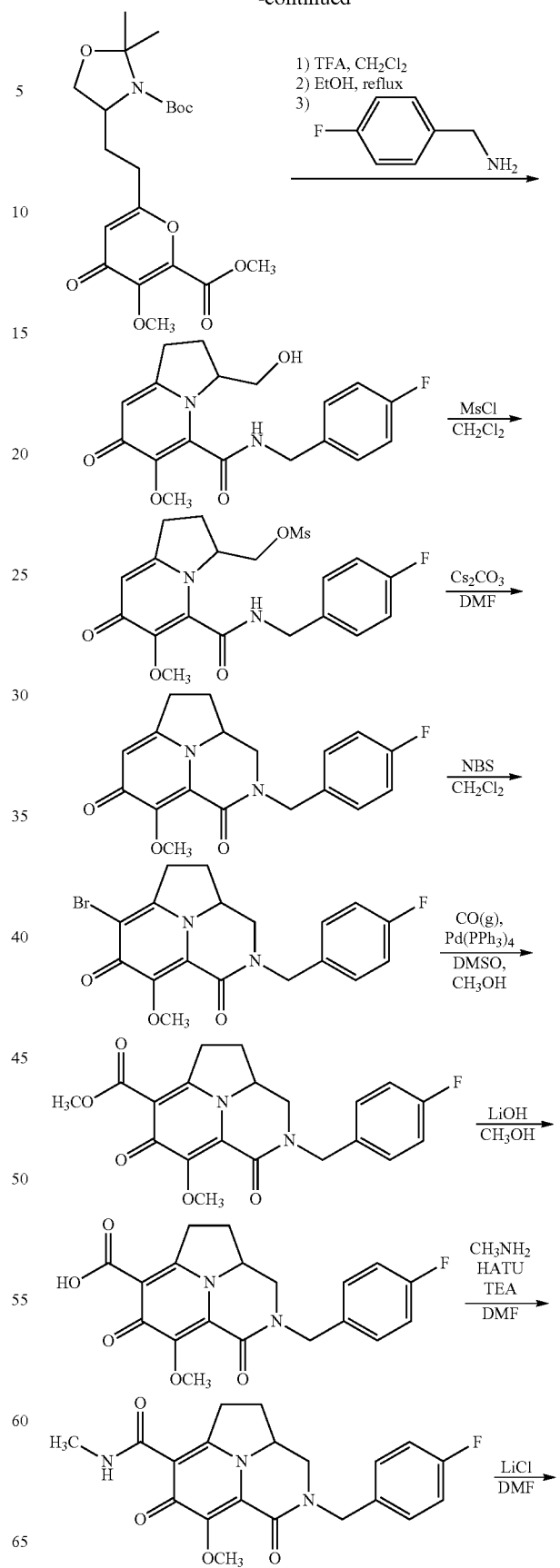

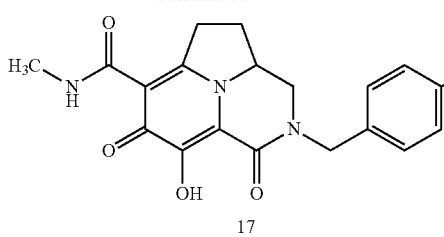

17

Step 1: methyl 3-(benzyloxy)-6-(hydroxymethyl)-4-oxo-4H-pyran-2-carboxylate

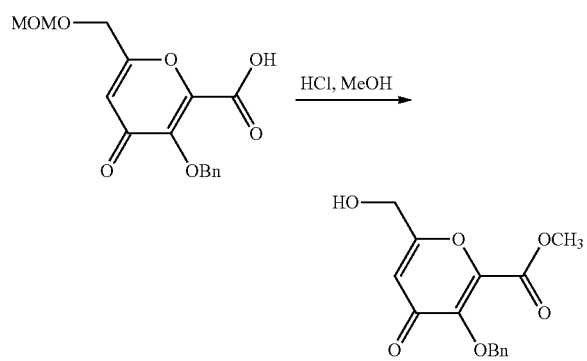

3-(benzyloxy)-6-((methoxymethoxy)methyl)-4-oxo-4H-pyran-2-carboxylic acid was prepared according to the synthetic route outlined in U.S. Pat. No. 7,211,572 (S. Miyazaki, inventor; 2007 May 1). Intermediate Compound A from Example 1 can be used interchangeably with this starting material in the subsequent chemistry.

To a solution of 3-(benzyloxy)-6-((methoxymethoxy)methyl)-4-oxo-4H-pyran-2-carboxylic acid (4.0 g, 12.5 mmol) in CH$_3$OH (35 mL) was added 4 N HCl in CH$_3$OH (35 mL) at 0° C. The resulting mixture was stirred at room temperature for 6 h. The reaction mixture was concentrated in vacuo, diluted with water (50 mL), extracted with EtOAc (3×100 mL), dried over Na$_2$SO$_4$, and the organic phase concentrated in vacuo to provide the title compound (3.0 g, 83%) which was carried on to the subsequent step without further purification. LRMS (+ESI) m/z: 291.1. $^1$H NMR (400 MHz, CDCl$_3$) δ 7.45-7.43 (m, 1H); 7.38-7.34 (m, 4H); 6.61 (s, 1H); 5.28 (s, 2H); 4.53 (s, 2H); 3.86 (s, 3H).

Step 2: methyl 3-(benzyloxy)-6-(((methylsulfonyl)oxy)methyl)-4-oxo-4H-pyran-2-carboxylate

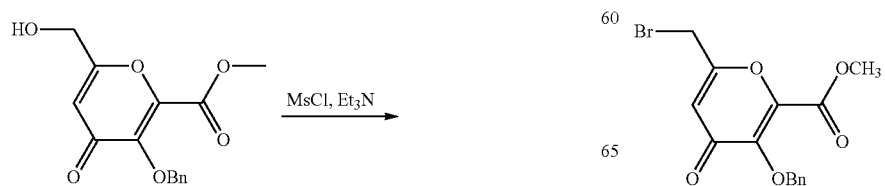

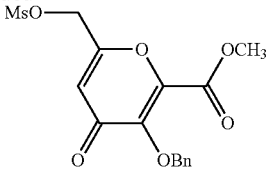

To a stirred solution of methyl 3-(benzyloxy)-6-(hydroxymethyl)-4-oxo-4H-pyran-2-carboxylate (5 g, 17.2 mmol) in CH$_2$Cl$_2$ (100 mL) was added TEA (4.6 mL, 34.4 mmol) and methanesulfonyl chloride (2.1 mL, 25.8 mmol) at 0° C. After stirring for 2 h at room temperature, the mixture was diluted with CH$_2$Cl$_2$ (50 mL) and washed with brine (30 mL). The organic layer was dried over Na$_2$SO$_4$, and concentrated to provide the title compound (5.3 g, 84%) which was carried on to the subsequent step without further purification. LRMS (+ESI) m/z: 369.1.

Step 3: methyl 3-(benzyloxy)-6-(bromomethyl)-4-oxo-4H-pyran-2-carboxylate

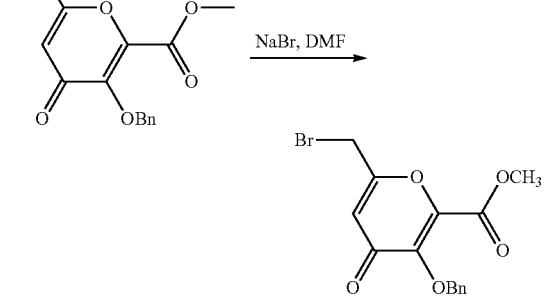

To a stirred solution of methyl 3-(benzyloxy)-6-(((methylsulfonyl)oxy)-methyl)-4-oxo-4H-pyran-2-carboxylate (5.3 g, 14.4 mmol) in DMF (35 mL) was added NaBr (2.9 g, 28.8 mmol) at room temperature. After further stirring for 50 min, the reaction mixture was poured into water (100 mL) and extracted by EtOAc (3×100 mL). The organic layer was dried over Na$_2$SO$_4$, and concentrated in vacuo. The residue was purified by gradient elution on SiO$_2$ (200 g SiO$_2$, 0 to 10% EtOAc in hexanes) to provide the title compound (4 g, 81%). LRMS (+ESI) m/z: 354.0. $^1$H NMR (400 MHz, CDCl$_3$) δ 7.45-7.46 (m, 2H); 7.34-7.36 (m, 3H); 6.53 (s, 1H); 5.30 (s, 2H); 4.19 (s, 2H); 3.80 (s, 3H).

Step 4: methyl 3-(benzyloxy)-6-((dimethoxyphosphoryl)methyl)-4-oxo-4H-pyran-2-carboxylate

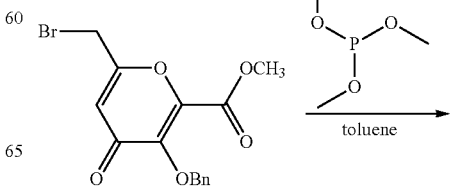

-continued

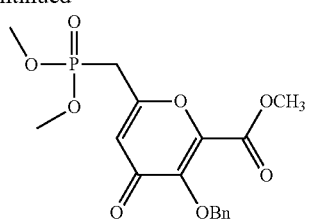

To a solution of methyl 3-(benzyloxy)-6-(bromomethyl)-4-oxo-4H-pyran-2-carboxylate (4 g, 11.2 mmol) in toluene (100 mL) was added trimethyl phosphite (10 mL, 112 mmol) and the mixture was heated to reflux for 86 h. Excess trimethyl phosphite was removed by distillation and the resulting oily residue was purified by gradient elution on SiO$_2$ (180 g SiO$_2$, 50% to 10% EtOAc in hexanes) to provide the title compound (3.4 g, 79%) as a yellow oil. LRMS (+ESI) m/z: 383.1. $^1$H NMR (400 MHz, CDCl$_3$) δ 7.45-7.46 (m, 2H); 7.32-7.35 (m, 3H); 6.43 (s, 1H); 5.29 (s, 2H); 3.80 (s, 3H); 3.78 (s, 6H); 3.10 (s, 2H).

Step 5: tert-butyl 4-(2-(5-(benzyloxy)-6-(methoxycarbonyl)-4-oxo-4H-pyran-2-yl)vinyl)-2,2-dimethyloxazolidine-3-carboxylate

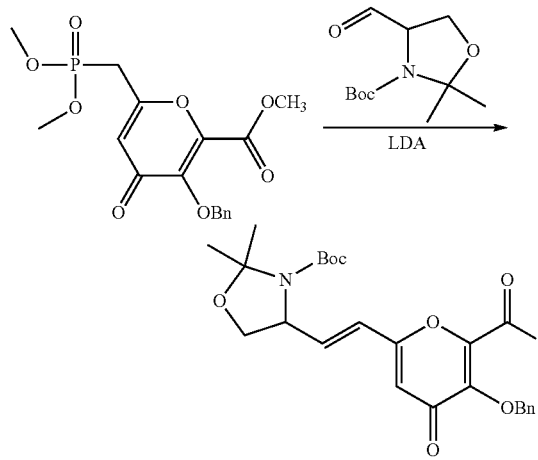

To solution of methyl 3-(benzyloxy)-6-((dimethoxyphosphoryl)methyl)-4-oxo-4H-pyran-2-carboxylate (500 mg, 1.30 mmol) in THF (5 mL) was added a 1.88 M THF solution of LDA (0.8 mL, 1.50 mmol) under N$_2$ and then the mixture was stirred at −78° C. for 30 min. Then tert-butyl 4-formyl-2,2-dimethyloxazolidine-3-carboxylate (300 mg, 1.30 mmol) in THF (5 mL) was added and the mixture was stirred at the same temperature for 2 h. The mixture was quenched by addition of aqueous 1 N HCl and concentrated to dryness in vacuo. The residue was purified by gradient elution on SiO$_2$ (10 g SiO$_2$, 0% to 30% EtOAc in hexanes) to provide the title compound (358 mg, 58%) as a yellow oil. LRMS (+ESI) m/z: 486.2. $^1$H NMR (400 MHz, CDCl$_3$) δ 7.45-7.47 (m, 2H); 7.30-7.37 (m, 3H); 6.59-6.66 (m, 1H); 6.31 (s, 1H); 6.1-56.27 (m, 2H); 5.31 (s, 2H); 4.44-4.57 (m, 3H); 4.08-4.15 (m, 1H); 3.87 (s, 1H); 1.42-1.66 (m, 15H).

Step 6: tert-butyl 4-(2-(5-hydroxy-6-(methoxycarbonyl)-4-oxo-4H-pyran-2-yl) ethyl)-2,2-dimethyloxazolidine-3-carboxylate

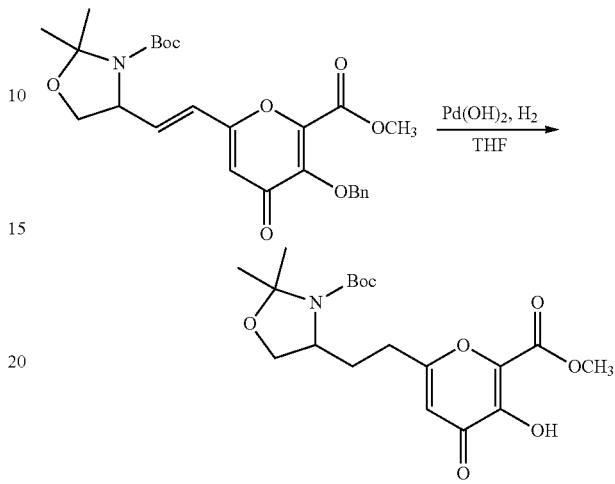

A mixture of (E)-tert-butyl 4-(2-(5-(benzyloxy)-6-(methoxycarbonyl)-4-oxo-4H-pyran-2-yl)vinyl)-2,2-dimethyloxazolidine-3-carboxylate (485 mg, 1.0 mmol) and 10% Pd(OH)$_2$ on carbon (100 mg) in THF (2 mL) was stirred at room temperature under an atmosphere of H$_2$ (balloon) for 20 min. The mixture was filtered and the filtrate was concentrated in vacuo to provide the title compound (350 mg, 95%), which was carried on to the subsequent step without further purification. LRMS (+ESI) m/z: 398.2.

Step 7: tert-butyl 4-(2-(5-methoxy-6-(methoxycarbonyl)-4-oxo-4H-pyran-2-yl)ethyl)-2,2-dimethyloxazolidine-3-carboxylate

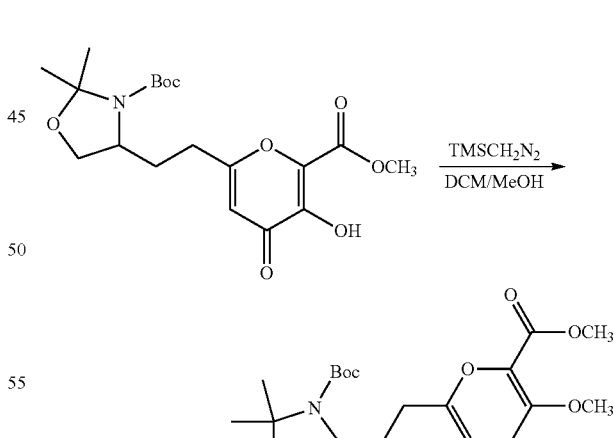

A mixture of tert-butyl 4-(2-(5-hydroxy-6-(methoxycarbonyl)-4-oxo-4H-pyran-2-yl)ethyl)-2,2-dimethyloxazolidine-3-carboxylate (500 mg, 2.60 mmol) in 1:1 CH$_2$Cl$_2$/CH$_3$OH (10 mL) and TMSCH$_2$N$_2$ (5 mL, 10.0 mmol) was stirred at room temperature for 2 h. The reaction mixture was dissolved in water (30 mL) and extracted with EtOAc (3×20 mL). The organic layer was dried over Na$_2$SO$_4$ and concentrated in vacuo. The resulting residue was purified by gradient elution on SiO$_2$ (10 g SiO$_2$, 0% to 20% EtOAc in hexanes) to provide the title compound (420 mg, 81%) as a solid. LRMS (+ESI) m/z: 412.2. $^1$H NMR (400 MHz, CDCl$_3$) δ 6.29-6.33 (m, 1H); 3.98 (s, 3H); 3.89 (s, 3H); 3.72-3.81 (m, 3H); 2.54-2.61 (m, 2H); 1.9-22.08 (m, 2H); 1.65 (s, 9H); 1.43 (s, 6H).

Step 8: N-(4-fluorobenzyl)-3-(hydroxymethyl)-6-methoxy-7-oxo-1,2,3,7-tetrahydro indolizine-5-carboxamide

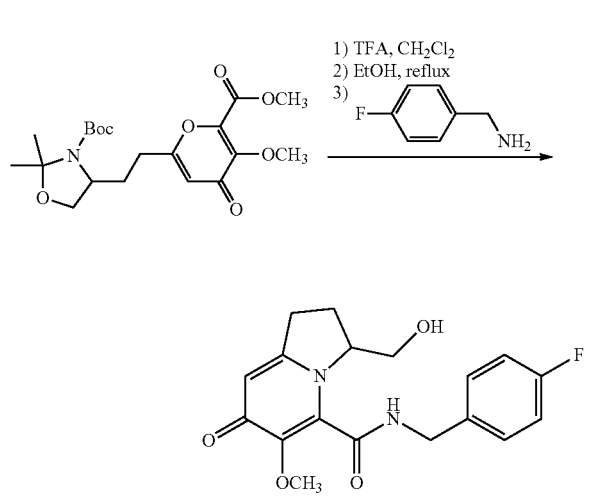

To a mixture of tert-butyl 4-(2-(5-methoxy-6-(methoxycarbonyl)-4-oxo-4H-pyran-2-yl)ethyl)-2,2-dimethyloxazolidine-3-carboxylate (500 mg, 1.21 mmol) in CH$_2$Cl$_2$ (25 mL) was added TFA (6 mL) at 0° C. Then the mixture was stirred at the room temperature for 2 h, concentrated under reduced pressure, and carried on to the subsequent step without further purification. MS (+ESI) m/z: 272.1.

A solution of unpurified methyl 6-(3-amino-4-hydroxybutyl)-3-methoxy-4-oxo-4H-pyran-2-carboxylate (320 mg, 1.21 mmol) in EtOH (15 mL) was heated to reflux for 2 h, concentrated under reduced pressure, and carried on to the subsequent step without further purification. MS (+ESI) m/z: 282.3.

To a solution of crude 7-ethoxy-3-(hydroxymethyl)-6-methoxy-5-(methoxy carbonyl)-2,3-dihydro-1H-indolizin-4-ium (300 mg, 1.12 mmol) in EtOH (5 mL) was added (4-fluorophenyl)methanamine (423 mg, 3.6 mmol) and the mixture was irradiated in a microwave reactor at 80° C. for 30 min. The reaction mixture was concentrated in vacuo and the mixture was purified directly by reverse phase chromatography (Synergi™ Max-RP C18 4 μm 30×150 mm column; 1 to 25% CH$_3$CN/water with 0.075% TFA modifier over 8 minutes) to provide the title compound (300 mg, 72% over 3 steps) as a yellow oil. LRMS (+ESI) m/z: 347.1. $^1$H NMR (400 MHz, CDCl$_3$) δ 8.01 (s, 1H); 7.44-7.48 (m, 2H); 7.01-7.09 (m, 2H); 6.67 (m, 1H); 4.88 (s, 1H); 4.51-4.64 (m, 2H); 3.80 (s, 3H); 3.65-3.78 (m, 2H); 2.88-3.01 (m, 2H); 2.29-2.46 (m, 2H).

Step 9: (5-((4-fluorobenzyl)carbamoyl)-6-methoxy-7-oxo-1,2,3,7-tetrahydro indolizin-3-yl)methyl methanesulfonate

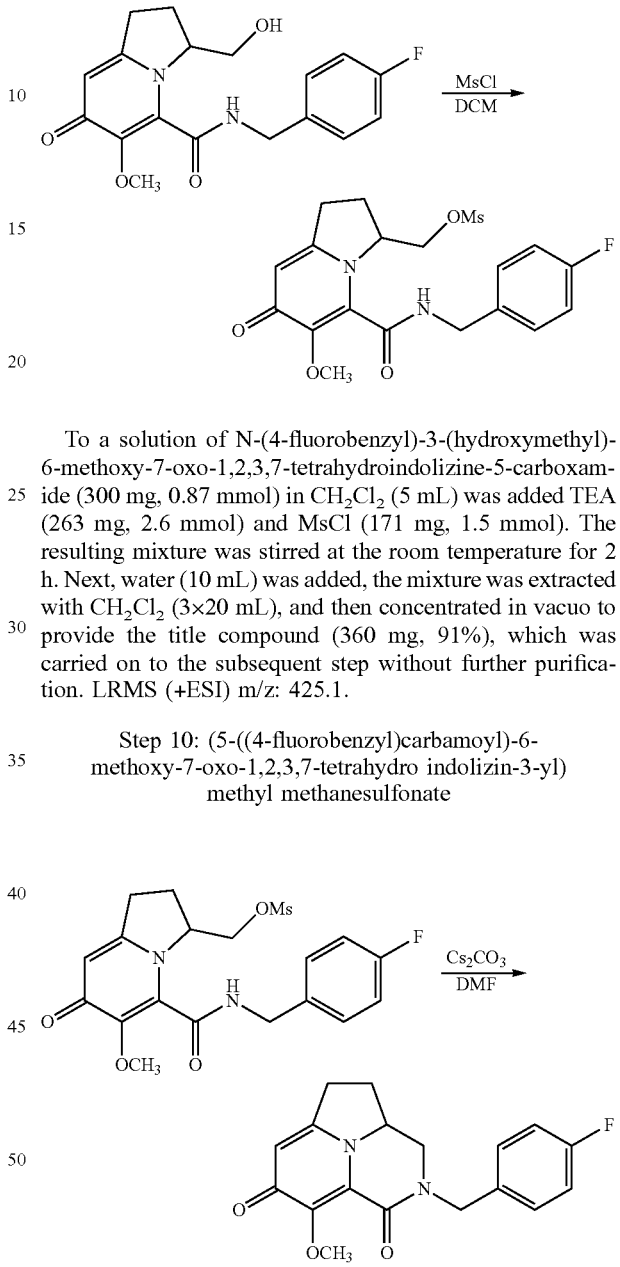

To a solution of N-(4-fluorobenzyl)-3-(hydroxymethyl)-6-methoxy-7-oxo-1,2,3,7-tetrahydroindolizine-5-carboxamide (300 mg, 0.87 mmol) in CH$_2$Cl$_2$ (5 mL) was added TEA (263 mg, 2.6 mmol) and MsCl (171 mg, 1.5 mmol). The resulting mixture was stirred at the room temperature for 2 h. Next, water (10 mL) was added, the mixture was extracted with CH$_2$Cl$_2$ (3×20 mL), and then concentrated in vacuo to provide the title compound (360 mg, 91%), which was carried on to the subsequent step without further purification. LRMS (+ESI) m/z: 425.1.

Step 10: (5-((4-fluorobenzyl)carbamoyl)-6-methoxy-7-oxo-1,2,3,7-tetrahydro indolizin-3-yl) methyl methanesulfonate A mixture of Cs$_2$CO$_3$ (530 mg, 1.5 mmol) in DMF (5 mL) was stirred at 105° C. for 30 min. Next, (5-((4-fluorobenzyl)carbamoyl)-6-methoxy-7-oxo-1,2,3,7-tetrahydroindolizin-3-yl)methyl methanesulfonate (220 mg, 0.54 mmol) in DMF (3 mL) was added dropwise, and the mixture was stirred for 2 h. The mixture was cooled to room temperature, water (10 mL) was added, and the reaction mixture was extracted with CH$_2$Cl$_2$ (4×20 mL), and concentrated in vacuo. The resulting residue was purified by preparative thin layer chromatography (CH$_2$Cl$_2$/MeOH=10:1) to provide the title compound (100 mg, 58%) as a yellow oil. LRMS (+ESI) m/z: 329.1. $^1$H NMR (400 MHz, CDCl$_3$) δ 7.31-7.33 (m, 2H);

7.04-7.08 (m, 2H); 6.92 (s, 1H); 5.00 (s, 1H); 4.43-4.47 (m, 2H); 3.71 (s, 3H); 3.56-3.70 (m, 2H); 3.12-3.16 (m, 2H); 2.45-2.47 (m, 1H); 1.94-2.00 (m, 1H).

Step 11: 6-bromo-2-(4-fluorobenzyl)-8-methoxy-3,3a,4,5-tetrahydro-1H-pyrazino[2,1,6-cd]indolizine-1,7(2H)-dione

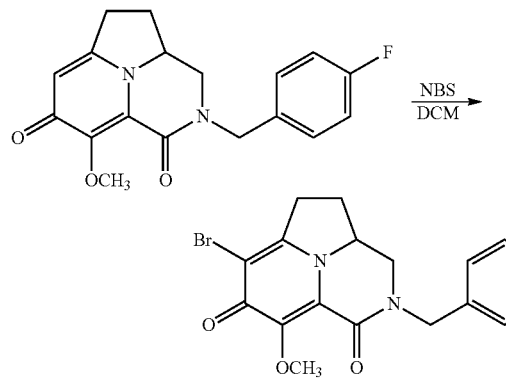

To a solution of (5-((4-fluorobenzyl)carbamoyl)-6-methoxy-7-oxo-1,2,3,7-tetrahydroindolizin-3-yl)methyl methanesulfonate (100 mg, 0.303 mmol) in CH$_2$Cl$_2$ (10 mL) was added anhydrous NBS (179 mg, 1.0 mmol). The mixture was stirred at room temperature for 2 hours. The resulting residue was purified by preparative thin layer chromatography (CH$_2$Cl$_2$/CH$_3$OH=10:1) to provide the title compound (100 mg, 80.6%) as a solid. LRMS (+ESI) m/z: 409.0. $^1$H NMR (400 MHz, CDCl$_3$) δ 7.31-7.33 (m, 2H); 7.02-7.06 (m, 2H); 4.93 (s, 1H); 4.00-4.47 (m, 2H); 3.73 (s, 3H); 3.50-3.70 (m, 2H); 3.00-3.24 (m, 2H); 2.37-2.39 (m, 1H); 2.05-2.10 (m, 1H).

Step 12: methyl 2-(4-fluorobenzyl)-8-methoxy-1,7-dioxo-2,3,3a,4,5,7-hexahydro-1H-pyrazino[2,1,6-cd]indolizine-6-carboxylate

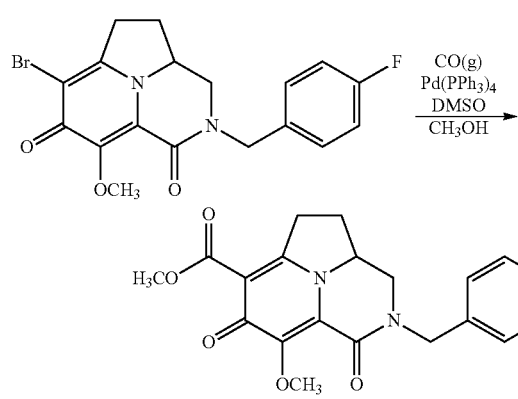

To a solution of 6-bromo-2-(4-fluorobenzyl)-8-methoxy-3,3a,4,5-tetrahydro-1H-pyrazino[2,1,6-cd]indolizine-1,7(2H)-dione (100 mg, 0.25 mmol) in ~1:4 DMSO/CH$_3$OH (5 mL) was added DIEA (129 mg, 1.0 mmol) and Pd(PPh$_3$)$_4$ (23 mg, 0.02 mmol). The resulting mixture was stirred at 80° C. for 16 h under a balloon of CO$_{(g)}$. The resulting residue was purified by preparative thin layer chromatography (CH$_2$Cl$_2$/CH$_3$OH=10:1) to provide the title compound (40 mg, 42%) as a white solid. LRMS (+ESI) m/z: 387.1.

Step 13: 2-(4-fluorobenzyl)-8-methoxy-1,7-dioxo-2,3,3a,4,5,7-hexahydro-1H-pyrazino[2,1,6-cd]indolizine-6-carboxylic acid

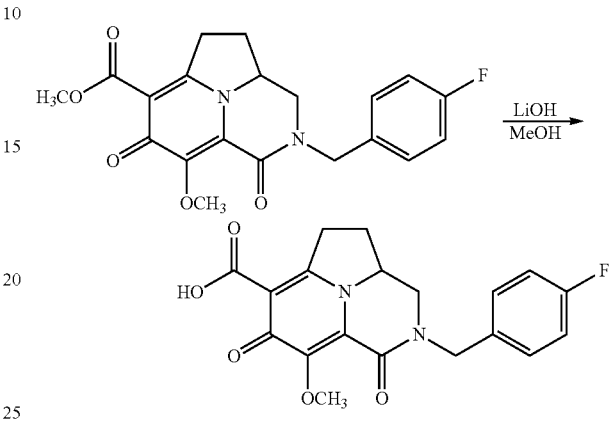

To a solution of methyl 2-(4-fluorobenzyl)-8-methoxy-1,7-dioxo-2,3,3a,4,5,7-hexahydro-1H-pyrazino[2,1,6-cd]indolizine-6-carboxylate (150 mg, 0.386 mmol) in CH$_3$OH (10 mL) was added aqueous 1 N LiOH (1.2 mL). The resulting solution was stirred at room temperature for 2 h. To the reaction mixture was added water (10 mL) and it was then extracted with CH$_2$Cl$_2$ (4×15 mL), and concentrated in vacuo to provide the title compound (120 mg, 83%), which was carried on to the subsequent step without further purification. LRMS (+ESI) m/z: 373.1.

Step 14: 2-(4-fluorobenzyl)-8-methoxy-N-methyl-1,7-dioxo-2,3,3a,4,5,7-hexahydro-1H-pyrazino[2,1,6-cd]indolizine-6-carboxamide

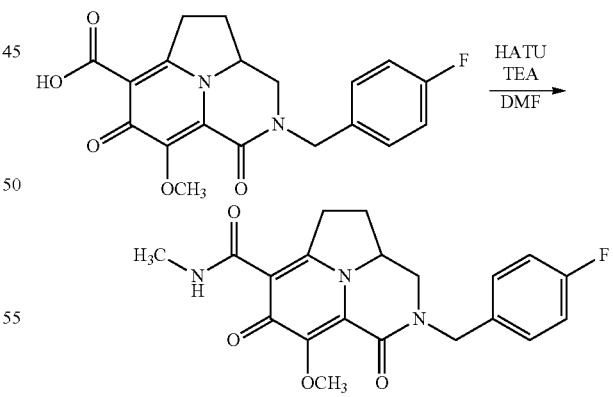

To a solution of 2-(4-fluorobenzyl)-8-methoxy-1,7-dioxo-2,3,3a,4,5,7-hexahydro-1H-pyrazino[2,1,6-cd]indolizine-6-carboxylic acid (120 mg, 0.322 mmol) in DMF (8 mL) was added HATU (380 mg, 1.0 mmol) and TEA (150 mg, 1.5 mmol). The resulting mixture was stirred at room temperature for 16 h. EtOAc (20 mL) and water (20 mL) were added, the reaction mixture extracted with EtOAc (3×15 mL), washed with brine (2×10 mL), and the combined the organic layers dried over Na₂SO₄ and concentrated in vacuo. The resulting residue was purified by preparative thin layer chromatography (CH₂Cl₂/CH₃OH=10:1) to provide the title compound (100 mg, 80%). LRMS (+ESI) m/z: 386.1.

Step 15: 2-(4-fluorobenzyl)-8-hydroxy-N-methyl-1,7-dioxo-2,3,3a,4,5,7-hexahydro-1H-pyrazino[2,1,6-cd]indolizine-6-carboxamide

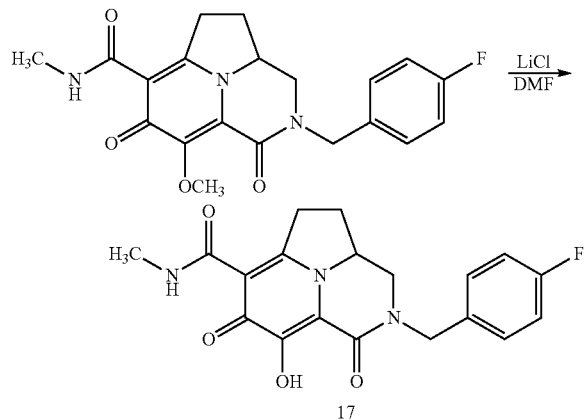

17

To a solution of 2-(4-fluorobenzyl)-8-methoxy-N-methyl-1,7-dioxo-2,3,3a,4,5,7-hexahydro-1H-pyrazino[2,1,6-cd]indolizine-6-carboxamide (100 mg, 0.26 mmol) in DMF (3 mL) was added anhydrous LiCl (40 mg, 1.0 mmol). The resulting solution was heated to 110° C. for 2 h under N₂ with stirring. The reaction mixture was purified directly by reverse phase chromatography (YMC™ Actus Triart C18 150×30 mm; 27 to 57% CH₃CN/water with 0.075% TFA modifier over 8 min) to provide compound 17 (33 mg, 33%) as a white solid. LRMS (+ESI) m/z: 372.1. ¹H NMR (400 MHz, MeOD) δ 7.33-7.43 (m, 2H); 7.08-7.13 (m, 2H); 4.75-4.83 (m, 3H); 3.81-3.91 (m, 2H); 3.58-3.70 (m, 2H); 2.90 (s, 3H); 2.45 (s, 1H); 1.90 (s, 1H).

Example 9

Preparation of Compound 18

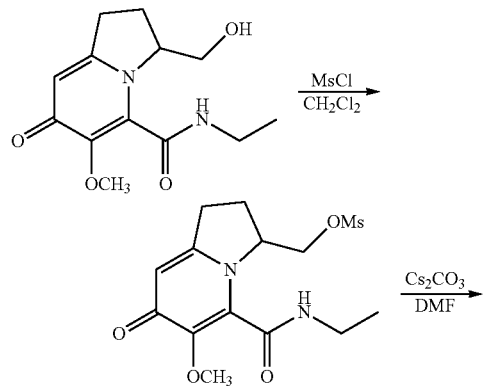

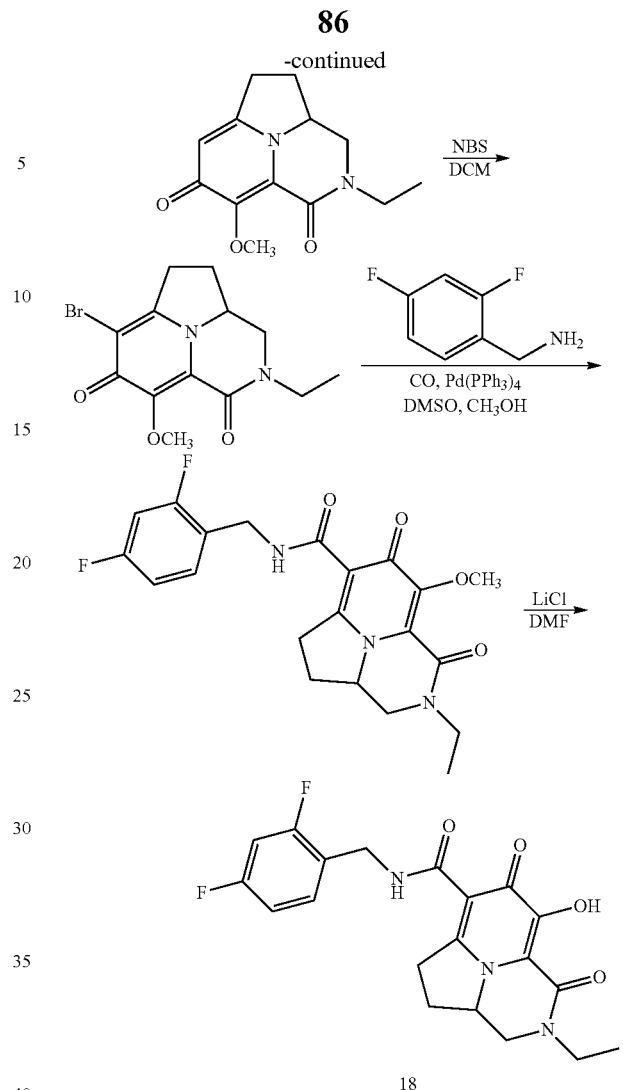

18

Step 1: (5-(ethylcarbamoyl)-6-methoxy-7-oxo-1,2,3,7-tetrahydroindolizin-3-yl) methyl methanesulfonate

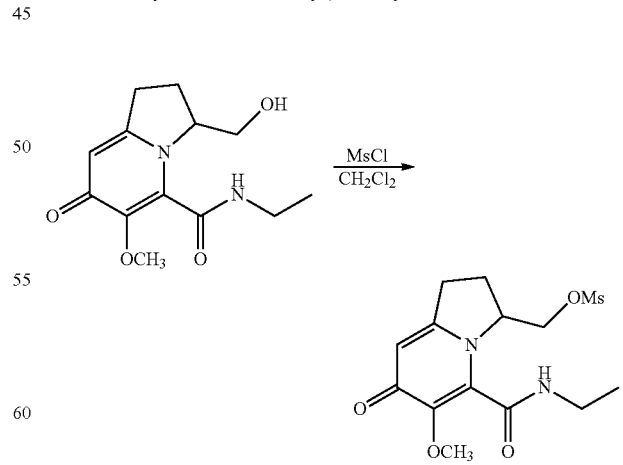

N-ethyl-3-(hydroxymethyl)-6-methoxy-7-oxo-1,2,3,7-tetrahydroindolizine-5-carboxamide was prepared according to the route detailed in Example 8, substituting ethylamine for benzylamine.

To a solution of N-ethyl-3-(hydroxymethyl)-6-methoxy-7-oxo-1,2,3,7-tetrahydroindolizine-5-carboxamide (330 mg, 1.23 mmol) in CH$_2$Cl$_2$ (15 mL) was added TEA (400 mg, 4.0 mmol) and MsCl (285 mg, 2.5 mmol), and the mixture was stirred at room temperature for 2 h. Water (20 mL) was added and the reaction mixture was extracted with CH$_2$Cl$_2$ (3×100 mL), and then concentrated in vacuo to provide the title compound (300 mg, 70%), which was carried on to the subsequent step without further purification. LRMS (+ESI) m/z: 345.1.

Step 2: 2-ethyl-8-methoxy-3,3a,4,5-tetrahydro-1H-pyrazino[2,1,6-cd]indolizine-1,7(2H)-dione

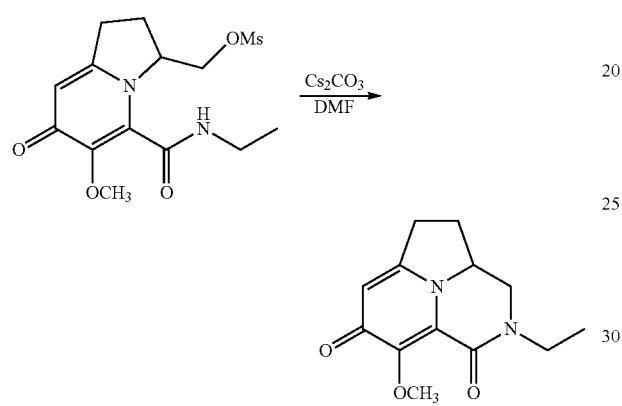

A mixture of Cs$_2$CO$_3$ (530 mg, 1.5 mmol) in DMF (5 mL) was stirred at 105° C. for 30 min. Next, (5-(ethylcarbamoyl)-6-methoxy-7-oxo-1,2,3,7-tetrahydroindolizin-3-yl)methyl methanesulfonate (300 mg, 0.87 mmol) in DMF (10 mL) was added dropwise, and the mixture was stirred at the room temperature for 2 h. The mixture was cooled to room temperature, water (50 mL) was added, the reaction mixture was extracted with CH$_2$Cl$_2$ (3×30 mL), and then concentrated in vacuo. The resulting residue was purified by preparative thin layer chromatography (CH$_2$Cl$_2$/CH$_3$OH=10:1) to provide the title compound (130 mg, 61%) as a yellow oil. LRMS (+ESI) m/z: 249.1. $^1$H NMR (400 MHz, CDCl$_3$) δ 7.19 (s, 1H); 4.94-4.99 (m, 1H); 3.97 (s, 3H); 3.66-3.70 (m, 2H); 3.63-3.65 (m, 2H); 3.37-3.39 (m, 2H); 2.63-2.69 (m, 1H); 2.11-2.17 (m, 1H); 1.24-1.27 (m, 3H).

Step 3: 6-bromo-2-ethyl-8-methoxy-3,3a,4,5-tetrahydro-1H-pyrazino[2,1,6-cd]indolizine-1,7(2H)-dione

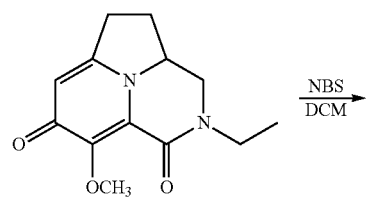

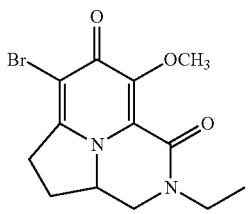

To a solution of 2-ethyl-8-methoxy-3,3a,4,5-tetrahydro-1H-pyrazino[2,1,6-cd]indolizine-1,7(2H)-dione (130 mg, 0.53 mmol) in CH$_2$Cl$_2$ (10 mL) was added NBS (179 mg, 1.0 mmol). The mixture was stirred at the room temperature for 2 h. The reaction mixture was purified directly by preparative thin layer chromatography (CH$_2$Cl$_2$/CH$_3$OH=10:1) to provide the title compound (160 mg, 93%) as a yellow solid. LRMS (+ESI) m/z: 328.0. $^1$H NMR: (400 MHz, CDCl$_3$) δ 4.54-4.56 (m, 1H), 4.03 (s, 3H), 3.60-3.73 (m, 4H), 3.26-3.33 (m, 2H), 2.47-2.49 (m, 1H), 2.05-2.09 (m, 1H), 1.21-1.27 (m, 3H).

Step 4: N-(2,4-difluorobenzyl)-2-ethyl-8-methoxy-1,7-dioxo-2,3,3a,4,5,7-hexahydro-1H-pyrazino[2,1,6-cd]indolizine-6-carboxamide

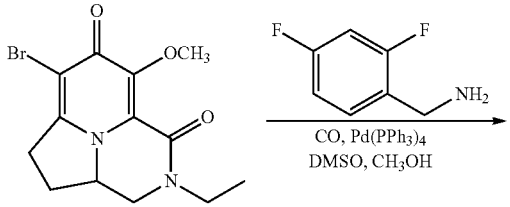

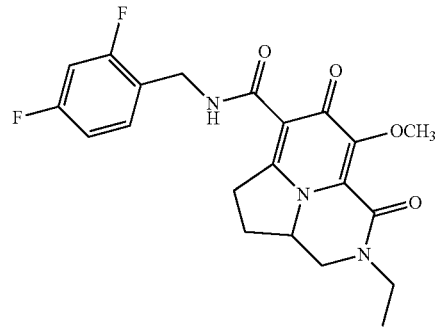

To a solution of 6-bromo-2-ethyl-8-methoxy-3,3a,4,5-tetrahydro-1H-pyrazino[2,1,6-cd]indolizine-1,7(2H)-dione (160 mg, 0.48 mmol) in DMSO/CH$_3$OH (1 mL/4 mL) was added DIEA (205 mg, 1.05 mmol), (2,4-difluorophenyl)methanamine (143 mg, 1.0 mmol), and Pd(PPh$_3$)$_4$ (23 mg, 0.02 mmol). The mixture was stirred at 80° C. under an atmosphere of CO$_{(g)}$ (balloon) for 16 h. The reaction mixture was purified directly by preparative thin layer chromatography (CH$_2$Cl$_2$/CH$_3$OH=10:1) to provide the title compound (50 mg, 24.5%) as a yellow solid. LRMS (+ESI) m/z: 418.2.

Step 5: N-(2,4-difluorobenzyl)-2-ethyl-8-hydroxy-1,7-dioxo-2,3,3a,4,5,7-hexahydro-1H-pyrazino[2,1,6-cd]indolizine-6-carboxamide

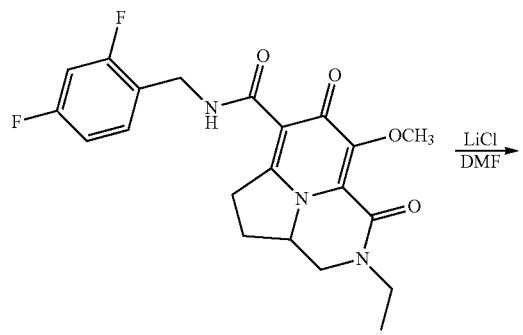

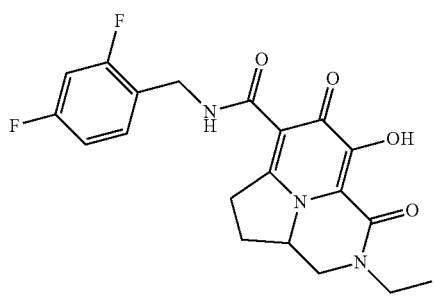

18

To a solution of N-(2,4-difluorobenzyl)-2-ethyl-8-methoxy-1,7-dioxo-2,3,3a,4,5,7-hexahydro-1H-pyrazino[2,1,6-cd]indolizine-6-carboxamide (50 mg, 0.117 mmol) in DMF (3 mL) was added anhydrous LiCl (20 mg, 0.5 mmol). The resulting solution was heated at 110° C. for 2 h under N₂ with stirring. The reaction mixture was purified directly by reverse phase chromatography (YMC™ Actus Triart C18 150×30 mm; 31 to 61% CH₃CN/water with 0.075% TFA modifier over 8 min) to provide compound 18 (27 mg, 56.5%) as a white solid. MS (+ESI) m/z: 404.1. ¹H NMR (400 MHz, DMSO-d₆) δ 11.30 (s, 1H); 10.89 (s, 1H); 7.36-7.37 (m, 1H); 7.19-7.22 (m, 1H); 7.04-7.06 (m, 1H); 4.54-4.65 (m, 3H); 3.74-3.84 (m, 4H); 2.54-2.56 (m, 3H); 1.82-1.84 (m, 1H); 1.10-1.14 (m, 3H).

Example 10

Preparation of Compound 24

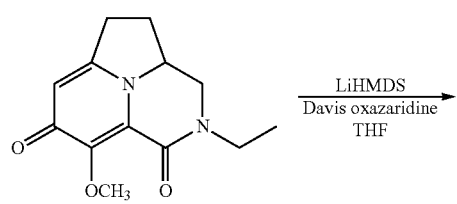

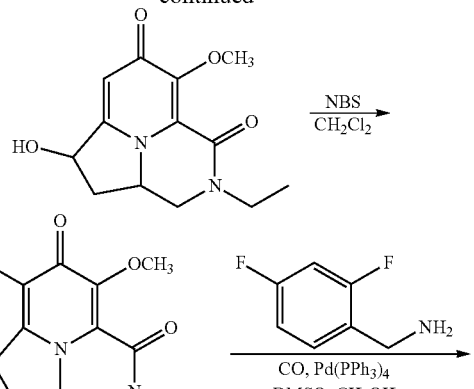

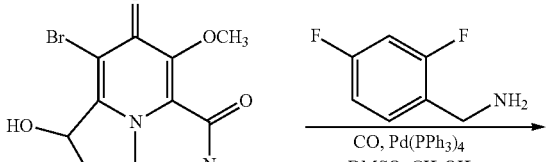

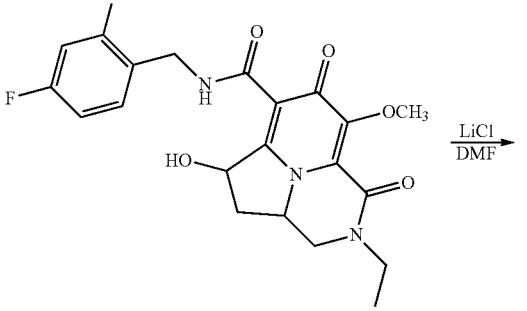

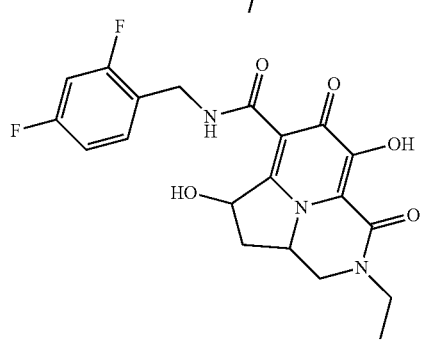

24

Step 1: 2-ethyl-5-hydroxy-8-methoxy-3,3a,4,5-tetrahydro-1H-pyrazino[2,1,6-cd]indolizine-1,7(2H)-dione

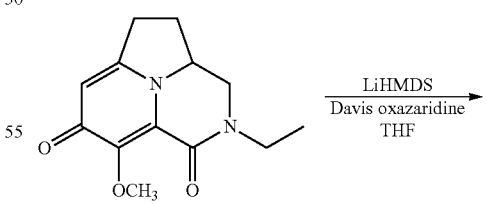

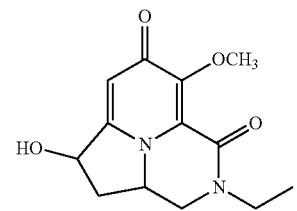

To a stirred solution of 2-ethyl-8-methoxy-3,3a,4,5-tetrahydro-1H-pyrazino[2,1,6-cd]indolizine-1,7(2H)-dione (Example 9, 150 mg, 0.60 mmol) in dry THF (30 mL) cooled to −78° C. under N₂ was added a 1 N THF solution of LiHMDS (1.8 mL, 1.8 mmol). After 1 h, Davis oxaziridine (224 mg, 1.0 mmol) in THF (100 mL) was slowly added, the mixture warmed slowly to room temperature, and then stirred for 1 h. The reaction was quenched with saturated aqueous NH₄Cl (10 mL), and the mixture was extracted with EtOAc (3×20 mL). The combined extracts were washed with water (2×20 mL) and brine (3×20 mL), concentrated in vacuo, and the resulting residue was purified by preparative thin layer chromatography (CH₂Cl₂/CH₃OH=8:1) to provide the title compound (70 mg, 46%) as a mixture of diastereomers. MS (+ESI) m/z: 265.1. ¹H NMR: (400 MHz, CH₃OD) δ 6.64 (s, 1H); 5.17-5.18 (m, 1H); 3.90 (s, 3H); 3.82-3.85 (m, 1H); 3.65-3.70 (m, 4H); 2.41-2.45 (m, 1H); 2.20-2.21 (m, 1H); 1.25-1.27 (m, 3H).

Step 2: 6-bromo-2-ethyl-5-hydroxy-8-methoxy-3,3a,4,5-tetrahydro-1H-pyrazino[2,1,6-cd]indolizine-1,7(2H)-dione

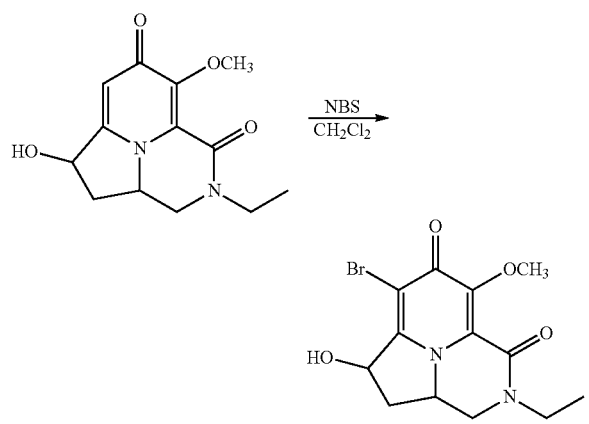

To a solution of 2-ethyl-5-hydroxy-8-methoxy-3,3a,4,5-tetrahydro-1H-pyrazino[2,1,6-cd]indolizine-1,7(2H)-dione (70 mg, 0.27 mmol) in CH₂Cl₂ (10 mL) was added anhydrous NBS (179 mg, 1.0 mmol). The mixture was stirred at room temperature for 2 h. The mixture was concentrated in vacuo and then purified directly by preparative thin layer chromatography (CH₂Cl₂/CH₃OH=10:1) to provide the title compound (75 mg, 83%) as a yellow solid. MS (+ESI) m/z: 344.0. ¹H NMR (400 MHz, CH₃OD) δ 5.37-5.42 (m, 1H); 4.97-5.00 (m, 1H); 3.92 (s, 3H); 3.62-3.73 (m, 4H); 2.62-2.46 (m, 1H); 2.19-2.27 (m, 1H); 1.23-1.27 (m, 3H).

Step 3: N-(2,4-difluorobenzyl)-2-ethyl-5-hydroxy-8-methoxy-1,7-dioxo-2,3,3a,4,5,7-hexahydro-1H-pyrazino[2,1,6-cd]indolizine-6-carboxamide

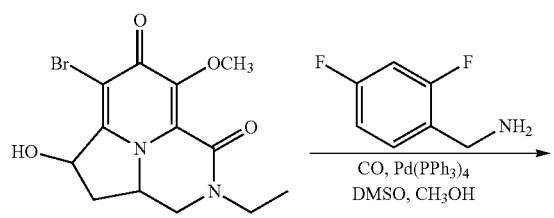

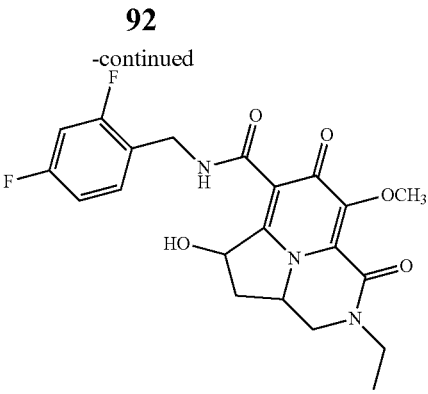

To a solution of 6-bromo-2-ethyl-5-hydroxy-8-methoxy-3,3a,4,5-tetrahydro-1H-pyrazino[2,1,6-cd]indolizine-1,7(2H)-dione (75 mg, 0.22 mmol) in DMSO/CH₃OH (1.5/6 mL) was added DIEA (205 mg, 1.00 mmol), (2,4-difluorophenyl)methanamine (143 mg, 1.0 mmol) and Pd(PPh₃)₄ (23 mg, 0.02 mmol). The mixture was stirred at 80° C. under an atmosphere of CO₍g₎ (balloon) for 16 h. The mixture was concentrated in vacuo, and then purified directly by preparative thin layer chromatography (CH₂Cl₂/CH₃OH=8:1) to provide the title compound (40 mg, 51%) as a pale yellow solid. MS (+ESI) m/z: 434.1.

Step 4: N-(2,4-difluorobenzyl)-2-ethyl-5,8-dihydroxy-1,7-dioxo-2,3,3a,4,5,7-hexahydro-1H-pyrazino[2,1,6-cd]indolizine-6-carboxamide

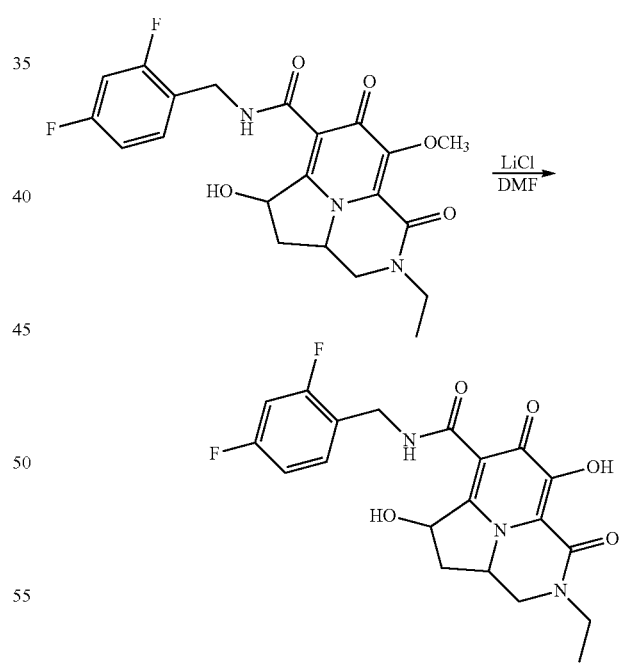

24

To a solution of N-(2,4-difluorobenzyl)-2-ethyl-5-hydroxy-8-methoxy-1,7-dioxo-2,3,3a,4,5,7-hexahydro-1H-pyrazino[2,1,6-cd]indolizine-6-carboxamide (45 mg, 0.103 mmol) in DMF (3 mL) was added anhydrous LiCl (20 mg, 0.5 mmol). The resulting solution was heated at 110° C. for 2 h under N₂ with stirring. The reaction mixture was purified directly by reverse phase chromatography (Synergi™ Max- RP C18 4 um 30×150 mm column; 25 to 55% CH₃CN/water with 0.075% TFA modifier over 8 minutes) to provide compound 24 (9.5 mg, 21.3%) as a white solid. MS (+ESI) m/z: 420.1. ¹H NMR (400 MHz, DMSO-d₆) δ 11.04 (s, 1H); 10.86 (s, 1H); 7.41-7.44 (m, 1H); 7.25-7.27 (m, 1H); 7.08-7.09 (m, 1H); 5.78-5.79 (m, 1H); 4.53-4.57 (m, 3H); 3.62-3.63 (m, 5H); 2.23-2.28 (m, 1H); 2.10-2.13 (m, 1H); 1.12-1.16 (m, 3H).

Example 11

Preparation of Compound 26

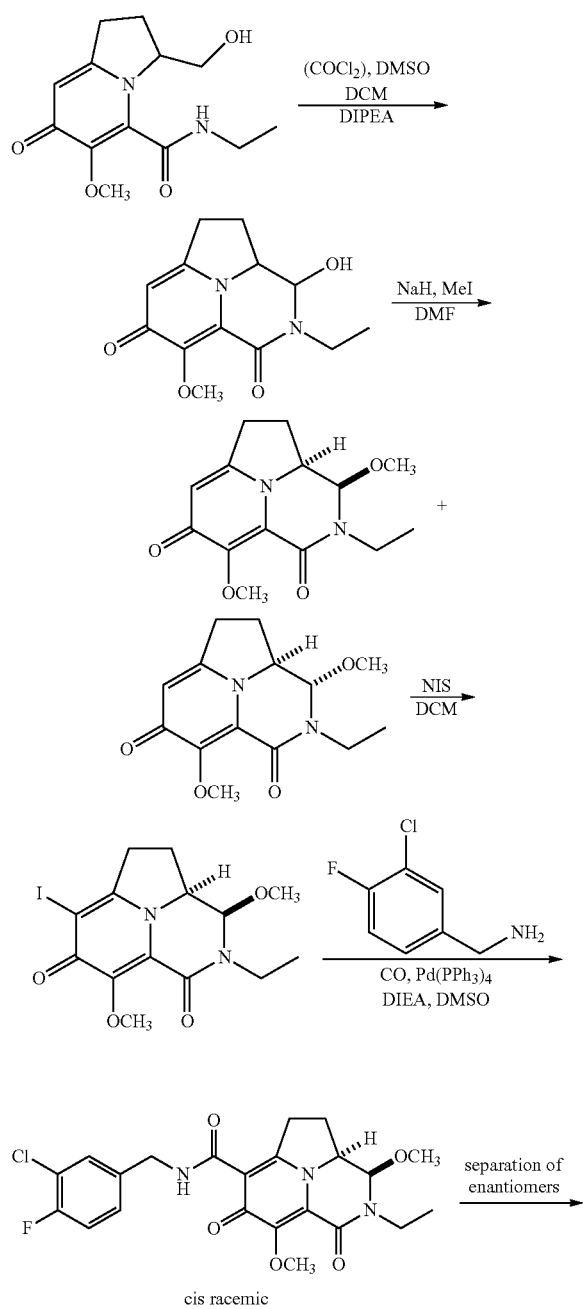

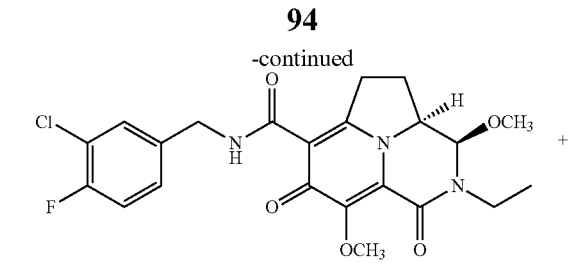

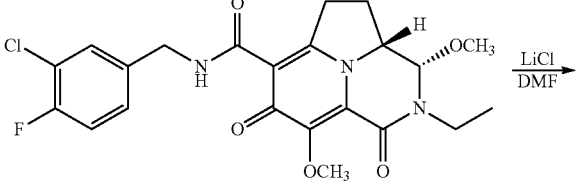

Step 1: 2-Ethyl-3-hydroxy-8-methoxy-3,3a,4,5-tetrahydro-1H-pyrazino[2,1,6-cd]indolizine-1,7(2H)-dione

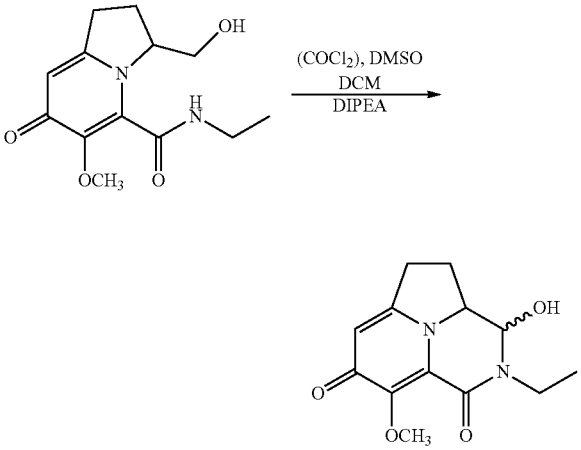

A solution of oxalyl chloride (0.49 mL, 5.63 mmol) in CH₂Cl₂ (6 mL) was cooled to −78° C. and a solution of DMSO (0.53 mL, 7.51 mmol) in CH₂Cl₂ (6 mL) was added dropwise to the stirring mixture. After 20 minutes, a solution of N-ethyl-3-(hydroxymethyl)-6-methoxy-7-oxo-1,2,3,7-tetrahydroindolizine-5-carboxamide (500 mg, 1.88 mmol) in CH₂Cl₂ (6 mL) was added dropwise to the reaction mixture at the same temperature. The mixture was stirred at −78° C. for 1 h. DIEA (1.64 mL, 9.39 mmol) was then added to the mixture and the resulting mixture was allowed to warm to room temperature overnight. The reaction mixture was concentrated in vacuo to provide the title compound, which was carried on to the subsequent step without further purification. Assume quantitative yield. MS (+ESI) m/z: 265.2.

Step 2: (cis)-2-ethyl-3,8-dimethoxy-3,3a,4,5-tetrahydro-1H-pyrazino[2,1,6-cd]indolizine-1,7(2H)-dione (trans)-2-ethyl-3,8-dimethoxy-3,3a,4,5-tetrahydro-1H-pyrazino[2,1,6-cd]indolizine-1,7(2H)-dione

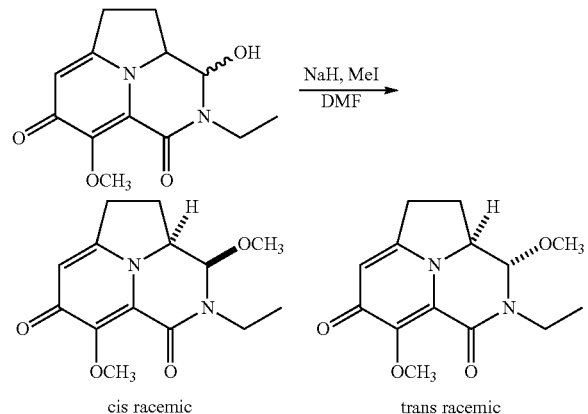

To the unpurified mixture of 2-ethyl-3-hydroxy-8-methoxy-3,3a,4,5-tetrahydro-1H-pyrazino[2,1,6-cd]indolizine-1,7(2H)-dione (496 mg, 1.88 mmol) in DMF (19 mL) was added 60% NaH (375 mg, 9.4 mmol) followed by CH₃I (0.35 mL, 5.6 mmol) and the mixture stirred at room temperature. After 10 minutes, an additional 5 equivalents of 60% NaH (375 mg, 9.4 mmol) and an additional 4 equiv. of CH₃I (0.47 mL, 7.5 mmol) were added and the mixture stirred for 10 min at room temperature. The mixture was cooled to 0° C. and quenched by dropwise addition of MeOH (5 mL). The reaction mixture was then concentrated to dryness by azeotroping with toluene. The resulting residue was purified by gradient elution on reverse phase (50×250 mm (10 um) Phenomenex Prep C18; 0 to 50% CH₃CN/water w/ 0.1% TFA modifier over 30 min at 90 mL/min) to separate diastereomers and afford (cis)-2-ethyl-3,8-dimethoxy-3,3a,4,5-tetrahydro-1H-pyrazino[2,1,6-cd]indolizine-1,7(2H)-dione (224 mg, 42%) (first eluting diastereomer) as a tan gum and (trans)-2-ethyl-3,8-dimethoxy-3,3a,4,5-tetrahydro-1H-pyrazino[2,1,6-cd]indolizine-1,7(2H)-dione (59 mg, 11%) as a tan gum. MS (+ESI) m/z: 279.3.

Step 3: (cis)-2-ethyl-6-iodo-3,8-dimethoxy-3,3a,4,5-tetrahydro-1H-pyrazino[2,1,6-cd]indolizine-1,7(2H)-dione

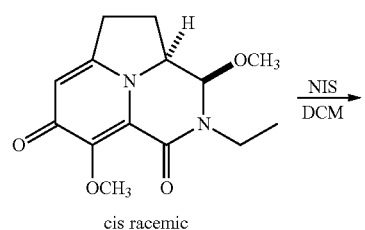

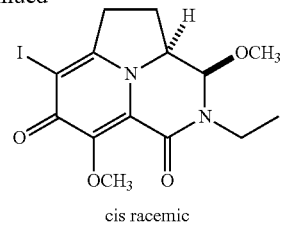

To a solution of (Cis)-2-ethyl-3,8-dimethoxy-3,3a,4,5-tetrahydro-1H-pyrazino[2,1,6-cd]indolizine-1,7(2H)-dione (280 mg, 1.0 mmol) in CH₂Cl₂ (10 mL) was added NIS (453 mg, 2.0 mmol). The mixture was stirred at the room temperature for 15 min. The reaction mixture was filtered washing with minimal CH₂Cl₂ and concentrated to dryness to afford the title compound as a dark brown solid, which was carried on to the subsequent step without further purification. Assume quantitative yield. MS (+ESI) m/z: 405.2.

Step 4: (3R,3aS)-N-(3-chloro-4-fluorobenzyl)-2-ethyl-3,8-dimethoxy-1,7-dioxo-2,3,3a,4,5,7-hexahydro-1H-pyrazino[2,1,6-cd]indolizine-6-carboxamide

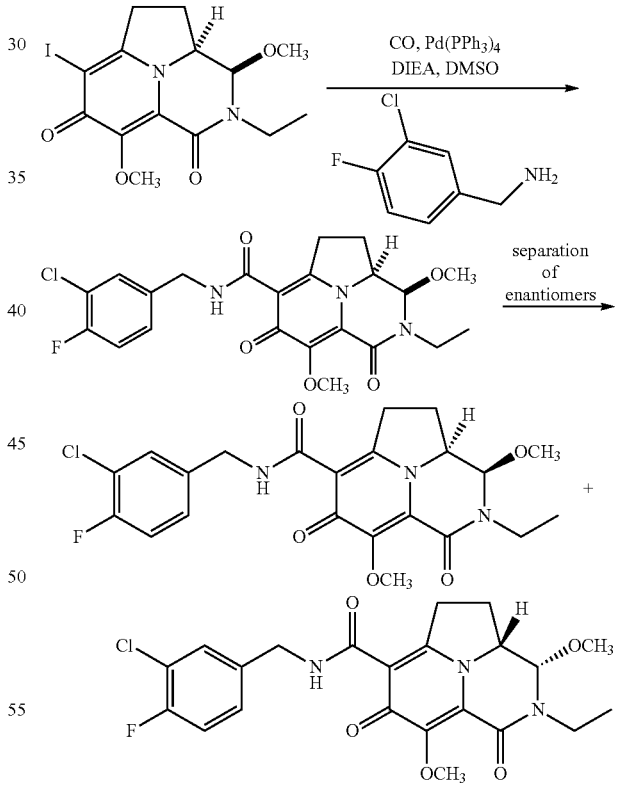

To a solution of unpurified racemic (cis)-2-ethyl-6-iodo-3,8-dimethoxy-3,3a,4,5-tetrahydro-1H-pyrazino[2,1,6-cd]indolizine-1,7(2H)-dione (407 mg, 1.0 mmol) in DMSO (20 mL) was added DIEA (0.86 mL, 5.0 mmol), (3-chloro-4-fluorophenyl)methanamine (632 mg, 4.0 mmol), and Pd(PPh₃)₄ (172 mg, 0.15 mmol). The reaction vessel was evacuated and backfilled 3× with CO₍g₎. The mixture was stirred at 100° C. under an atmosphere of CO₍g₎ (balloon) for 2 h. The mixture was partitioned between water (30 mL) and EtOAc (200 mL). The organic phase was washed with water (4×30 mL) and brine (50 mL), dried over MgSO4, filtered, and concentrated in vacuo. The resulting residue was purified by gradient elution on reverse phase (50×250 mm (10 um) Phenomenex Prep C18; 20 to 70% CH3CN/water w/ 0.1% TFA modifier over 30 min at 90 mL/min) and repurified by gradient elution on silica gel (RediSep-Gold-12 g, 20 to 100% EtOAc in hexanes and the 100% [10% MeOH in EtOAc], 35 minute gradient) to separate the product from triphenylphosphine oxide and provide the title compound (190 mg, 41%) as yellow foam. MS (+ESI) m/z: 464.3. 1H NMR (500 MHz, CDCl3): δ 10.99 (s, 1H); 7.39 (d, J=7.0 Hz, 1H); 7.21 (s, 1H); 7.07 (t, J=8.7 Hz, 1H); 4.73 (s, 1H); 4.60 (dd, J=15.2, 6.2 Hz, 1H); 4.45-4.49 (m, 2H); 4.27 (dq, J=13.7, 7.2 Hz, 1H); 4.12 (dd, J=18.9, 8.7 Hz, 1H); 4.05 (s, 3H); 3.42 (s, 3H); 3.23 (dq, J=13.7, 7.2 Hz, 1H); 2.30-2.37 (m, 2H); 1.31 (t, J=7.1 Hz, 3H).

Enantiomers were separated by chiral preparative SFC (2-cm×25-cm OJ-H column; isocratic [15% (0.1% DEA/ CH3OH)]/[85% CO2]; 50 mL/min flowrate; 254 nm; dissolved in MeOH; 1 mL/injection) to provide (3R,3aS)-N-(3-chloro-4-fluorobenzyl)-2-ethyl-3,8-dimethoxy-1,7-dioxo-2,3,3a,4,5,7-hexahydro-1H-pyrazino[2,1,6-cd]indolizine-6-carboxamide and (3R,3aR)-N-(3-chloro-4-fluorobenzyl)-2-ethyl-3,8-dimethoxy-1,7-dioxo-2,3,3a,4,5,7-hexahydro-1H-pyrazino[2,1,6-cd]indolizine-6-carboxamide as off-white solids. The first eluting enantiomer was determined to be the compound of interest.

Step 6: (3R,3aS)-N-(3-chloro-4-fluorobenzyl)-2-ethyl-8-hydroxy-3-methoxy-1,7-dioxo-2,3,3a,4,5,7-hexahydro-1H-pyrazino[2,1,6-cd]indolizine-6-carboxamide

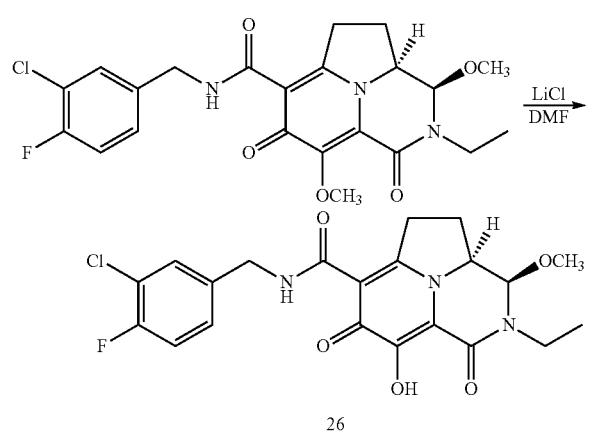

To a solution of (3R,3aS)-N-(3-chloro-4-fluorobenzyl)-2-ethyl-3,8-dimethoxy-1,7-dioxo-2,3,3a,4,5,7-hexahydro-1H-pyrazino[2,1,6-cd]indolizine-6-carboxamide (156 mg, 0.34 mmol) in DMF (6.7 mL) was added anhydrous LiCl (428 mg, 10.1 mmol). The resulting solution was heated at 100° C. for 2 h under N2 with stirring. The reaction mixture was purified directly by gradient elution on reverse phase (30× 150 mm (5 μm) SunFire Prep C18; 20 to 70% CH3CN/water w/ 0.1% TFA modifier over 20 min at 40 mL/min) to provide compound 26 (115 mg, 76%) as a peach foam. MS (+ESI) m/z: 450.3. 1H NMR (500 MHz, CDCl3): δ 10.92 (s, 1H); 7.38 (d, J=6.9 Hz, 1H); 7.21 (s, 1H); 7.07 (t, J=8.7 Hz, 1H); 5.30 (s, 1H); 4.83 (s, 1H); 4.58 (dd, J=15.5, 5.7 Hz, 1H); 4.52 (t, J=9.7 Hz, 1H); 4.26 (dd, J=13.9, 7.2 Hz, 1H); 4.11 (dd, J=18.9, 9.0 Hz, 1H); 3.48 (s, 3H); 3.35-3.43 (m, 1H); 3.27-3.31 (m, 1H); 2.01 (s, 2H); 1.33 (t, J=7.1 Hz, 3H).

Example 12

Preparation of Compound 30

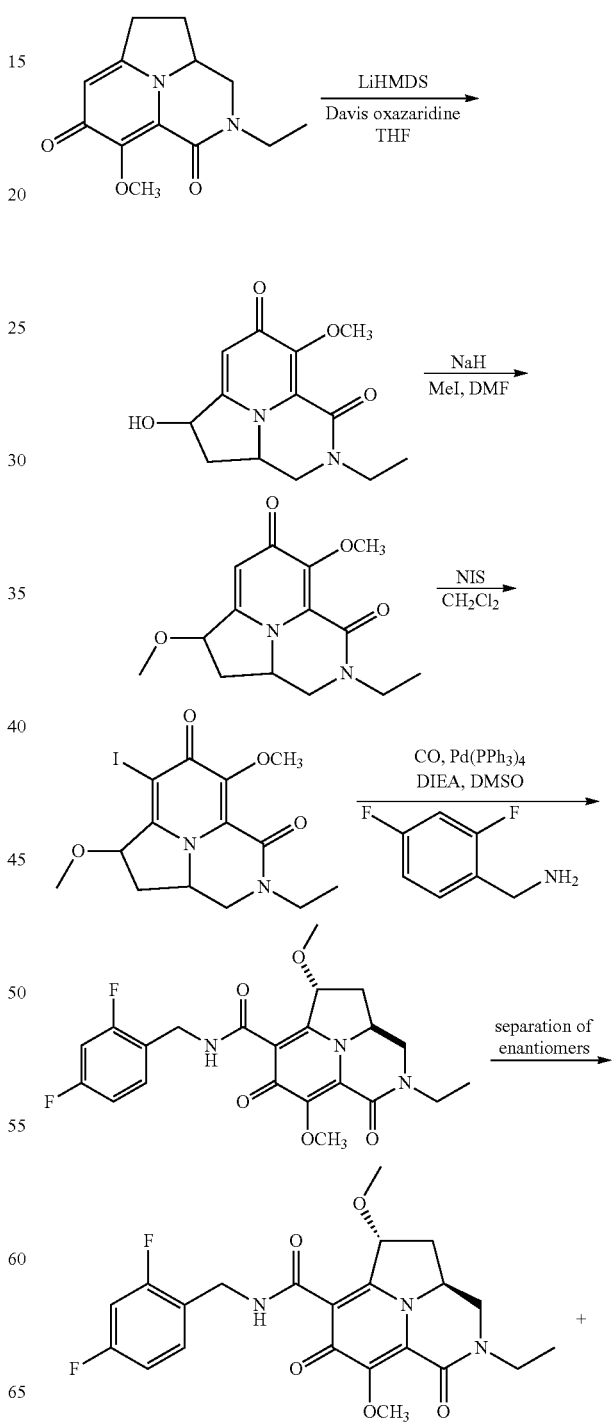

-continued

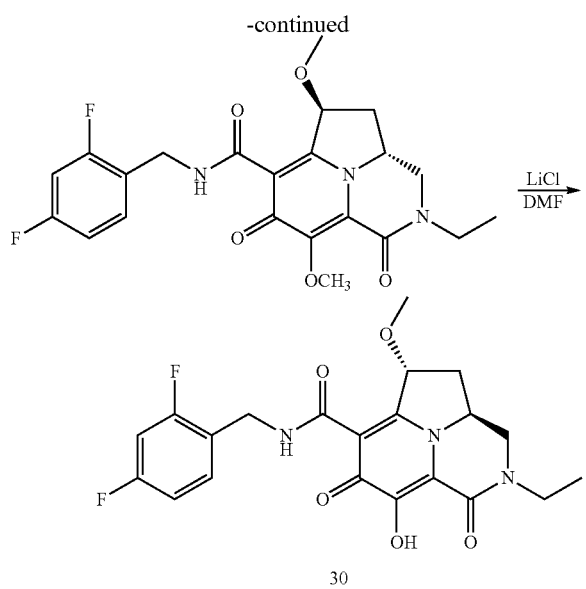

Step 1: 2-ethyl-5-hydroxy-8-methoxy-3,3a,4,5-tetrahydro-1H-pyrazino[2,1,6-cd]indolizine-1,7(2H)-dione

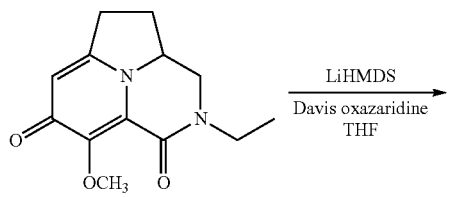

A solution 2-ethyl-8-methoxy-3,3a,4,5-tetrahydro-1H-pyrazino[2,1,6-cd]indolizine-1,7(2H)-dione (1.2 g, 4.83 mmol) in THF (40 mL) was cooled to −78° C. and treated dropwise with LiHMDS (1M in tetrahydrofuran, 9.67 ml, 9.67 mmol) and stirred at −78° C. for 1 h (light orange solution turns deep purple). The mixture was treated with a solution of 3-phenyl-2-(phenylsulfonyl)-1,2-oxaziridine (Davis oxaziridine) (1.516 g, 5.80 mmol) in THF (8 mL) and then removed from the dry ice bath and stirred for 10 min as it warmed to room temperature. The reaction mixture was concentrated and the residue was dissolved in MeOH and purified directly by gradient elution on reverse phase (50× 250 mm (5 μm) Sunfire Prep C18; 0 to 50% CH$_3$CN/water w/ 0.1% TFA modifier over 30 min at 90 mL/min, 2 injections) to yield the title compound (467 mg, 37%) as a tan film. LRMS (+ESI) m/z=265.2.

Step 2: 2-ethyl-5,8-dimethoxy-3,3a,4,5-tetrahydro-1H-pyrazino[2,1,6-cd]indolizine-1,7(2H)-dione

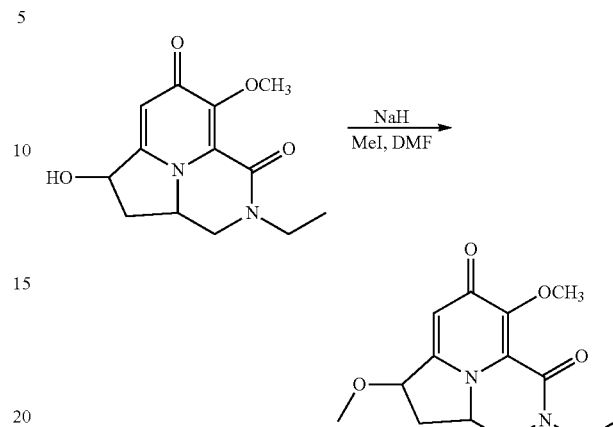

A solution of 2-ethyl-5-hydroxy-8-methoxy-3,3a,4,5-tetrahydro-1H-pyrazino[2,1,6-cd]indolizine-1,7(2H)-dione (467 mg, 1.767 mmol) in DMF (8.8 mL) was treated with NaH (212 mg, 5.30 mmol) and CH$_3$I (221 μl, 3.53 mmol) at room temperature and stirred for 10 min. The mixture was then quenched with a 5 drops of water and concentrated to dryness, azeotroping with toluene (3×). The residue was dissolved in water/CH$_3$OH, filtered through a syringe filter, and purified directly by gradient elution on reverse phase (50×250 mm (5 μm) Sunfire Prep C18; 5 to 95% CH$_3$CN/water w/ 0.1% TFA modifier over 30 min at 90 mL/min, 1 injection). Pure fractions were concentrated in vacuo to yield the title compound (247 mg, 50%) as a tan film. LRMS (+ESI) m/z=279.2.

Step 3: 2-ethyl-6-iodo-5,8-dimethoxy-3,3a,4,5-tetrahydro-1H-pyrazino[2,1,6-cd]indolizine-1,7(2H)-dione

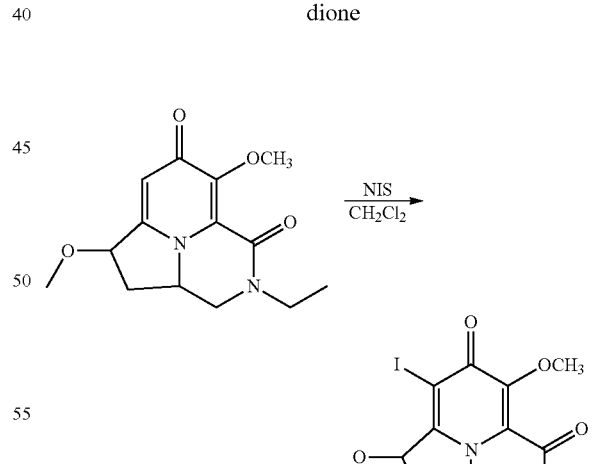

A solution of 2-ethyl-5,8-dimethoxy-3,3a,4,5-tetrahydro-1H-pyrazino[2,1,6-cd]indolizine-1,7(2H)-dione (247 mg, 0.888 mmol) in CH$_2$Cl$_2$ (22.8 mL) was treated with N-iodosuccinimide (399 mg, 1.775 mmol) and stirred at room temperature for 20 min. The mixture was treated with additional N-iodosuccinimide (399 mg, 1.775 mmol) four times over 1 h. The reaction mixture was filtered through a fine fritted scintered glass funnel and the filtrate was concentrated. The isolated material was used in the subsequent step without further purification assuming quantitative conversion. The overall yield was not determined. LRMS (+ESI) m/z=405.2.

Step 4: (3aS,5R)-N-(2,4-difluorobenzyl)-2-ethyl-5,8-dimethoxy-1,7-dioxo-2,3,3a,4,5,7-hexahydro-1H-pyrazino[2,1,6-cd]indolizine-6-carboxamide

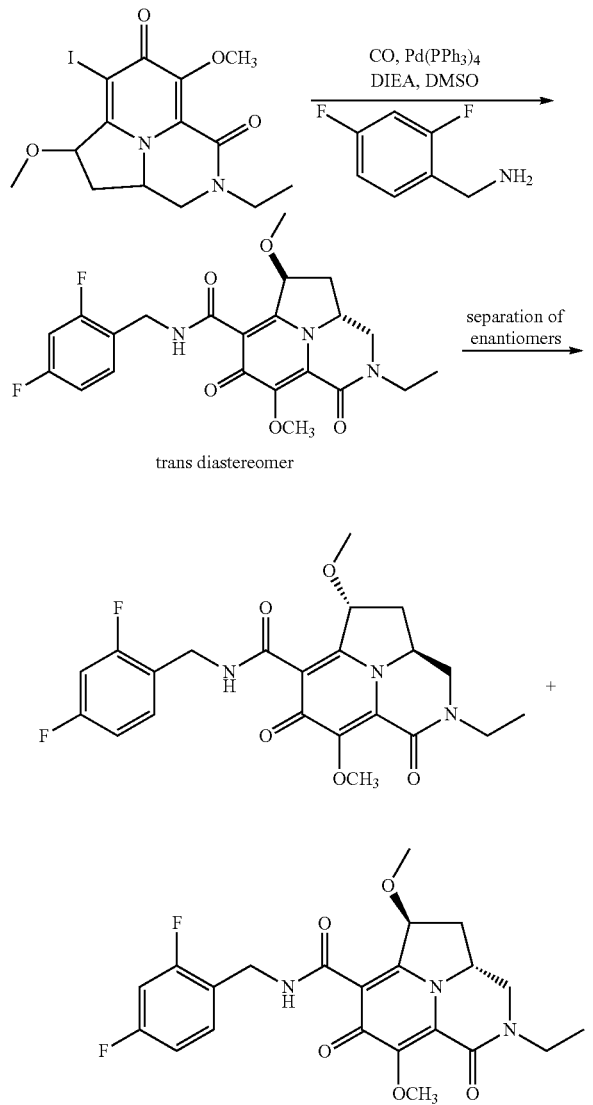

trans diastereomer

A suspension of 2-ethyl-6-iodo-5,8-dimethoxy-3,3a,4,5-tetrahydro-1H-pyrazino[2,1,6-cd]indolizine-1,7(2H)-dione (359 mg, 0.888 mmol), Pd(PPh$_3$)$_4$ (103 mg, 0.089 mmol), 2,4-difluorophenyl)methanamine (509 mg, 3.55 mmol), and DIEA (776 µl, 4.44 mmol) in DMSO (8.8 mL) was degassed with a stream of N$_2$ $_{(g)}$. Next, the flask was evacuated and back-filled with CO$_{(g)}$ and stirred under a CO$_{(g)}$ atmosphere (1 atm) at 100° C. for 25 min. The mixture was partitioned between water (50 mL) and EtOAc (50 mL). The organic phase was washed with water (50 mL) and brine (50 mL), dried over Na$_2$SO$_4$, filtered and concentrated in vacuo. The resulting residue was first purified by gradient elution on silica gel (RediSep-Rf-40 g, 0 to 100% 10% CH$_3$OH in CH$_2$Cl$_2$/CH$_2$Cl$_2$, 20 minute gradient) to afford ~300 mg of impure material. This impure material was purified again by gradient elution on silica gel (RediSep-Rf-24 g, 0 to 100% 10% CH$_3$OH in EtOAc/hexanes, 20 minute gradient) to afford the pure trans diastereomer of the title compound (84 mg, 21%) as a tan foam. LRMS (+ESI) m/z=448.3. The cis diastereomer is also isolated cleanly in this purification.

Enantiomers were separated by chiral preparative SFC (2-cm×25-cm AD-H column; isocratic [40% (0.1% DEA/CH$_3$OH)]/[60% CO$_2$]; 70 mL/min flowrate; 254 nm) to provide enantiopure title compounds as tan foams. The first eluting enantiomer was determined to be the enantiomer of interest.

Step 5: (3aS,5R)-N-(2,4-difluorobenzyl)-2-ethyl-8-hydroxy-5-methoxy-1,7-dioxo-2,3,3a,4,5,7-hexahydro-1H-pyrazino[2,1,6-cd]indolizine-6-carboxamide

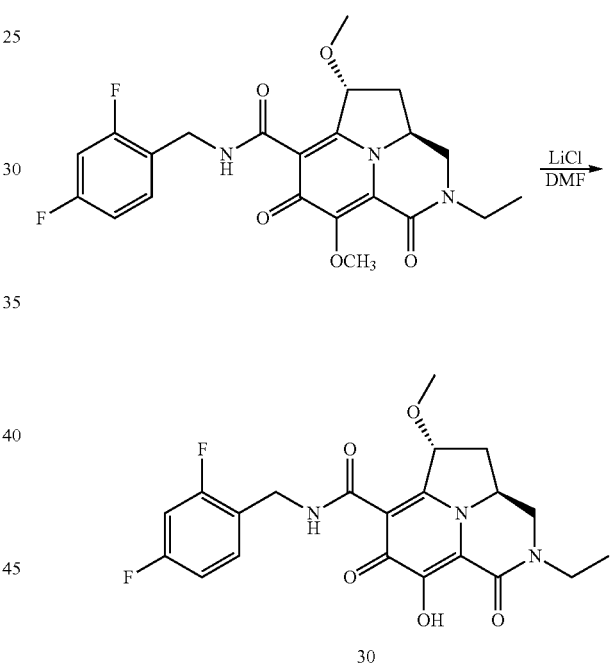

30

A solution of (3aS,5R)-N-(2,4-difluorobenzyl)-2-ethyl-5,8-dimethoxy-1,7-dioxo-2,3,3a,4,5,7-hexahydro-1H-pyrazino[2,1,6-cd]indolizine-6-carboxamide (61 mg, 0.136 mmol) in DMF (1363 µl) was treated with LiCl (173 mg, 4.09 mmol) and stirred at 100° C. for 30 min. The mixture was diluted with MeOH, filtered and purified directly by gradient elution on reverse phase (30×150 mm (5 µm) Sunfire Prep C18; 5 to 95% CH$_3$CN/water w/ 0.1% TFA modifier over 20 min @ 40 mL/min, 1 injection), to yield Compound 30 (45 mg, 76%) as a pale orange foam. LRMS (+ESI) m/z=434.3. $^1$H NMR (500 MHz, CDCl$_3$): δ 10.83 (s; 1H); 7.38 (d; J=8.14 Hz; 1H); 6.80-6.83 (m; 2H); 5.97 (d; J=4.56 Hz; 1H); 4.69 (d; J=13.11 Hz; 2H); 4.61 (d; J=15.61 Hz; 1H); 3.66-3.69 (m; 4H); 3.47 (s; 3H); 2.54 (dd; J=12.87; 4.92 Hz; 1H); 1.98 (m; 1H); 1.27 (t; J=6.99 Hz; 3H).

Example 13

Preparation of Compound 35

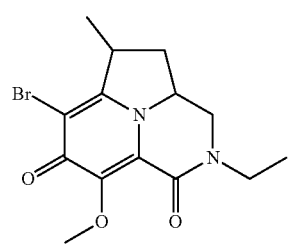

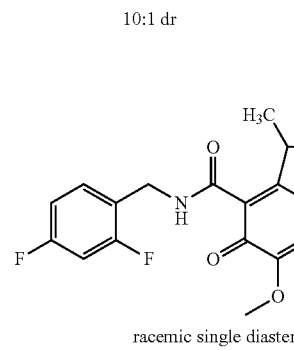

10:1 dr

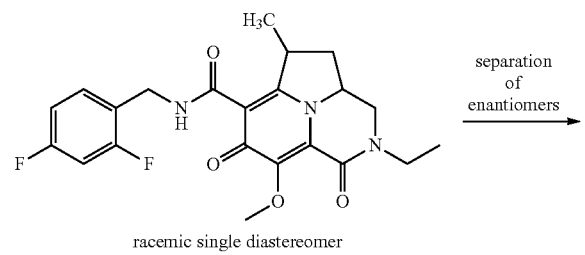

racemic single diastereomer

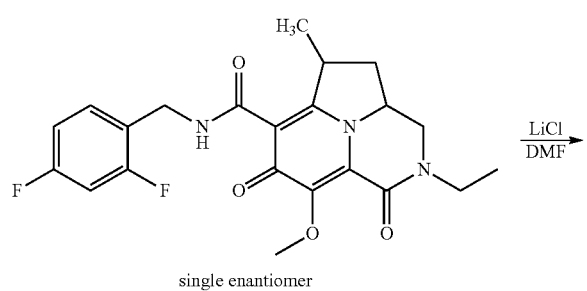

single enantiomer

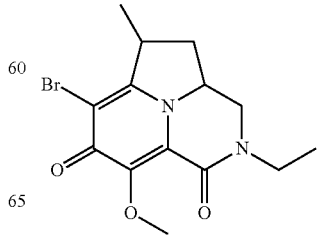

35

Step 1: 6-bromo-2-ethyl-8-methoxy-5-methyl-3,3a, 4,5-tetrahydro-1H-pyrazino[2,1,6-cd]indolizine-1,7 (2H)-dione

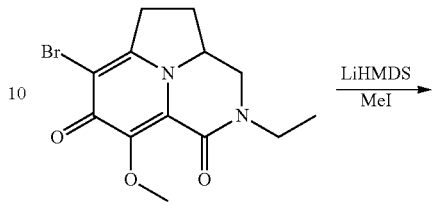

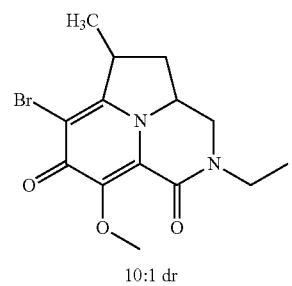

10:1 dr

A stirred solution of 6-bromo-2-ethyl-8-methoxy-3,3a,4, 5-tetrahydro-1H-pyrazino[2,1,6-cd]indolizine-1,7(2H)-dione (Example 9, 50 mg, 0.153 mmol) in dry THF (30 mL) was cooled to −78° C. under $N_2$. To the resulting solution was added a solution of LiHMDS (0.48 mL, 1N in THF, 0.48 mmol). After 1 h, the $CH_3I$ (80 mg, 0.5 mmol) in THF (10 mL) was added at −78° C., and the mixture was stirred for 1 h at room temperature. The reaction was quenched with saturated $NH_4Cl$ (10 mL), and the mixture was extracted with EtOAc (20 mL×3). The combined extracts were washed with water and brine, and evaporated. The resulting residue was purified by preparative thin layer chromatography ($CH_2Cl_2/CH_3OH$=10:1) to afford the title compound (30 mg, 57%) as a yellow solid in a 10:1 mixture of diastereomers. LRMS (+ESI) m/z=342. $^1$H NMR (400 MHz, $CDCl_3$): δ 6.64 (s, 1H), 4.63-4.66 (m, 1H), 4.04-4.05 (m, 1H), 3.53-3.62 (m, 6H), 2.12-2.16 (m, 2H), 1.38-1.40 (m, 3H), 1.12-1.24 (m, 3H).

Step 2: N-(2,4-difluorobenzyl)-2-ethyl-9-methoxy-6-methyl-1,8-dioxo-2,3,3a,5,6,8-hexahydro-1H-pyrazino[2,1,6-cd]indolizine-7-carboxamide

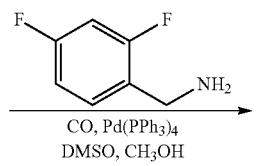

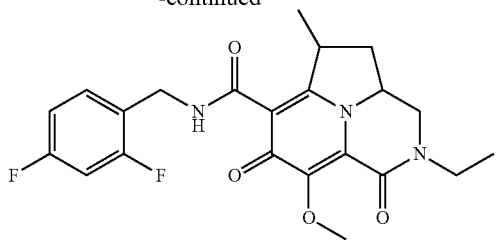

To a solution of 6-bromo-2-ethyl-8-methoxy-5-methyl-3,3a,4,5-tetrahydro-1H-pyrazino[2,1,6-cd]indolizine-1,7(2H)-dione (30 mg, 0.085 mmol) in 1:3 DMSO/CH$_3$OH (5 mL) was added DIEA (170 mg, 0.8 mmol), (4-fluoro-2-methoxyphenyl)methanamine (80 mg, 0.6 mmol), and Pd(PPh$_3$)$_4$ (10 mg, 0.016 mmol). The mixture was stirred at 80° C. overnight under CO$_{(g)}$ balloon. The reaction mixture was purified directly by preparative thin layer chromatography (CH$_2$Cl$_2$/CH$_3$OH=10:1) to afford the title compound (5 mg, 14.2%) as a white solid as a mixture diastereomers.

Enantiomers were separated by chiral preparative SFC (4.6 mm×150 mm Chiralpak AS-H column; gradient [5 to 40% (0.05% DEA/CH$_3$OH)]/[CO$_2$]; 3 mL/min flowrate; 220 nm) to provide each enantiomer of the major diastereomer. The first eluting enantiomer was determined to be the enantiomer of interest. LRMS (+ESI) m/z=432. $^1$H NMR (400 MHz, CDCl$_3$): δ 11.02 (s, 1H), 7.29-7.32 (m, 1H), 6.69-6.76 (m, 2H), 4.54-4.56 (m, 3H), 3.96 (s, 3H), 3.59-3.77 (m, 4H), 2.01-2.11 (m, 3H), 1.34 (d, J=6.8 Hz, 3H), 1.15 (t, J=7.2 Hz, 3H).

Step 3: N-(2,4-difluorobenzyl)-2-ethyl-9-hydroxy-6-methyl-1,8-dioxo-2,3,3a,5,6,8-hexahydro-1H-pyrazino[2,1,6-cd]indolizine-7-carboxamide

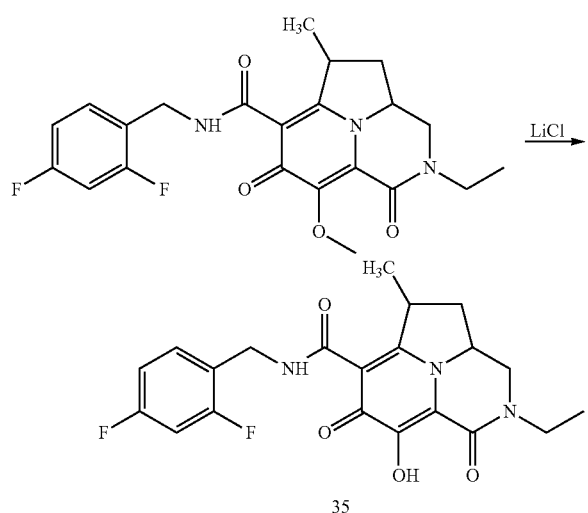

To a solution of compound N-(2,4-difluorobenzyl)-2-ethyl-9-methoxy-6-methyl-1,8-dioxo-2,3,3a,5,6,8-hexahydro-1H-pyrazino[2,1,6-cd]indolizine-7-carboxamide (15 mg, 0.033 mmol) in DMF (3 mL) was added anh. LiCl (20 mg, 0.5 mmol). The resulting solution was heated to 110° C. for 2 h under N$_2$ with stirring. The product was purified by prep-HPLC (Agela DuraShell C18 150*25*5 μm using water and acetonitrile as the eluents. Mobile phase A: water (containing 0.05% TFA), mobile phase B: acetonitrile. Gradient: 30% to 60% B, 0-8.0 min. Flow Rate: 35 mL/min) to afford the title compound (9.04 mg, 64.6%) as a white solid. LRMS (+ESI) m/z=418. $^1$H NMR (400 MHz, CDCl$_3$): δ 10.29 (s, 1H), 7.26-7.32 (m, 1H), 6.70-7.78 (m, 2H), 4.53-4.58 (m, 3H), 3.51-3.63 (m, 4H), 2.09-2.13 (m, 3H), 1.33-1.35 (m, 3H), 1.17-1.30 (m, 3H).

Example 14

Preparation of Compound 34

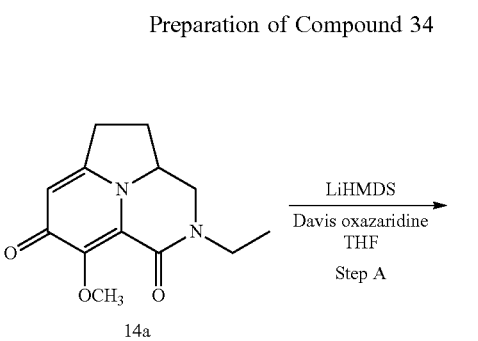

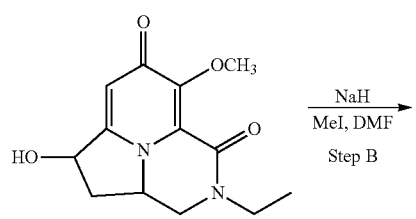

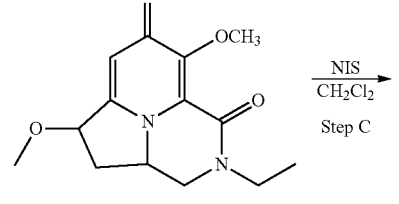

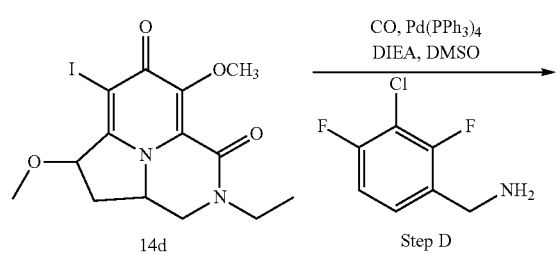

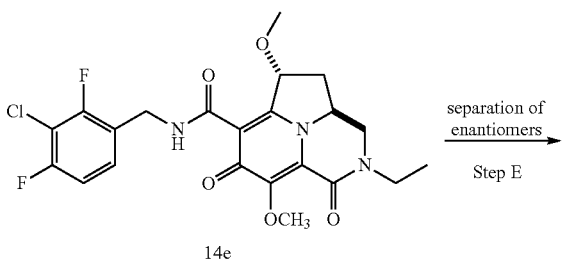

-continued

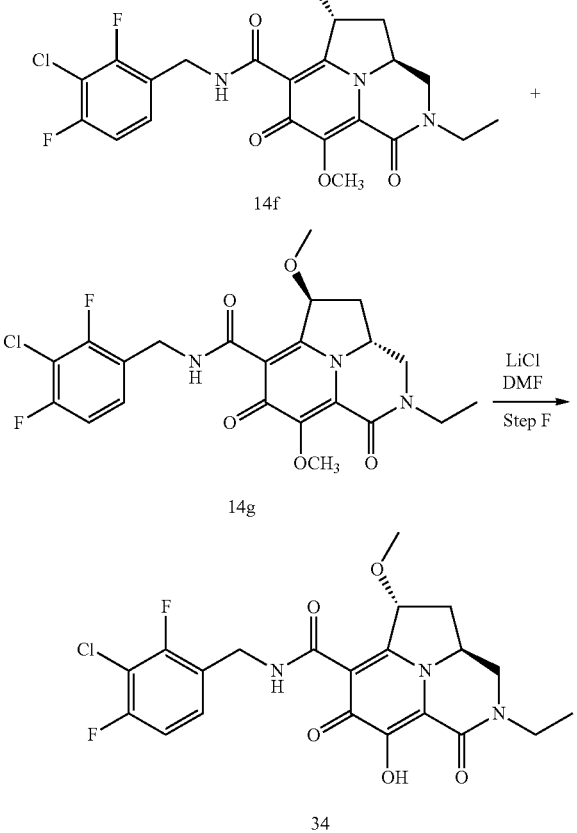

14f

+

14g → LiCl DMF Step F

34

Step A: Synthesis of Intermediate Compound 14b
Step A was performed using the method described above in Example 12, Step 1 and using the indicated starting material and reagents to provide compound 14b. LRMS ESI [M+1]$^+$=265.2

Step B: Synthesis of Intermediate Compound 14c
Step B was performed using the method described above in Example 12, Step 2 and using the indicated starting material and reagents to provide compound 14c. LRMS ESI [M+1]$^+$=279.2

Step C: Synthesis of Intermediate Compound 14d
Step C was performed using the method described above in Example 12, Step 3 and using the indicated starting material and reagents to provide compound 14d. LRMS ESI [M+1]$^+$=405.2

Step D: Synthesis of Intermediate Compound 14e
Step D was performed using the method described above in Example 12, Step 4 and using the indicated starting material and reagents to provide compound 14e. LRMS ESI [M+1]$^+$=482.2

Step E: Synthesis of Intermediate Compounds 14f and 14g
Step E (separation of the enantiomers of compound 14e) was performed using the chiral separation method described above in Example 12, Step 4 to provide compounds 14f and 14g. LRMS ESI [M+1]$^+$=482.2 (for both 14f and 14g).

Step F: Synthesis of Compound 34
Step F was performed using the method described above in Example 12, Step 5 and using the indicated starting material and reagents to provide compound 34. LRMS ESI [M+1]$^+$=468.2. $^1$H NMR (ppm)(CDCl$_3$): δ 10.78 (1H, s), 7.32 (1H, q, J=7.37 Hz), 6.93 (1H, t, J=8.44 Hz), 5.85 (1H, d, J=5.00 Hz), 4.59-4.70 (3H, m), 3.77 (1H, t, J=12.24 Hz), 3.54-3.70 (3H, m), 3.45 (3H, s), 2.49 (1H, dd, J=13.03, 5.15 Hz), 1.97-2.02 (1H, m), 1.26 (3H, t, J=7.15 Hz).

The following comprehensive list of illustrative compounds of the present invention, listed in Table A below, were made using the methods described in the Examples above.

TABLE A

| Compound No. | Structure | Preparative Method Used | LRMS (ESI) [M + 1]$^+$ |
|---|---|---|---|
| 1 | (racemic) | Example 4 | 406 |
| 2 | (racemic) | Example 4 | 434 |

TABLE A-continued

| Compound No. | Structure | Preparative Method Used | LRMS (ESI) [M + 1]+ |
|---|---|---|---|
| 3 | (structure shown) single enantiomer | Example 4 | 434 |
| 4 | (structure shown) racemic | Example 4 | 448 |
| 5 | (structure shown) racemic | Example 4 | 450 |
| 6 | (structure shown) mixture of stereoisomers | Example 4 | 478 |
| 7 | (structure shown) racemic | Example 4 | 483 |

TABLE A-continued

| Compound No. | Structure | Preparative Method Used | LRMS (ESI) [M + 1]+ |
|---|---|---|---|
| 8 | (2,4-difluorobenzyl carboxamide; N-(4-methoxybenzyl) substituted tricyclic core), racemic | Example 4 | 512 |
| 9 | (2,3,4-trifluorobenzyl carboxamide; N-isopropyl substituted tricyclic core), single enantiomer | Example 4 | 452 |
| 10 | (3-chloro-4-fluorobenzyl carboxamide; N-isopropyl substituted tricyclic core), racemic | Example 4 | 450 |
| 11 | (2-fluoro-3-methyl-4-fluorobenzyl carboxamide; N-isopropyl substituted tricyclic core), racemic | Example 4 | 448 |
| 12 | (3-chloro-2,4-difluorobenzyl carboxamide; N-isopropyl substituted tricyclic core), racemic | Example 4 | 468 |

TABLE A-continued

| Compound No. | Structure | Preparative Method Used | LRMS (ESI) [M + 1]+ |
|---|---|---|---|
| 13 | (single enantiomer) | Example 5 | 475 |
| 14 | (racemic) | Example 6 | 457 |
| 15 | (single enantiomer) | Example 6 | 457 |
| 16 | (racemic) | Example 7 | 461 |
| 17 | (racemic) | Example 8 | 372 |

TABLE A-continued

| Compound No. | Structure | Preparative Method Used | LRMS (ESI) [M + 1]+ |
|---|---|---|---|
| 18 | racemic | Example 9 | 404 |
| 19 | racemic | Example 9 | 464 |
| 20 | single enantiomer | Example 9 | 472 |
| 21 | single enantiomer | Example 9 | 448 |
| 22 | single enantiomer | Example 9 | 448 |
| 23 | single enantiomer | Example 9 | 466 |

TABLE A-continued

| Compound No. | Structure | Preparative Method Used | LRMS (ESI) [M + 1]+ |
|---|---|---|---|
| 24 | (structure shown) racemic | Example 10 | 420 |
| 25 | (structure shown) racemic | Example 11 | 434 |
| 26 | (structure shown) single enantiomer | Example 11 | 450 |
| 27 | (structure shown) single enantiomer | Example 11 | 464 |
| 28 | (structure shown) single enantiomer | Example 11 | 448 |
| 29 | (structure shown) racemic | Example 12 | 434 |

TABLE A-continued
| Compound No. | Structure | Preparative Method Used | LRMS (ESI) [M + 1]+ |
|---|---|---|---|
| 30 | 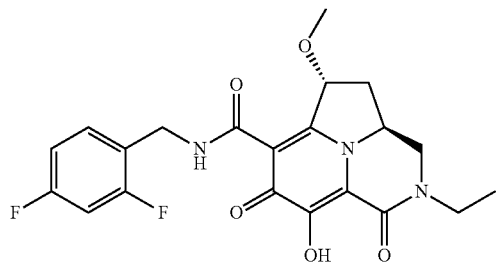 [SMILES: CCN1C[C@@H]2C[C@@H](OC)c3c(C(=O)NCc4ccc(F)cc4F)c(=O)c(O)c(n32)C1=O] single enantiomer | Example 12 | 434 |
| 31 | 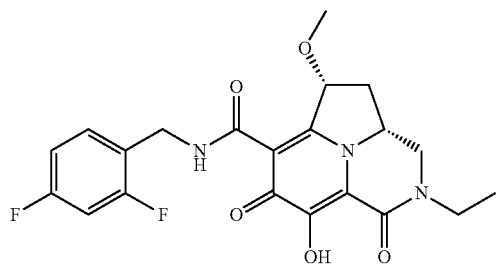 [SMILES: CCN1C[C@H]2C[C@@H](OC)c3c(C(=O)NCc4ccc(F)cc4F)c(=O)c(O)c(n32)C1=O] single enantiomer | Example 12 | 434 |
| 32 | 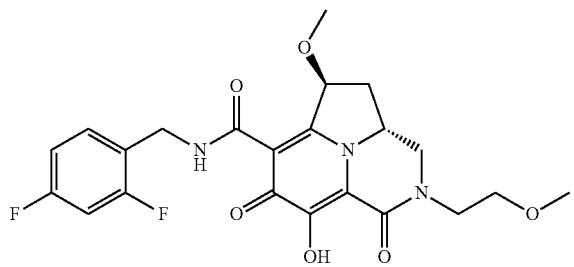 [SMILES: COCCN1C[C@H]2C[C@H](OC)c3c(C(=O)NCc4ccc(F)cc4F)c(=O)c(O)c(n32)C1=O] single enantiomer | Example 12 | 464 |
| 33 | 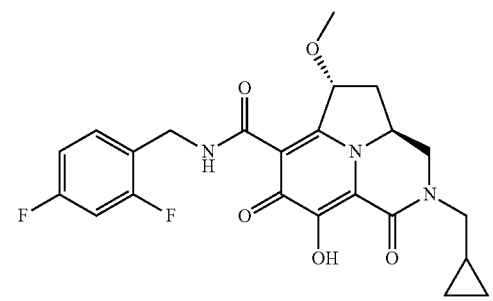 [SMILES: CO[C@@H]1C[C@H]2CN(CC3CC3)C(=O)c3c(O)c(=O)c(C(=O)NCc4ccc(F)cc4F)c1n32] single enantiomer | Example 12 | 460 |

TABLE A-continued
| Compound No. | Structure | Preparative Method Used | LRMS (ESI) [M + 1]+ |
|---|---|---|---|
| 34 | 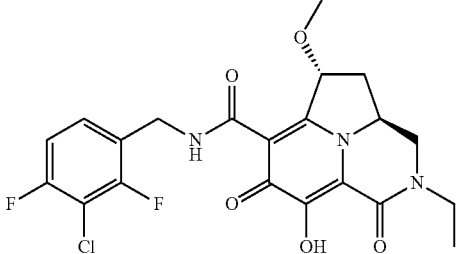 [SMILES: CCN1C[C@@H]2C[C@@H](OC)c3c(C(=O)NCc4ccc(F)c(Cl)c4F)c(=O)c(O)c(n32)C1=O]<br>single enantiomer | Example 12 | 468 |
| 35 | 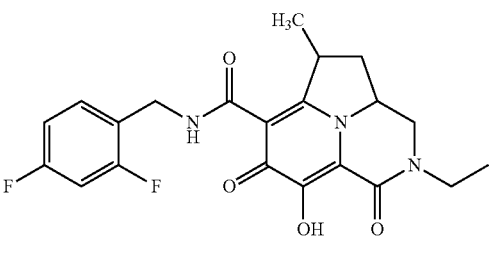 [SMILES: CCN1CC2CC(C)c3c(C(=O)NCc4ccc(F)cc4F)c(=O)c(O)c(n32)C1=O]<br>single enantiomer | Example 13 | 418 |
| 36 | 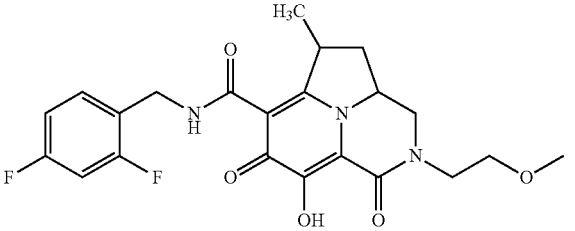 [SMILES: COCCN1CC2CC(C)c3c(C(=O)NCc4ccc(F)cc4F)c(=O)c(O)c(n32)C1=O]<br>single enantiomer | Example 13 | 448 |
| 37 | 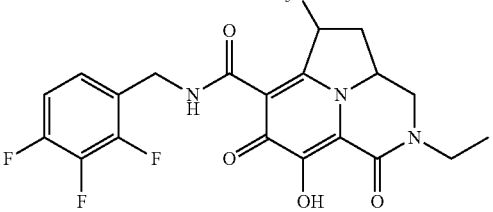<br>single enantiomer | Example 13 | 436 |
| 38 | 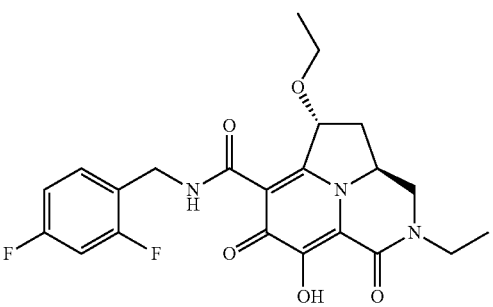 [SMILES: CCO[C@@H]1C[C@H]2CN(CC)C(=O)c3c(O)c(=O)c(C(=O)NCc4ccc(F)cc4F)c1n32]<br>single enantiomer | Example 12 | 448 |

Example 15

Assessing Antiviral Potency in a Multiple Round HIV-1 Infection Assay

HIV-1 replication was monitored using MT4-gag-GFP clone D3 (hereafter designate MT4-GFP), which are MT-4 cells modified to harbor a GFP reporter gene, the expression of which is dependent on the HIV-1 expressed proteins tat and rev. Productive infection of an MT4-GFP cell with HIV-1 results in GFP expression approximately 24 h post-infection.

MT4-GFP cells were maintained at 37° C./5% $CO_2$/90% relative humidity in RPMI 1640 supplemented with 10% fetal bovine serum, 100 U/ml penicillin/streptomycin, and 400 µg/ml G418 to maintain the reporter gene. For infections, MT4-GFP cells were placed in the same medium lacking G418 and infected overnight with HIV-1 (NL4-3 strain) virus at an approximate multiplicity of infection of 0.01 in the same incubation conditions.

Cells were then washed and resuspended in either RPMI 1640 supplemented with 10% normal human serum (NHS) or without NHS at $1.6 \times 10^5$ cells/mL (10% NHS or serum-free conditions) or in 100% normal human serum at $2 \times 10^5$ cells/mL (100% NHS conditions). Compound plates were prepared by dispensing compounds dissolved in DMSO into wells of 384 well poly D lysine-coated plates (0.2 µl/well) using an ECHO acoustic dispenser. Each compound was tested in a 10 point serial 3-fold dilution (typical final concentrations: 8.4 µM-0.42 nM). Controls included no inhibitor (DMSO only) and a combination of three antiviral agents (efavirenz, indinavir, and the integrase strand transfer inhibitor L-002254051 at final concentrations of 4 µM each). Cells were added (50 µL/well) to compound plates and the infected cells were maintained at 37° C./5% $CO_2$/90% relative humidity. Results for selected compounds of the present invention are shown below in Table B.

TABLE B

| Compound No. | Wild Type Cell Assay IP | % NHS |
| --- | --- | --- |
| 1 | 9.2 nM | 0 |
| 2 | 33 nM | 10 |
| 3 | 13 nM | 0 |
| 4 | 21 nM | 10 |
| 5 | 9.2 nM | 0 |
| 6 | 24 nM | 0 |
| 7 | 9.6 nM | 0 |
| 8 | 23 nM | 0 |
| 9 | 20 nM | 10 |
| 10 | 100 nM | 10 |
| 11 | 116 nM | 10 |
| 12 | 50 nM | 10 |
| 13 | 5 nM | 0 |
| 14 | 323 nM | 0 |
| 15 | 234 nM | 0 |
| 16 | 17 nM | 0 |
| 17 | 35 nM | 0 |
| 18 | 2.6 nM | 0 |
| 19 | 4.4 nM | 0 |
| 20 | 3.8 nM | 0 |
| 21 | 3.1 nM | 0 |
| 22 | 2.8 nM | 0 |
| 23 | 3.8 nM | 0 |
| 24 | 2.2 nM | 0 |
| 25 | 1.9 nM | 0 |
| 26 | 3.2 nM | 0 |
| 27 | 2.3 nM | 0 |
| 28 | 2.1 nM | 0 |
| 29 | 1.2 nM | 0 |
| 30 | 1.0 nM | 0 |
| 31 | 3.8 nM | 0 |
| 32 | 2.3 nM | 0 |
| 33 | 2.3 nM | 0 |
| 34 | 2.9 nM | 0 |
| 35 | 1.2 nM | 0 |
| 36 | 3.9 nM | 0 |
| 37 | 1.1 nM | 0 |
| 38 | 1.9 nM | 0 |

Uses of the Fused Tricyclic Heterocycle Derivatives

The Fused Tricyclic Heterocycle Derivatives are useful in human and veterinary medicine for treating or preventing HIV infection in a subject. In one embodiment, the Fused Tricyclic Heterocycle Derivatives can be inhibitors of HIV viral replication. In a specific embodiment, the Fused Tricyclic Heterocycle Derivatives are inhibitors of HIV-1. Accordingly, the Fused Tricyclic Heterocycle Derivatives are useful for treating HIV infections and AIDS. In accordance with the invention, the Fused Tricyclic Heterocycle Derivatives can be administered to a subject in need of treatment or prevention of HIV infection.

Accordingly, in one embodiment, the invention provides methods for treating HIV infection in a subject comprising administering to the subject an effective amount of at least one Fused Tricyclic Heterocycle Derivative or a pharmaceutically acceptable salt thereof. In a specific embodiment, the present invention provides methods for treating AIDS in a subject comprising administering to the subject an effective amount of at least one Fused Tricyclic Heterocycle Derivative or a pharmaceutically acceptable salt thereof.

Treatment or Prevention of HIV Infection

The Fused Tricyclic Heterocycle Derivatives are useful in the inhibition of HIV, the treatment of HIV infection and/or reduction of the likelihood or severity of symptoms of HIV infection and the inhibition of HIV viral replication and/or HIV viral production in a cell-based system. For example, the Fused Tricyclic Heterocycle Derivatives are useful in treating infection by HIV after suspected past exposure to HIV by such means as blood transfusion, exchange of body fluids, bites, accidental needle stick, or exposure to subject blood during surgery or other medical procedures.

In one embodiment, the HIV infection has progressed to AIDS.

Accordingly, in one embodiment, the invention provides methods for treating HIV infection in a subject, the methods comprising administering to the subject an effective amount of at least one Fused Tricyclic Heterocycle Derivative or a pharmaceutically acceptable salt thereof. In a specific embodiment, the amount administered is effective to treat or prevent infection by HIV in the subject. In another specific embodiment, the amount administered is effective to inhibit HIV viral replication and/or viral production in the subject.

The Fused Tricyclic Heterocycle Derivatives are also useful in the preparation and execution of screening assays for antiviral compounds. For example the Fused Tricyclic Heterocycle Derivatives are useful for identifying resistant HIV cell lines harboring mutations, which are excellent screening tools for more powerful antiviral compounds. Furthermore, the Fused Tricyclic Heterocycle Derivatives are useful in establishing or determining the binding site of other antivirals to the HIV Integrase.

The compositions and combinations of the present invention can be useful for treating a subject suffering from infection related to any HIV genotype.

Combination Therapy

In another embodiment, the present methods for treating or preventing HIV infection can further comprise the administration of one or more additional therapeutic agents which are not Fused Tricyclic Heterocycle Derivatives.

In one embodiment, the additional therapeutic agent is an antiviral agent.

In another embodiment, the additional therapeutic agent is an immunomodulatory agent, such as an immunosuppressive agent.

Accordingly, in one embodiment, the present invention provides methods for treating a viral infection in a subject, the method comprising administering to the subject: (i) at least one Fused Tricyclic Heterocycle Derivative (which may include two or more different Fused Tricyclic Heterocycle Derivatives), or a pharmaceutically acceptable salt thereof, and (ii) at least one additional therapeutic agent that is other than a Fused Tricyclic Heterocycle Derivative, wherein the amounts administered are together effective to treat or prevent a viral infection.

When administering a combination therapy of the invention to a subject, therapeutic agents in the combination, or a pharmaceutical composition or compositions comprising therapeutic agents, may be administered in any order such as, for example, sequentially, concurrently, together, simultaneously and the like. The amounts of the various actives in such combination therapy may be different amounts (different dosage amounts) or same amounts (same dosage amounts). Thus, for non-limiting illustration purposes, a Fused Tricyclic Heterocycle Derivative and an additional therapeutic agent may be present in fixed amounts (dosage amounts) in a single dosage unit (e.g., a capsule, a tablet and the like).

In one embodiment, the at least one Fused Tricyclic Heterocycle Derivative is administered during a time when the additional therapeutic agent(s) exert their prophylactic or therapeutic effect, or vice versa.

In another embodiment, the at least one Fused Tricyclic Heterocycle Derivative and the additional therapeutic agent(s) are administered in doses commonly employed when such agents are used as monotherapy for treating a viral infection.

In another embodiment, the at least one Fused Tricyclic Heterocycle Derivative and the additional therapeutic agent(s) are administered in doses lower than the doses commonly employed when such agents are used as monotherapy for treating a viral infection.

In still another embodiment, the at least one Fused Tricyclic Heterocycle Derivative and the additional therapeutic agent(s) act synergistically and are administered in doses lower than the doses commonly employed when such agents are used as monotherapy for treating a viral infection.

In one embodiment, the at least one Fused Tricyclic Heterocycle Derivative and the additional therapeutic agent(s) are present in the same composition. In one embodiment, this composition is suitable for oral administration. In another embodiment, this composition is suitable for intravenous administration. In another embodiment, this composition is suitable for subcutaneous administration. In still another embodiment, this composition is suitable for parenteral administration.

Viral infections and virus-related disorders that can be treated or prevented using the combination therapy methods of the present invention include, but are not limited to, those listed above.

In one embodiment, the viral infection is HIV infection.

In another embodiment, the viral infection is AIDS.

The at least one Fused Tricyclic Heterocycle Derivative and the additional therapeutic agent(s) can act additively or synergistically. A synergistic combination may allow the use of lower dosages of one or more agents and/or less frequent administration of one or more agents of a combination therapy. A lower dosage or less frequent administration of one or more agents may lower toxicity of therapy without reducing the efficacy of therapy.

In one embodiment, the administration of at least one Fused Tricyclic Heterocycle Derivative and the additional therapeutic agent(s) may inhibit the resistance of a viral infection to these agents.

As noted above, the present invention is also directed to use of a compound of Formula I with one or more anti-HIV agents. An "anti-HIV agent" is any agent which is directly or indirectly effective in the inhibition of HIV reverse transcriptase or another enzyme required for HIV replication or infection, the treatment or prophylaxis of HIV infection, and/or the treatment, prophylaxis or delay in the onset or progression of AIDS. It is understood that an anti-HIV agent is effective in treating, preventing, or delaying the onset or progression of HIV infection or AIDS and/or diseases or conditions arising therefrom or associated therewith. For example, the compounds of this invention may be effectively administered, whether at periods of pre-exposure and/or post-exposure, in combination with effective amounts of one or more anti-HIV agents selected from HIV antiviral agents, imunomodulators, antiinfectives, or vaccines useful for treating HIV infection or AIDS. Suitable HIV antivirals for use in combination with the compounds of the present invention include, for example, those listed in Table A as follows:

TABLE A

| Name | Type |
| --- | --- |
| abacavir, ABC, Ziagen ® | nRTI |
| abacavir + lamivudine, Epzicom ® | nRTI |
| abacavir + lamivudine + zidovudine, Trizivir ® | nRTI |
| amprenavir, Agenerase ® | PI |
| atazanavir, Reyataz ® | PI |
| AZT, zidovudine, azidothymidine, Retrovir ® | nRTI |
| CMX-157 | nRTI |
| darunavir, Prezista ® | PI |
| ddC, zalcitabine, dideoxycytidine, Hivid ® | nRTI |
| ddI, didanosine, dideoxyinosine, Videx ® | nRTI |
| ddI (enteric coated), Videx EC ® | nRTI |
| delavirdine, DLV, Rescriptor ® | nnRTI |
| Dolutegravir | PI |
| efavirenz, EFV, Sustiva ®, Stocrin ® | nnRTI |
| efavirenz + emtricitabine + tenofovir DF, Atripla ® | nnRTI + nRTI |
| Elvitegravir | InI |
| emtricitabine, FTC, Emtriva ® | nRTI |
| emtricitabine + tenofovir DF, Truvada ® | nRTI |
| emvirine, Coactinon ® | nnRTI |
| enfuvirtide, Fuzeon ® | FI |
| enteric coated didanosine, Videx EC ® | nRTI |
| etravirine, TMC-125 | nnRTI |
| fosamprenavir calcium, Lexiva ® | PI |
| indinavir, Crixivan ® | PI |

TABLE A-continued

| Name | Type |
| --- | --- |
| lamivudine, 3TC, Epivir ® | nRTI |
| lamivudine + zidovudine, Combivir ® | nRTI |
| lopinavir | PI |
| lopinavir + ritonavir, Kaletra ® | PI |
| maraviroc, Selzentry ® | EI |
| nelfinavir, Viracept ® | PI |
| nevirapine, NVP, Viramune ® | nnRTI |
| raltegravir, MK-0518, Isentress ® | InI |
| rilpivirine, TMC-278 | nnRTI |
| Rilpivirine + emtricitabine + tenofovir, Complera | nnRTI + nRTI |
| ritonavir, Norvir ® | PI |
| saquinavir, Invirase ®, Fortovase ® | PI |
| stavudine, d4T, didehydrodeoxythymidine, Zerit ® | nRTI |
| tenofovir DF (DF = disoproxil fumarate), TDF, Viread ® | nRTI |
| tipranavir, Aptivus ® | PI |

EI = entry inhibitor; FI = fusion inhibitor; InI = integrase inhibitor;
PI = protease inhibitor; nRTI = nucleoside reverse transcriptase inhibitor;
nnRTI = non-nucleoside reverse transcriptase inhibitor. Some of the drugs listed in the table are used in a salt form; e.g., abacavir sulfate, indinavir sulfate, atazanavir sulfate, nelfinavir mesylate.

In one embodiment, the one or more anti-HIV drugs are selected from raltegravir, lamivudine, abacavir, ritonavir, dolutegravir, darunavir, atazanavir, emtricitabine, tenofovir, elvitegravir, rilpivirine and lopinavir.

In another embodiment, the compound of formula (I) is used in combination with a single anti-HIV drug which is raltegravir.

In another embodiment, the compound of formula (I) is used in combination with a single anti-HIV drug which is lamivudine.

In still another embodiment, the compound of formula (I) is used in combination with a single anti-HIV drug which is atazanavir.

In another embodiment, the compound of formula (I) is used in combination with a single anti-HIV drug which is darunavir.

In another embodiment, the compound of formula (I) is used in combination with a single anti-HIV drug which is rilpivirine.

In yet another embodiment, the compound of formula (I) is used in combination with a single anti-HIV drug which is dolutegravir.

In another embodiment, the compound of formula (I) is used in combination with a single anti-HIV drug which is elvitegravir.

In one embodiment, the compound of formula (I) is used in combination with two anti-HIV drugs which are lamivudine and abacavir.

In another embodiment, the compound of formula (I) is used in combination with two anti-HIV drugs which are darunavir and raltegravir.

In another embodiment, the compound of formula (I) is used in combination with two anti-HIV drugs which are emtricitabine and tenofovir.

In still another embodiment, the compound of formula (I) is used in combination with two anti-HIV drugs which are atazanavir and raltegravir.

In another embodiment, the compound of formula (I) is used in combination with two anti-HIV drugs which are ritonavir and lopinavir.

In another embodiment, the compound of formula (I) is used in combination with two anti-HIV drugs which are lamivudine and raltegravir.

In one embodiment, the compound of formula (I) is used in combination with three anti-HIV drug which are abacavir, lamivudine and raltegravir.

In another embodiment, the compound of formula (I) is used in combination with three anti-HIV drug which are lopinavir, ritonavir and raltegravir.

In one embodiment, the present invention provides pharmaceutical compositions comprising (i) a compound of formula (I) or a pharmaceutically acceptable salt thereof; (ii) a pharmaceutically acceptable carrier; and (iii) one or more additional anti-HIV agents selected from lamivudine, abacavir, ritonavir and lopinavir, or a pharmaceutically acceptable salt thereof, wherein the amounts present of components (i) and (iii) are together effective for the treatment or prophylaxis of infection by HIV or for the treatment, prophylaxis, or delay in the onset or progression of AIDS in the subject in need thereof.

In another embodiment, the present invention provides a method for the treatment or prophylaxis of infection by HIV or for the treatment, prophylaxis, or delay in the onset or progression of AIDS in a subject in need thereof, which comprises administering to the subject (i) a compound of formula (I) or a pharmaceutically acceptable salt thereof and (ii) one or more additional anti-HIV agents selected from lamivudine, abacavir, ritonavir and lopinavir, or a pharmaceutically acceptable salt thereof, wherein the amounts administered of components (i) and (ii) are together effective for the treatment or prophylaxis of infection by HIV or for the treatment, prophylaxis, or delay in the onset or progression of AIDS in the subject in need thereof.

It is understood that the scope of combinations of the compounds of this invention with anti-HIV agents is not limited to the HIV antivirals listed in Table A, but includes in principle any combination with any pharmaceutical composition useful for the treatment or prophylaxis of AIDS. The HIV antiviral agents and other agents will typically be employed in these combinations in their conventional dosage ranges and regimens as reported in the art, including, for example, the dosages described in the *Physicians' Desk Reference*, Thomson PDR, Thomson PDR, 57$^{th}$ edition (2003), the 58$^{th}$ edition (2004), the 59$^{th}$ edition (2005), and the like. The dosage ranges for a compound of the invention in these combinations are the same as those set forth above.

The compounds of this invention are also useful in the preparation and execution of screening assays for antiviral compounds. For example, the compounds of this invention are useful for isolating enzyme mutants, which are excellent screening tools for more powerful antiviral compounds. Furthermore, the compounds of this invention are useful in establishing or determining the binding site of other antivirals to HIV integrase, e.g., by competitive inhibition. Thus the compounds of this invention are commercial products to be sold for these purposes.

The doses and dosage regimen of the other agents used in the combination therapies of the present invention for the treatment or prevention of HIV infection can be determined by the attending clinician, taking into consideration the approved doses and dosage regimen in the package insert; the age, sex and general health of the subject; and the type and severity of the viral infection or related disease or disorder. When administered in combination, the Fused Tricyclic Heterocycle Derivative(s) and the other agent(s) can be administered simultaneously (i.e., in the same composition or in separate compositions one right after the other) or sequentially. This particularly useful when the components of the combination are given on different dosing schedules, e.g., one component is administered once daily and another component is administered every six hours, or when the pharmaceutical compositions are different, e.g., one is a tablet and one is a capsule. A kit comprising the separate dosage forms is therefore advantageous.

Compositions and Administration

When administered to a subject, the Fused Tricyclic Heterocycle Derivatives can be administered as a component of a composition that comprises a pharmaceutically acceptable carrier or vehicle. The present invention provides pharmaceutical compositions comprising an effective amount of at least one Fused Tricyclic Heterocycle Derivative and a pharmaceutically acceptable carrier. In the pharmaceutical compositions and methods of the present invention, the active ingredients will typically be administered in admixture with suitable carrier materials suitably selected with respect to the intended form of administration, i.e., oral tablets, capsules (either solid-filled, semi-solid filled or liquid filled), powders for constitution, oral gels, elixirs, dispersible granules, syrups, suspensions, and the like, and consistent with conventional pharmaceutical practices. For example, for oral administration in the form of tablets or capsules, the active drug component may be combined with any oral non-toxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Solid form preparations include powders, tablets, dispersible granules, capsules, cachets and suppositories. Powders and tablets may be comprised of from about 0.5 to about 95 percent inventive composition. Tablets, powders, cachets and capsules can be used as solid dosage forms suitable for oral administration.

Moreover, when desired or needed, suitable binders, lubricants, disintegrating agents and coloring agents may also be incorporated in the mixture. Suitable binders include starch, gelatin, natural sugars, corn sweeteners, natural and synthetic gums such as acacia, sodium alginate, carboxymethylcellulose, polyethylene glycol and waxes. Among the lubricants there may be mentioned for use in these dosage forms, boric acid, sodium benzoate, sodium acetate, sodium chloride, and the like. Disintegrants include starch, methylcellulose, guar gum, and the like. Sweetening and flavoring agents and preservatives may also be included where appropriate.

Liquid form preparations include solutions, suspensions and emulsions and may include water or water-propylene glycol solutions for parenteral injection.

Liquid form preparations may also include solutions for intranasal administration.

Also included are solid form preparations which are intended to be converted, shortly before use, to liquid form preparations for either oral or parenteral administration. Such liquid forms include solutions, suspensions and emulsions.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Additionally, the compositions of the present invention may be formulated in sustained release form to provide the rate controlled release of any one or more of the components or active ingredients to optimize therapeutic effects, i.e., antiviral activity and the like. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

In one embodiment, the one or more Fused Tricyclic Heterocycle Derivatives are administered orally.

In another embodiment, the one or more Fused Tricyclic Heterocycle Derivatives are administered intravenously.

In one embodiment, a pharmaceutical preparation comprising at least one Fused Tricyclic Heterocycle Derivative is in unit dosage form. In such form, the preparation is subdivided into unit doses containing effective amounts of the active components.

Compositions can be prepared according to conventional mixing, granulating or coating methods, respectively, and the present compositions can contain, in one embodiment, from about 0.1% to about 99% of the Fused Tricyclic Heterocycle Derivative(s) by weight or volume. In various embodiments, the present compositions can contain, in one embodiment, from about 1% to about 70% or from about 5% to about 60% of the Fused Tricyclic Heterocycle Derivative(s) by weight or volume.

The compounds of Formula I can be administered orally in a dosage range of 0.001 to 1000 mg/kg of mammal (e.g., human) body weight per day in a single dose or in divided doses. One dosage range is 0.01 to 500 mg/kg body weight per day orally in a single dose or in divided doses. Another dosage range is 0.1 to 100 mg/kg body weight per day orally in single or divided doses. For oral administration, the compositions can be provided in the form of tablets or capsules containing 1.0 to 500 milligrams of the active ingredient, particularly 1, 5, 10, 15, 20, 25, 50, 75, 100, 150, 200, 250, 300, 400, and 500 milligrams of the active ingredient for the symptomatic adjustment of the dosage to the subject to be treated. The specific dose level and frequency of dosage for any particular subject may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

For convenience, the total daily dosage may be divided and administered in portions during the day if desired. In one embodiment, the daily dosage is administered in one portion. In another embodiment, the total daily dosage is administered in two divided doses over a 24 hour period. In another embodiment, the total daily dosage is administered in three divided doses over a 24 hour period. In still another embodiment, the total daily dosage is administered in four divided doses over a 24 hour period.

The amount and frequency of administration of the Fused Tricyclic Heterocycle Derivatives will be regulated according to the judgment of the attending clinician considering such factors as age, condition and size of the subject as well as severity of the symptoms being treated. The compositions of the invention can further comprise one or more additional therapeutic agents, selected from those listed above herein. Accordingly, in one embodiment, the present invention provides compositions comprising: (i) at least one Fused Tricyclic Heterocycle Derivative or a pharmaceutically acceptable salt thereof; (ii) one or more additional therapeutic agents that are not a Fused Tricyclic Heterocycle Derivative; and (iii) a pharmaceutically acceptable carrier, wherein the amounts in the composition are together effective to treat HIV infection.

Kits

In one aspect, the present invention provides a kit comprising a therapeutically effective amount of at least one Fused Tricyclic Heterocycle Derivative, or a pharmaceutically acceptable salt or prodrug of said compound and a pharmaceutically acceptable carrier, vehicle or diluent.

In another aspect the present invention provides a kit comprising an amount of at least one Fused Tricyclic Heterocycle Derivative, or a pharmaceutically acceptable salt or prodrug of said compound and an amount of at least one additional therapeutic agent listed above, wherein the amounts of the two or more active ingredients result in a desired therapeutic effect. In one embodiment, the one or more Fused Tricyclic Heterocycle Derivatives and the one or more additional therapeutic agents are provided in the same container. In one embodiment, the one or more Fused Tricyclic Heterocycle Derivatives and the one or more additional therapeutic agents are provided in separate containers.

The present invention is not to be limited by the specific embodiments disclosed in the examples that are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

A number of references have been cited herein, the entire disclosures of which are incorporated herein by reference.

The invention claimed is:

1. A compound having the formula:

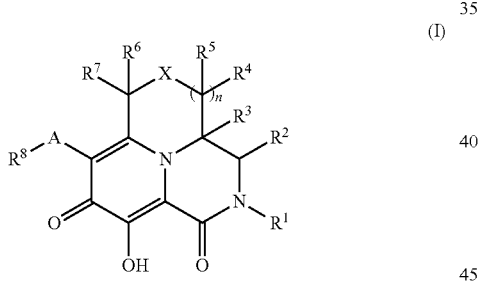

(I)

and pharmaceutically acceptable salts thereof,
wherein:
A is $C_1$-$C_4$ alkylene, $C_2$-$C_4$ alkenylene, arylene, $C_3$-$C_7$ cycloalkyl, 5 or 6-membered monocyclic heteroaryl, 4 to 7-membered heterocycloalkyl, —O—, —NH—C(O)—, —C(O)NH— or —C(O)—;
X is O, —N($C_1$-$C_6$ alkyl)- or —C($R^{10}$)($R^{11}$), such that when X=O or —N($C_1$-$C_6$ alkyl)-, then $R^4$, $R^5$, $R^6$ and $R^7$ are each other than —$OR^9$, —$N(R^9)_2$ or halo;
each occurrence of m is independently 0 or 1;
n is 0 or 1, such that when n is 0, then $R^4$ and $R^5$ are not present;
$R^1$ is $C_1$-$C_6$ alkyl, which is optionally substituted with up to 3 groups, each independently selected from $C_3$-$C_7$ cycloalkyl, 5 or 6-membered monocyclic heteroaryl, 4 to 6-membered monocyclic heterocycloalkyl, $C_6$-$C_{10}$ aryl, halo, $C_1$-$C_6$ haloalkyl, —$OR^9$, —$N(R^9)_2$, —$C(O)R^9$, —$C(O)N(R^9)_2$, —$NHC(O)R^9$ and —$SR^9$, wherein said $C_3$-$C_7$ cycloalkyl group, said 5 or 6-membered monocyclic heteroaryl group, said 4 to 6-membered monocyclic heterocycloalkyl group and said $C_6$-$C_{10}$ aryl group can each be optionally and independently substituted with one or more groups, each independently selected from $C_1$-$C_6$ alkyl, $C_3$-$C_7$ cycloalkyl, 5 or 6-membered monocyclic heteroaryl, 4 to 6-membered monocyclic heterocycloalkyl, $C_6$-$C_{10}$ aryl, halo, $C_1$-$C_6$ haloalkyl, —$OR^9$, —$N(R^9)_2$, —$C(O)R^9$, —$C(O)N(R^9)_2$, —$NHC(O)R^9$ and —$SR^9$;
$R^2$, $R^5$, $R^6$, $R^7$, $R^{10}$ and $R^{11}$ are each independently selected from H, $C_1$-$C_6$ alkyl, $C_3$-$C_7$ cycloalkyl, halo, $C_1$-$C_6$ haloalkyl, —$OR^9$, —$N(R^9)_2$, —$C(O)R^9$, —$C(O)N(R^9)_2$ and —$NHC(O)R^9$, wherein said $C_1$-$C_6$ alkyl group can be optionally substituted with one or more groups, each independently selected from halo, —OH, —O($C_1$-$C_6$ alkyl), —$NH_2$, —NH($C_1$-$C_6$ alkyl), —N($C_1$-$C_6$ alkyl)$_2$, —SH or —S($C_1$-$C_6$ alkyl);
$R^3$ is H, $C_1$-$C_6$ alkyl, $C_3$-$C_7$ cycloalkyl, $C_1$-$C_6$ haloalkyl, —$C(O)R^9$, —$C(O)N(R^9)_2$ and —NHC(O)$R^9$, wherein said $C_1$-$C_6$ alkyl group can be optionally substituted with one or more groups, each independently selected from halo, —OH, —O($C_1$-$C_6$ alkyl), —$NH_2$, —NH($C_1$-$C_6$ alkyl), —N($C_1$-$C_6$ alkyl)$_2$, —SH or —S($C_1$-$C_6$ alkyl);
$R^4$ is H, or $R^4$ and $R^5$ and the common carbon atom to which they are attached, join to form an endocyclic —C(O)— group;
$R^8$ is selected from $C_1$-$C_6$ alkyl, —($C_1$-$C_3$ alkylene)$_m$-($C_3$-$C_7$ cycloalkyl), —($C_1$-$C_3$ alkylene)$_m$-(5 or 6-membered monocyclic heteroaryl), —($C_1$-$C_3$ alkylene)$_m$-(4 to 6-membered monocyclic heterocycloalkyl) and —($C_1$-$C_3$ alkylene)$_m$-($C_6$-$C_{10}$ aryl), wherein said $C_3$-$C_7$ cycloalkyl group, said 5 or 6-membered monocyclic heteroaryl group, said 4 to 6-membered monocyclic heterocycloalkyl group and said $C_6$-$C_{10}$ aryl group can each be optionally and independently substituted with up to 5 groups, each independently selected from $C_1$-$C_6$ alkyl, $C_3$-$C_7$ cycloalkyl, 5 or 6-membered monocyclic heteroaryl, 4 to 6-membered monocyclic heterocycloalkyl, $C_6$-$C_{10}$ aryl, halo, $C_1$-$C_6$ haloalkyl, —$OR^9$, —$N(R^9)_2$, —$C(O)R^9$, —$C(O)N(R^9)_2$, —$NHC(O)R^9$ and —$SR^9$; and
each occurrence of $R^9$ is independently selected from H, $C_1$-$C_6$ alkyl, $C_3$-$C_7$ cycloalkyl, $C_6$-$C_{10}$ aryl and benzyl.

2. The compound of claim 1 having the formula:

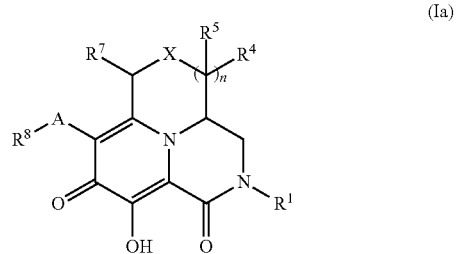

(Ia)

and pharmaceutically acceptable salts thereof,
wherein:
A is 5 or 6-membered monocyclic heteroaryl or —NH—C(O)—;
X is O, —N($C_1$-$C_6$ alkyl)- or —C($R^{10}$)($R^{11}$), such that when X=O or —N($C_1$-$C_6$ alkyl)-, then $R^4$, $R^5$, $R^6$ and $R^7$ are each other than —$OR^9$, —$N(R^9)_2$ or halo;

n is 0 or 1, such that when n is 0, then $R^4$ and $R^5$ are not present;

$R^1$ is $C_1$-$C_6$ alkyl, which is optionally substituted with a group selected from phenyl, $C_3$-$C_7$ cycloalkyl, 5 or 6-membered monocyclic heteroaryl and —$OR^9$, wherein said phenyl group and said 5 or 6-membered monocyclic heteroaryl group can each be optionally and independently substituted with up to two groups, each independently selected from $C_1$-$C_6$ alkyl, $C_3$-$C_7$ cycloalkyl, 5 or 6-membered monocyclic heteroaryl, 4 to 6-membered monocyclic heterocycloalkyl, $C_6$-$C_{10}$ aryl, halo, $C_1$-$C_6$ haloalkyl, —$OR^9$, —$N(R^9)_2$, —$C(O)R^9$, —$C(O)N(R^9)_2$, —$NHC(O)R^9$ and —$SR^9$;

$R^4$ is H, or $R^4$ and $R^5$ and the common carbon atom to which they are attached, join to form an endocyclic —C(O)— group;

$R^5$, $R^{10}$ and $R^{11}$ are each independently selected from H, $C_1$-$C_6$ alkyl and —$OR^9$;

$R^7$ is selected from H, $C_1$-$C_6$ alkyl, —$OR^9$ and —OH;

$R^8$ is selected from $C_1$-$C_6$ alkyl or benzyl, wherein the phenyl moiety of said benzyl group can be optionally and independently substituted with up to 3 groups, each independently selected from $C_1$-$C_6$ alkyl, $C_3$-$C_7$ cycloalkyl, 5 or 6-membered monocyclic heteroaryl, 4 to 6-membered monocyclic heterocycloalkyl, $C_6$-$C_{10}$ aryl, halo, $C_1$-$C_6$ haloalkyl, —$OR^9$, —$N(R^9)_2$, —$C(O)R^9$, —$C(O)N(R^9)_2$, —$NHC(O)R^9$ and —$SR^9$; and each occurrence of $R^9$ is independently selected from H, $C_1$-$C_6$ alkyl, $C_3$-$C_7$ cycloalkyl, $C_6$-$C_{10}$ aryl and benzyl.

3. The compound of claim 1 having the formula (Ib):

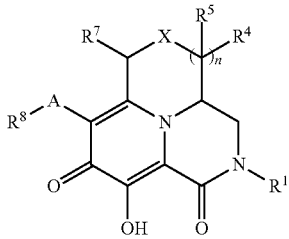

(Ib)

and pharmaceutically acceptable salts and prodrugs thereof, wherein:

A is pyrazolyl, thiadiazolyl, triazolyl, thiazolyl, oxazolyl, oxadiazaolyl or —NHC(O)—;

X is O, —$N(C_1$-$C_6$ alkyl)- or —$C(R^{10})(R^{11})$, such that when X=O or —$N(C_1$-$C_6$ alkyl)-, then $R^4$, $R^5$, $R^6$ and $R^7$ are each other than —$OR^9$, —$N(R^9)_2$ or halo;

n is 0 or 1, such that when n is 0, then $R^4$ and $R^5$ are not present;

$R^1$ is $C_1$-$C_6$ alkyl, which is optionally substituted with a group selected from phenyl, $C_3$-$C_7$ cycloalkyl, 5 or 6-membered monocyclic heteroaryl and —O—($C_1$-$C_6$ alkyl), wherein said phenyl group and said 5 or 6-membered monocyclic heteroaryl group can each be optionally and independently substituted with up to two groups, each independently selected from $C_1$-$C_6$ alkyl, halo and —O—($C_1$-$C_6$ alkyl);

$R^4$ is H, or $R^4$ and $R^5$ and the common carbon atom to which they are attached, join to form an endocyclic —C(O)— group;

$R^5$, $R^{10}$ and $R^{11}$ are each independently selected from H, $C_1$-$C_6$ alkyl and —O—($C_1$-$C_6$ alkyl);

$R^7$ is selected from H, $C_1$-$C_6$ alkyl, —O—($C_1$-$C_6$ alkyl) and —OH;

$R^8$ is selected from $C_1$-$C_6$ alkyl or benzyl, wherein the phenyl moiety of said benzyl group can be optionally and independently substituted with up to 3 groups, each independently selected from $C_1$-$C_6$ alkyl, —O—($C_1$-$C_6$ alkyl) and halo; and each occurrence of $R^9$ is independently selected from H, $C_1$-$C_6$ alkyl, $C_3$-$C_7$ cycloalkyl, $C_6$-$C_{10}$ aryl and benzyl.

4. The compound of claim 1, wherein A is —NHC(O)—.

5. The compound of claim 1, wherein X is —O—; n is 1; and $R^4$, $R^5$ and $R^7$ are each H.

6. The compound of claim 1, wherein X is —$CH_2$—; n is 0; and $R^7$ is H or —OH.

7. The compound of claim 1, wherein $R^8$ is benzyl, wherein the phenyl moiety of said benzyl group can be optionally and independently substituted with up to 3 groups, each independently selected from F, Cl, and methyl.

8. The compound of claim 1, wherein $R^1$ is $C_1$-$C_6$ alkyl, which is optionally substituted with a group selected from phenyl, 5 or 6-membered monocyclic heteroaryl, $C_3$-$C_7$ cycloalkyl and methoxy, wherein said phenyl group and said 5 or 6-membered monocyclic heteroaryl group can each be optionally and independently substituted with up to two groups, each independently selected from methoxy, $C_1$-$C_6$ alkyl and fluoro.

9. The compound of claim 1 having the structure:

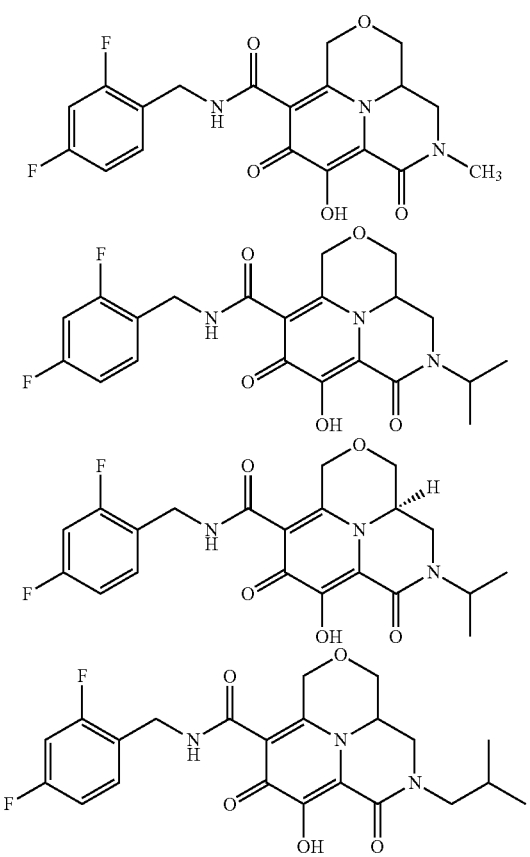

135
-continued
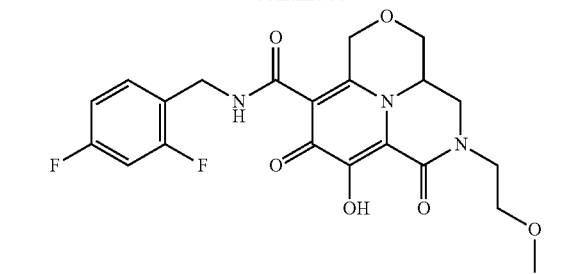
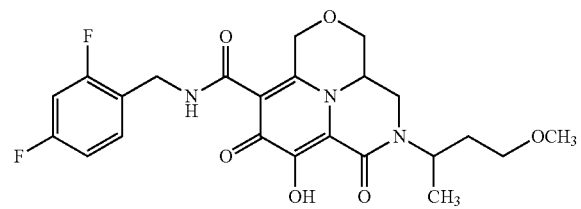
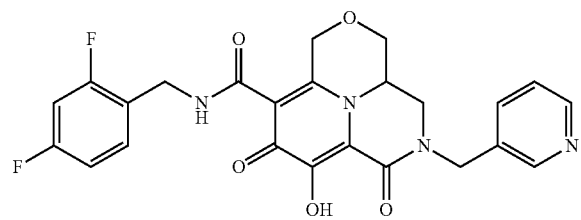
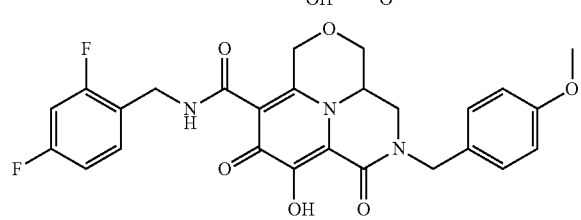
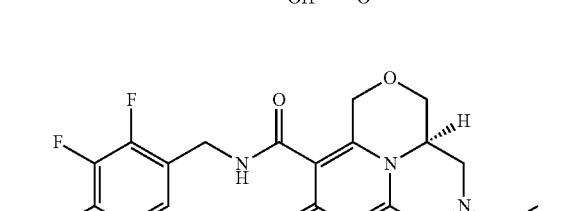
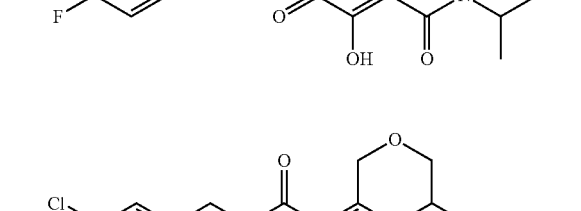
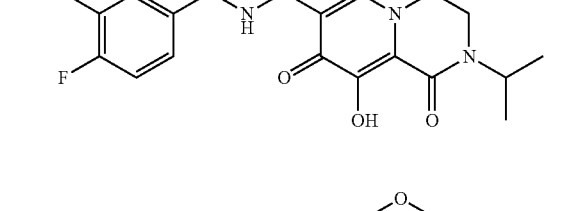
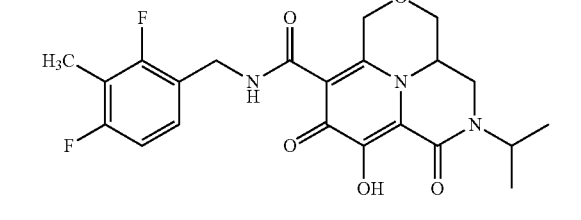
136
-continued
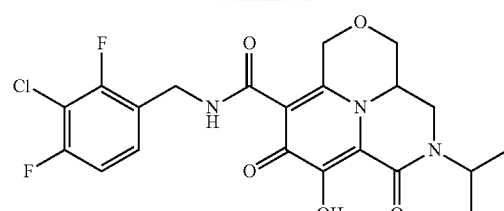
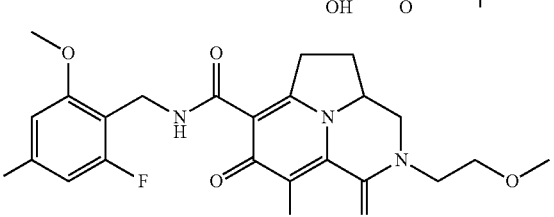
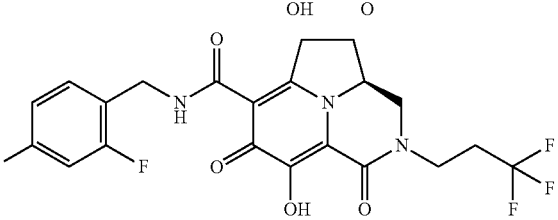
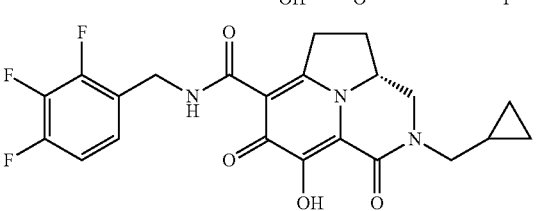
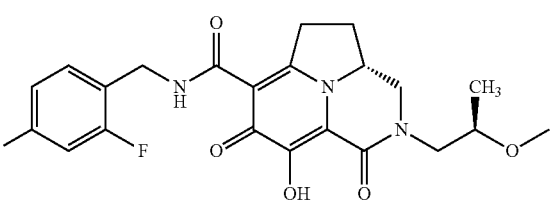
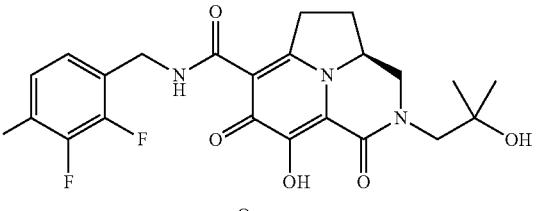
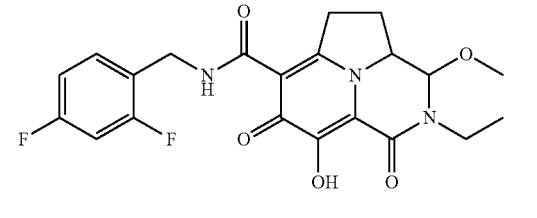
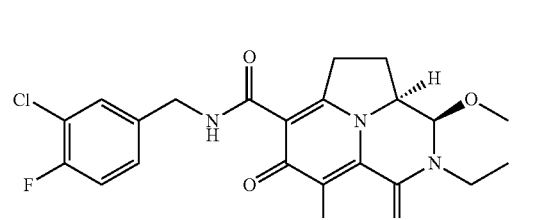

137
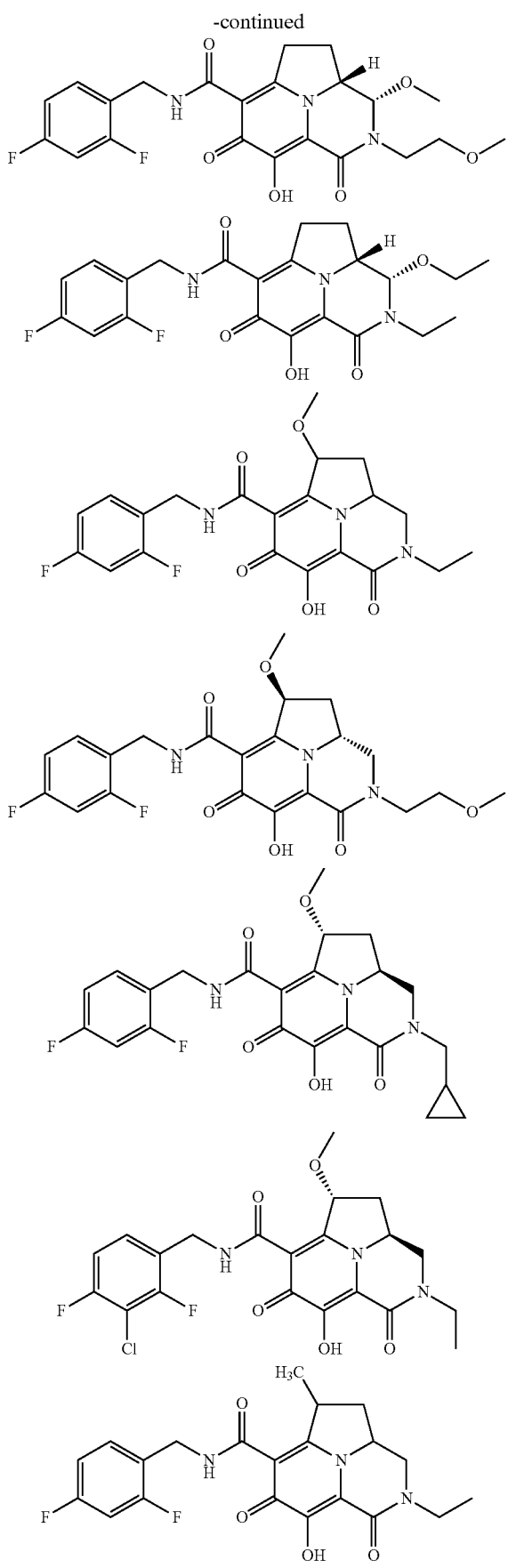
138
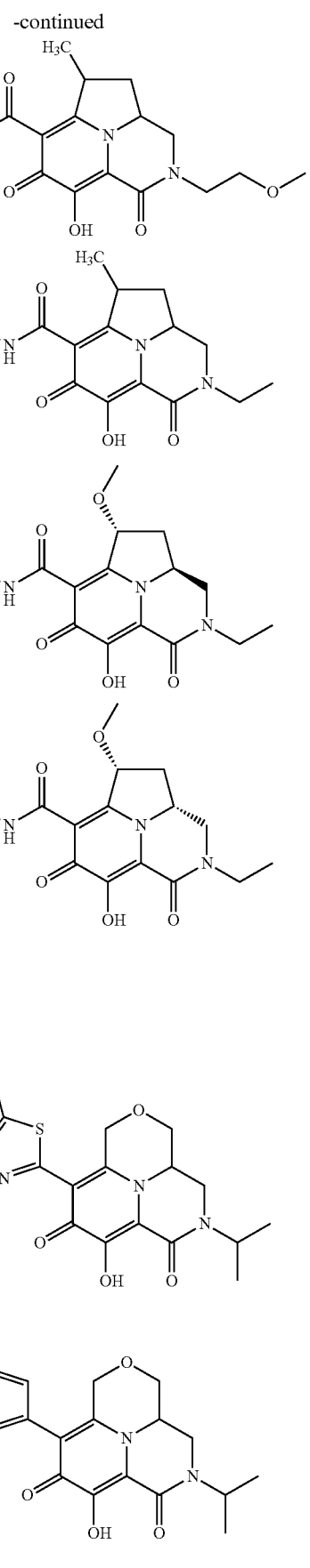

-continued

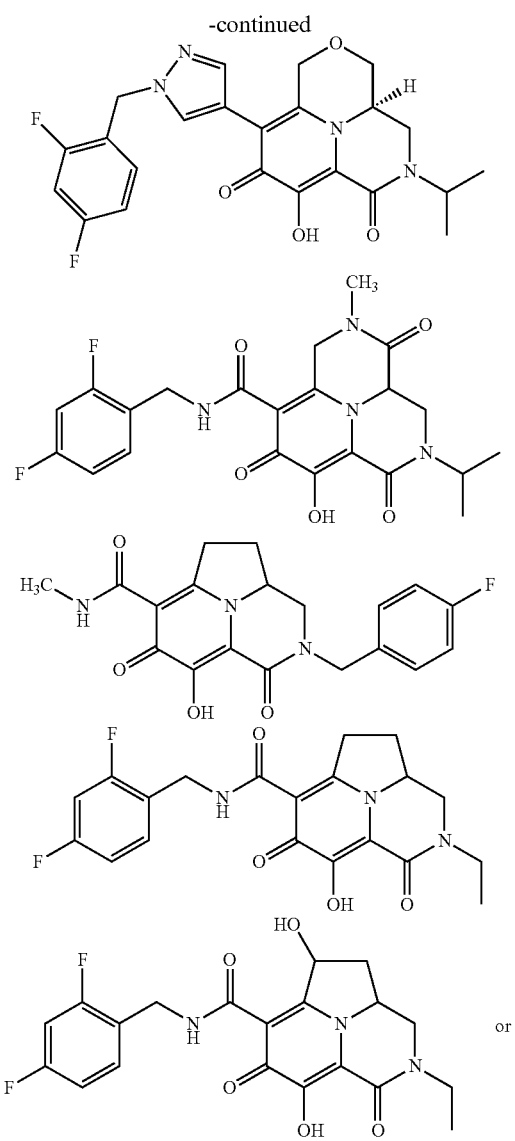

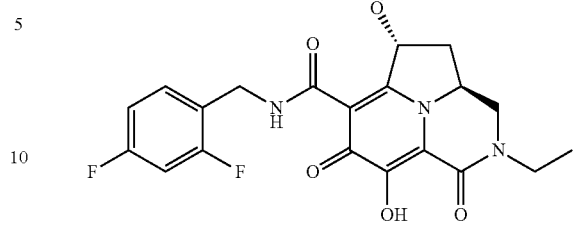

or a pharmaceutically acceptable salt thereof.

10. A pharmaceutical composition comprising an effective amount of a compound according to claim 1, or a pharmaceutically acceptable salt thereof, and a pharmaceutically acceptable carrier.

11. A method for the inhibition of HIV integrase in a subject in need thereof which comprises administering to the subject an effective amount of the compound according to claim 1, or a pharmaceutically acceptable salt or prodrug thereof.

12. A method for the treatment of infection by HIV or for the treatment, or delay in the onset or progression of AIDS in a subject in need thereof, which comprises administering to the subject an effective amount of the compound according to claim 1, or a pharmaceutically acceptable salt or prodrug thereof.

13. The pharmaceutical composition of claim 10, further comprising one or more additional therapeutic agents selected from raltegravir, lamivudine, abacavir, ritonavir, dolutegravir, arunavir, atazanavir, emtricitabine, tenofovir, elvitegravir, rilpivirine and lopinavir.

14. The method of claim 12, further comprising administering to the subject one or more additional therapeutic agents selected from raltegravir, dolutegravir, abacavir, lamivudine, ritonavir and lopinavir, wherein the amounts administered of the compound of claim 1, and the one or more additional therapeutic agents, are together effective to treat infection by HIV or to treat or delay the onset or progression of AIDS.

\* \* \* \* \*